US008603756B2

(12) United States Patent
Frost et al.

(10) Patent No.: US 8,603,756 B2
(45) Date of Patent: Dec. 10, 2013

(54) ANTIGEN SURROGATES IN AUTOIMMUNE DISEASE

(75) Inventors: Phillip Frost, Miami Beach, FL (US); Thomas Kodadek, Jupiter, FL (US)

(73) Assignee: OPKO Pharmaceuticals, LLC, Miami, FL (US)

(*) Notice: Subject to any disclaimer, the term of this patent is extended or adjusted under 35 U.S.C. 154(b) by 0 days.

(21) Appl. No.: 13/443,536

(22) Filed: Apr. 10, 2012

(65) Prior Publication Data
US 2012/0219574 A1   Aug. 30, 2012

Related U.S. Application Data

(63) Continuation of application No. PCT/US2012/020660, filed on Jan. 9, 2012.

(60) Provisional application No. 61/431,328, filed on Jan. 10, 2011.

(51) Int. Cl.
*G01N 33/53* (2006.01)

(52) U.S. Cl.
USPC ............................................ 435/7.1; 530/317

(58) Field of Classification Search
None
See application file for complete search history.

(56) References Cited

U.S. PATENT DOCUMENTS

| | | | |
|---|---|---|---|
| 2006/0078943 A1* | 4/2006 | Nur et al. ........................ 435/7.1 |
| 2010/0303805 A1 | 12/2010 | Moola et al. |
| 2010/0303835 A1 | 12/2010 | Gocke et al. |
| 2011/0092384 A1 | 4/2011 | Kwon et al. |

OTHER PUBLICATIONS

Reineke, Ulrich. Antibody epitope mapping using de novo generated systhetic peptide libraries. Methods in Molecular Biology, Epitope Mapping Protocol 2008, vol. 524, pp. 203-211.*
Payne et al. Genetic and functional characterization of human pemphigus vulgaris monoclonal autoantibodies isolated by phage display. The Journal of Clinical Inventigation, 2005, vol. 115, No. 4, pp. 888-899.*
Alluri, P., et al., "Isolation and Characterization of Coactovator-Binding Peptoids From a Combinatorial Library," Molecular BioSystems 2, 568-579, (2006).
Alluri P., et al "Isolation of Protein Ligands from Large Peptoid Libraries," J. Am. Chem. Soc., vol. 125, No. 46, 13995-14004 (2003).
Kodadek, T., et al., "Optimized Protocols for the Isolation of Specific Protein-Binding Peptides or Peptoids from Combinatorial Libraries Displayed on Beads," Molecular BioSystems 2, 25-35 (2006)
Kwon, Y., et al., "Encoded Combinatorial Libraries for the Construction of Cyclic Peptoid Microarrays," Chem. Commun., 5704-5706 (2008).
Kwon, Y., et al., "Quantitative Evaluation of the Relative Cell Permeability of Peptoids and Peptides," J. Am. Chem. Soc., vol. 129, No. 6. 1508-1509, (2007).
Li, S., et al., "Photolithographic Synthesis of Peptoids," J. Am. Chem. Soc., vol. 126, No. 13, 4088-4089 (2004).
Lim, H., et al., "Identification of a Peptoid Inhibitor of the Proteasome 19S Regulatory Particle," J. Am. Chem. Soc., vol. 129, No. 25, 7750-7751 (2007).
Lim, H., et al., "Periodate-Triggered Cross-Linking Reveals Sup2/Rpt4 as the Molecular Target of a Peptoid inhibitor of the 19S Proteasome Regulatory Particle," J. Am. Chem. Soc., vol. 129, No. 43, 12936-12937 (2007).
Lim, H., et al., "Rapid Identification of Improved Protein Ligands Using Peptoid Microarrays," Bioorganic & Medicinal Chemistry Letters 19, 3866-3869, (2009).
Lim, H., et al., "Rapid Identification of the Pharmacophore in a Peptoid Inhibitor of the Proteasome Regulatory Particle," Chem. Commun., 1064-1066 (2008).
Liu, B., et al., "A Potent Transactivation Domain Mimic with Activity in Living Cells," J. Am. Chem. Soc., vol. 127, No. 23, 8254-8255, (2005).
Olivos, H., et al., "Microwave-Assisted Solid-Phase Synthesis of Peptoids," Organic Letters, vol. 4, No. 23, 4057-4059 (2002).
Reddy, M., et al., "Protein "Fingerprinting" in Complex Mixtures with Peptoid Microarrays," PNAS, vol. 102, No. 36, 12672-12677 (2005).
Reddy, M., et al., "Transformation of Low-Affinity Lead Compounds into High-Affinity Protein Capture Agents," Chemistry & Biology, vol. 11, 1127-1137 (2004).
Shores K., et al., "Use of Peptide Analogue Diversity Library Beads for Increased Depth of Proteomic Analysis: Application to Cerebrospinal Fluid," Journal of Proteome Research, vol. 7, No. 5, 1922-1931 (2008).
Simpsons, L., et al., "Selective Toxin Sequestrants for the Treatment of Bacterial Infections," J. Am. Chem. Soc., vol. 131, No. 16, 5760-5762 (2009).
Tan, N., et al., "High-Throughput Evaluation of Relative Cell Permeability Between Peptoids and Peptides," Bioorganic & Medicinal Chemistry 16, 5853-5861 (2008).
Udugamasooriya, D., et al., "A Peptoid Antagonist of VEGF Receptor 2 Recognizes a 'Hotspot" in the Extracellular Domain Distinct from the Hormone-Binding site," Bioorganic & Medicinal Chemistry 16, 6:338-6343 (2008).
Udugamasooriya., D. et al., "A Peptoid "Antibody Surrogate" That Antagonizes VEGF Receptor 2 Activity," J. Am. Chem. Soc., vol. 130, No. 17, 5744-5752, (2008).
Udugamasooriya., D., et al., "The Pharmacophore of a Peptoid VEGF Receptor 2 Antagonist Includes Both Side Chain and Main Chain Residues," Bioorganic & Medicinal Chemistry Letters 18, 5892-5894 (2008).
Xiao, X., et al., "Design and Synthesis of a Cell-Permeable Synthetic Transcription Factor Mimic," Journal of Combinatorial Chemistry, vol. 9, No. 4, 592-600, (2007).
Zuckermann. R., et al., "Peptoids as Potential Therapeutics," Current Opinion in Molecular Therapeutics, vol. 11, No. 3, 299-307 (2009).

* cited by examiner

*Primary Examiner* — Shafiqul Haq
(74) *Attorney, Agent, or Firm* — OPKO Pharmaceuticals, LLC; Monte R. Browder

(57) ABSTRACT

The present invention provides for the identification of an antigen surrogate to the native antigens for the autoimmune disease pemphigus vulgaris. Ligands are discovered using large random peptoid or cyclic peptoid libraries that are screened against known antibodies to autoimmune diseases. The ligands may be useful as drugs in the treatment of such diseases and can also be used in combination with the concomitant removal of T-cells associated with autoimmune disorders.

4 Claims, 4 Drawing Sheets

1: Glu-Nmea-Npip-Nall-Nphe-Nall-Nffa-Nmea
2: Glu-Nall-Nleu-Npip-Nphe-Nleu-Nleu-Nmea
3: Glu-Nffa-Nmea-Nys-Npip-Nall-Nphe-Nmea
4: Glu-Nphe-Nffa-Nleu-Nffa-Npip-Nmea-Nmea
5: Glu-Nall-Nlys-Nffa-Nmea-Nleu-Nphe-Nmea

ANTIGEN SURROGATES IN AUTOIMMUNE DISEASE

This application is a by-pass-continuation and claims priority to PCT application No. PCT/US2012/020660 which was filed on Jan. 9, 2012 which claims priority to U.S. Provisional Application Ser. No. 61/431,328 filed Jan. 10, 2011.

BACKGROUND OF THE INVENTION

1. Field of the Invention

The present invention relates generally to the fields of molecular biology, immunology and medicine. More particularly, it concerns the identification of peptoids that are recognized by autoantibodies that are present in autoimmune diseases and conditions. These peptoids or other ligands can be used to identify subjects suffering from or at risk of autoimmune disease, as well as to prevent the autoantibodies from attacking the natural native antigens and, therefore, to treat the disease or condition.

2. Description of Related Art

The molecular basis of many autoimmune diseases remains unknown. Due in part to this lack of a molecular-level understanding, the state of the art in the development of diagnostic agents and effective therapies for autoimmune diseases is far from optimal. For example, there is no highly reliable serum protein marker for diagnosis of most autoimmune diseases. Almost without exception, drugs employed to treat these conditions either inhibit an event downstream of the autoimmune response itself, such as inflammation, or attempt to modulate or suppress the entire immune system non-selectively (Hemmer & Hartung, 2007), with significant undesirable side effects. For both diagnostic and therapeutic applications, one would ideally like to have molecules that target autoreactive B cells (and the antibodies they produce) and T cells directly, but ignore B and T cells that recognize foreign antigens. The present applicant has filed a patent application covering certain such molecules and methods, U.S. Ser. No. 12/789,711 and which is hereby incorporated by reference. Such molecules could be employed as diagnostic agents and research tools for the detection and enrichment of autoimmune antibodies, B cells and T cells. In addition, these molecules could serve as the foundation for a novel drug development program aimed at eradicating these autoreactive cells without affecting the proper function of the immune system. It is also known that certain libraries of random ligands on microarrays can screen for various disease associated biomarkers. U.S. patent application Ser. No. 11/433,069, also hereby incorporated by reference, teaches various random libraries of ligands that may be prepared and screened against biological samples having disease-associated biomarkers including antibodies and antibodies associated with autoimmune diseases. The present invention, on the other hand, is directed to a method of screening a library of ligands against autoantibodies that are known to be associated with a particular autoimmune disease in order to find antigen surrogates that are useful in binding to the autoantibody to prevent it from causing or acerbating the particular autoimmune disease. In addition, such ligands can also be used as diagnostics to screen individuals for autoimmune diseases and conditions. In a preferred embodiment, the present invention is directed to screening a library of cyclic peptoid ligands against at least one autoantibody associated with an autoimmune disease. U.S. patent application Ser. No. 12/905,605, hereby incorporated by reference, teaches the preparation of cyclic peptoid libraries. In another preferred embodiment, the screen can be a combination screen in which B-cells, T-cells or other cells which produce or cause the production of such antibodies are screened against a library of ligands to find high affinity ligands for such B-cells or T-cells pursuant to the methods disclosed in patent application Ser. No. 12/789,711 wherein said ligands are highly selective for B-cells producing such autoantibodies and/or T-cells which help stimulate the production of such antibody producing cells yet not selective for healthy cells or cells not associated with such autoimmune disorders. The methods used to pull such B-cells and/or T-cells out of the blood or fluid of patients in need of treatment thereof is combined with treatment of such patient having such autoimmune disorder with a high affinity ligand found pursuant to the methods disclosed herein by screening a ligand library against known autoantibodies associated with the disease in order to remove and/or mitigate the effects of the autoantibodies produced from such B-cells or assisted in such production by T-cells. The size of the library to screen against these known autoantibodies may range from 10,000 to millions of ligands depending upon the support system. Ligand libraries are prepared by methods disclosed in the art. Such references may be found in, for example, U.S. Ser. No. 11/433,069 which is hereby incorporated by reference.

SUMMARY OF THE INVENTION

The present invention provides methods of using synthetic molecules, i.e., ligands, that bind ligand binding moieties, such as proteins, nucleic acids, carbohydrates, or non-adherent cells present in complex biological mixtures as drugs for treating autoimmune disorders. Such ligands are found through library screening methodology of known autoantibodies associated with autoimmune diseases and disorders. The highly selective ligands found pursuant to the methods herein may have a wide range of structures and include any ligand which binds to or has an affinity for an autoantibody.

Thus, in accordance with the present invention, there is provided a method of identifying a ligand or peptoid that is specifically recognized by autoantibodies comprising (a) providing a ligand library of synthetic or natural molecules selected from peptides, nucleic acids, peptoids, cyclic peptoids, carbohydrates or other chemical libraries and (b) exposing said ligand library to autoantibodies associated with any particular autoimmune disease or disorder; and (c) identifying those ligands which bind to the autoimmune antibody (ies).

The present invention also includes use of such identified ligands to treat the associated autoimmune disease or condition. The ligands would typically have an affinity for the autoantibody of at least micromolar and preferably nanomolar affinity. The use involves a method of treating a patient in need of treatment thereof comprising administering the ligand to the patient in the form of a pharmaceutical composition. The pharmaceutical composition comprises a ligand found in the screening methodology combined with a pharmaceutically acceptable excipient. The delivery method may be by any known means including oral delivery or parenteral delivery.

The autoimmune disease may be multiple sclerosis or rheumatoid arthritis or any number of other autoimmune diseases or disorders including pemphigus vulgaris.

The ligand or peptoid may be a 3-mer, a 4-mer, a 5-mer, a 6-mer, a 7-mer, an 8-mer, a 9-mer or a 10-mer or larger oligomer (e.g., 11 mer to 16 mer). The ligand may be a constrained oligomer of any kind. In particular, constrained oligomers of peptoids are preferably used in the present invention. The present invention thus relates to a method of treating an autoimmune disorder or condition with a constrained oligomer. The term "constrained" is a relative term and in this application, more contrained oligomers include cyclic peptides and other oligomers that are relatively more constrained than, for example, a linear peptoid or linear peptoid like moiety. The more preferred compounds for treating an autoimmune disorder such as Pemphigus vulgaris include such constrained oligomers like cyclic peptides. The present invention thus relates to a method of treating an autoimmune disorder or condition comprising administering a pharmaceutically effective amount of a constrained ligand selected from the group consisting of a peptoid or peptoid like molecule including cyclic peptides or other such molecules that are relatively stiffer and resemble the "bound conformation" of such molecule. The term "bound conformation" means the conformation of the molecule when it is bound to the particular target receptor site or active site on an autoantibody. The bound or constrained ligand is also called an antigen surrogate herein. Reference to constrained or "stiffer" peptoids is specifically found in U.S. application Ser. No. 12/905,605 and published as US2011/0092384 which is specifically incorporated by reference.

The antigen surrogate found pursuant to the screening methodologies recited herein may also be used in combination with a ligand that is discovered or found by a method of identifying a ligand that is specifically recognized by autoimmune T or B cells comprising:

(a) providing a first T cell or B cell population from a healthy subject, wherein said population is labeled with a first detectable label;
(b) providing a second T cell or B cell population from a subject having an autoimmune disease, wherein said population is labeled with a second detectable label;
(c) contacting said first and second T cell or B cell populations with a plurality of candidate ligands; and
(d) assessing binding of said first and second T cell or B cell populations to said candidate ligands, wherein if said ligand binds to said second T cell or B cell population but not to said first T cell or B cell population, the said ligand is recognized by autoimmune but not healthy T cells or B cells.

The first and second labels referenced above may be fluorescent or chemiluminescent, or quantum dots or any other known label known in the art.

The peptoid or ligands used in any one of the processes or methods described herein may be bound to a support, such as a bead, a chip, a filter, a dipstick, microarray, a membrane, a polymer matrix or a well. The contacting step, in the case of the screening of T-cells when used in combination with the use of autoantibody screens may comprise bringing said support into contact with said first and second T cell populations at the same time. The T cell population may comprise $CD4^+$ T cells. The subjects may be human or animal.

In another embodiment, there is provided a method of removing an autoantibody from a subject suffering from an autoimmune disease comprising administering a ligand or peptoid that binds specifically to autoimmune antibodies. The autoimmune disease may be multiple sclerosis or rheumatoid arthritis or any of the other numerous autoimmune diseases or conditions.

The ligand or peptoid may be a 3-mer, a 4-mer, a 5-mer, a6-mer, a 7-mer, an 8-mer, a 9-mer or a 10-mer or larger. The "R" groups shown in FIG. 1 may be any peptoid substituent as recited herein or as described in U.S. application Ser. No. 12/789,711 or in U.S. application Ser. No. 12/791,389 which are hereby incorporated by reference. The "n" in the structures shown in FIG. 1 is preferably 3 but may be from 2-7.

The ligand or peptoid may be a 3-mer, a 4-mer, a 5-mer, a 6-mer, a 7-mer, an 8-mer, a 9-mer or a 10-mer. A toxin when used in combination with or combined with a ligand disclosed herein with respect to some combination treatment embodiments may be ricin, diphtheria toxin or cholera toxin. Alternatively, the toxin may be a photo-activated toxin, such as ruthenium(II) tris-bipydidyl, and step (b) may further comprise exposing said sample to visible light. The sample may be blood, cerebrospinal fluid or semen. The method may further comprise obtaining said sample from said subject. The subject may be human or animal.

In still yet another embodiment, there is provided a combination treatment which comprises (1) a method of killing an autoimmune T cell obtained from or in a subject suffering from an autoimmune disease comprising (a) providing a ligand or peptoid that binds specifically to autoimmune T cells, wherein said ligand or peptoid is conjugated to an IgG Fc-containing molecule; and (b) contacting an autoimmune T cell population with said conjugate for a sufficient time to permit binding of at least one autoimmune T cell to said conjugate, wherein said conjugate recruits immune effectors to said autoimmune T cells resulting in death thereof. The autoimmune T cell population may be treated ex vivo, and the method may further comprise returning the sample of step (b) to said subject and (2) treating said patient with an antigen surrogate. The autoimmune disease may be multiple sclerosis or rheumatoid arthritis or any autoimmune disease. In the present invention, the embodiment involves use of this method (1) in combination with treatment of the patient with an antigen surrogate found through the methods recited herein.

The ligand or peptoid may be a 3-mer, a 4-mer, a 5-mer, a 6-mer, a 7-mer, an 8-mer, a 9-mer or a 10-mer or larger. The IgG Fc-containing molecule may be an antibody, a single chain antibody, or a Fc fragment, for example, an antibody or a single chain antibody, and said ligand or peptoid is tethered to the antigen binding site of said antibody, or an Fc fragment lacking IgG variable regions, and said ligand or peptoid is tethered to the carboxy-terminus of said Fc fragment. The sample, in the event T-cells or other cells are screened, may be blood, cerebrospinal fluid or semen. The method may further comprise obtaining said sample from said subject. The subject may be human or animal. In the case of the initial screen for the autoantibody ligand, the sample is or contains a known or isolated autoantibody. This autoantibody may be labeled or a non-labeled autoantibody bound to a ligand antibody that may be detected with a labeled secondary antibody. The sample is preferably a diluted sample having the known autoantibody.

For diagnostic purposes, once the antigen surrogate is detected and identified, said surrogate may be used in a diagnostic kit alone or in combination with a T-cell kit or in combination with T-cell ligands to detect autoimmune disease in patient samples.

In certain embodiments, compounds of the invention used in combination with the antigen surrogates, wherein the compounds for autoimmune T-cell detection have the following formulas:

Formula II

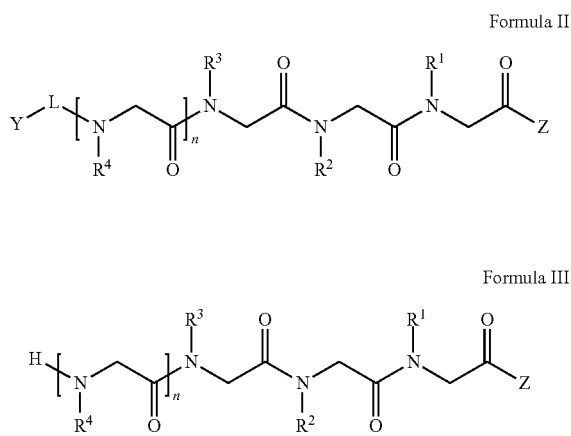

Formula III wherein n is 0-8; L is linker; Y is toxin or antibody fragments; Z is $NH_2$, $N(C1-C6\ alkyl)_2$, OH or $O(C1-C6\ alkyl)$; and R1, R2, R3, R4, R5, R6, R7, R8 (with each value of n above 4 adding a next R group in numerical order to Formula II or Formula III), can be hydrogen; alkyl; allyl; methyl; ethyl; n-propyl; isopropyl; n-butyl; isobutyl; sec-butyl; tert-butyl; pentyl; hexyl; isopentyl; aryl; heteroaryl; furanyl; indolyl; thiophenyl; thiazolyl; imidazolyl; isoxazoyl; oxazoyl; piperonyl; pyrazoyl; pyrrolyl; pyrazinyl; pyridyl; pyrimidyl; pyrimidinyl; purinyl; cinnolinyl; benzofuranyl; benzothienyl; benzotriazolyl; benzoxazolyl; quinoline; isoxazolyl; isoquinoline cycloalkyl; alkenyl; cycloalkenyl; phenyl; pyridyl; methoxyethyl; (R)-methylbenzyl; C1-C6 alkyl unsubstituted or substituted with $NH_2$, OH, or SH; C2-C6 alkynyl unsubstituted or substituted with NH2; OH or SH.

In certain aspects, R1 is C1-C6 alkyl terminally substituted with a NH2, particularly 4 aminobutane.

In further aspects, R2 is C1-C6 alkyl terminally substituted with a NH2, particularly 4 aminobutane.

In still further aspects, R3 is C1-C6 alkyl and particularly isobutyl.

In certain aspects, R4 is C1-C6 alkyl terminally substituted with a NH2, particularly 4 aminobutane.

In further aspects, R5 is (R)-methylbenzyl

In still further aspects, R6 is furanyl.

In certain aspects, R7 is C1-C6 alkyl terminally substituted with a NH2, particularly 4 aminobutane.

In further aspects R8 is C1-C6 alkyl and particularly isobutyl.

Certain embodiments of the invention include 8-mer where R1, R2, R4, and R7 are 4-aminobutane; R3 and R8 are isobutyl; R5 is (R)-methylbenzyl; and R6 is furanyl (compound AG12A). AG12A can terminate in a lysyl (4-aminobutane), hydroxyl, or carboxyl group.

In other aspects the terminal R group terminates in a lysyl, carboxyl, or hydroxyl group.

In other embodiments of the invention, antigen surrogates found by the process of the invention including the candidate peptoids or cyclic peptoids may also have any of the R groups specified above for a substituent on the amine of the peptoid. When the invention comprises antigen surrogates to autoantibodies of pemphigus vulgaris, the preferred compound is a compound of formula I:

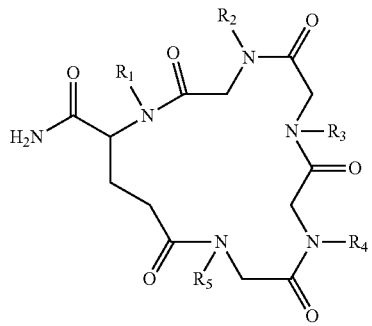

wherein R1-R5 is independently selected from hydrogen; alkyl; allyl; methyl; ethyl; n-propyl; isopropyl; n-butyl; isobutyl; sec-butyl; tert-butyl; pentyl; hexyl; isopentyl; aryl; heteroaryl; furanyl; indolyl; thiophenyl; thiazolyl; imidazolyl; isoxazoyl; oxazoyl; piperonyl; pyrazoyl; pyrrolyl; pyrazinyl; pyridyl; pyrimidyl; pyrimidinyl; purinyl; cinnolinyl; benzofuranyl; benzothienyl; benzotriazolyl; benzoxazolyl; quinoline; isoxazolyl; isoquinoline cycloalkyl; alkenyl; cycloalkenyl; phenyl; pyridyl; methoxyethyl; (R)-methylbenzyl; C1-C6 alkyl; each of which may be independently unsubstituted or substituted with halogen (Cl, F, Br, I), $—NH_2$. —OH, $—OC1-C6alkyl$ or —SH; C2-C6 alkynyl unsubstituted or substituted with $NH_2$; OH or SH or pharmaceutically acceptable salts thereof. The cyclic peptoid is linked to a support such as a microarray or other support via the NH2 group of the amide moiety on the left side of the molecule as shown above.

In a preferred embodiment, the cyclic peptoid that acts as an antigen surrogate in pemphigus vulgaris is:

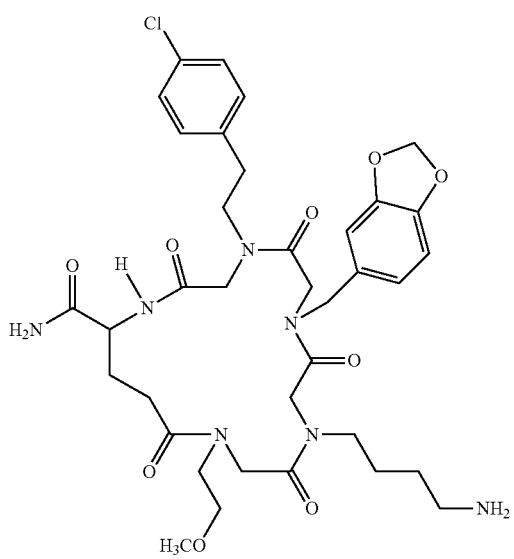 [SMILES: COCCN1CC(=O)N(CCCCN)CC(=O)N(Cc2ccc3c(c2)OCO3)CC(=O)N(CCc2ccc(Cl)cc2)CC(=O)NC(C(N)=O)CCC1=O]

The present invention also relates to a method of treating a patient having an autoimmune disorder comprising administering an antigen surrogate selected from a constrained oligomer. The method preferably relates to a method of treating said patient wherein the autoimmune disorder is selected from Pemphigus vulgaris. Preferrably, in the method the constrained oligomer is selected from a peptoid or peptoid-like moiety.

The present invention also comprises a pharmaceutical composition comprising an antigen surrogate selected from the group consisting of constrained oligomers and a pharmaceutically acceptable excipient.

The invention further comprises a method of identifying a constrained ligand that is specifically recognized by autoimmune T cells comprising:
(a) Providing a first T cell population from a healthy subject, wherein said population is labeled with a first detectable label;
(b) Providing a second T cell population from a subject suspected of or having an autoimmune disease or disorder, wherein said population is labeled with a second detectable label;
(c) Contacting said first and second T cell populations with a plurality of constrained ligands or a combination of contstrained ligands and unconstrained ligands; and
(d) Assessing binding of said first and second T cell populations to said constrained ligands or combination of constrained ligands and unconstrained ligands.

In said method, the preferred autoimmune disease or disorder is Pemphigus vulgaris.

The invention also comprises a method of removing an autoimmune T cell from a subject suffering from an autoimmune disease or disorder comprising:
(a) providing a constrained ligand that binds specifically to autoimmune T cells, wherein said constrained ligand is bound to a support;
(b) contacting a T cell-containing sample from said subject with said support-bound constrained ligand for a sufficient time to permit binding of autoimmune T cells to said support-bound constrained ligand; and
(c) separating said support from said sample.

The method further comprises returning said sample of step (c) to said subject.

In said method the preferred autoimmune disease or disorder is Pemphigus vulgaris.

The invention also relates to a vaccine for the treatment of an autoimmune disease or condition comprising a constrained oligomer. Administration of said vaccine or antigen surrogate when administered as a vaccine alone or in combination with a vaccine adjuvant is sufficient to treat an autoimmune disease or condition.

The present invention also relates to a method of killing an autoimmune T cell obtained from a subject suffering from an autoimmune disease or disorder comprising:
(a) Providing a constrained ligand that binds specifically to autoimmune T cells, wherein said ligand is conjugated to a toxin;
(b) Contacting said T cell-containing sample from said subject with said conjugate for a sufficient time to permit binding of at least one autoimmune T cell to said conjugate, wherein said conjugate causes the death of said autoimmune T cell.

The method further comprises treating the sample ex vivo, and returning the sample to said subject.

The preferred method of treatment above relates to an autoimmune disease or disorder selected from Pemphigus vulgaris.

The invention also relates to a method of killing an autoimmune T cell obtained from or in a subject suffering from an autoimmune disease or disorder comprising:
(a) Providing a constrained ligand that binds specifically to an autoimmune T cell wherein said constrained ligand is conjugated to an IgG Fc-containing molecule; and
(b) Contacting an autoimmune T cell population with said conjugated for a sufficient time to permit binding of at least one autoimmune T cell to said conjugate, wherein said conjugate recruits immune effectors to said autoimmune T cells resulting in death thereof.

The method further comprises treating said autoimmune T cell population ex vivo and returning said sample to said subject.

The preferred autoimmune disease or disorder in the above method is Pemphigus vulgaris. The preferred antigen surrogate or constrained ligand is a peptoid or peptoid like moiety.

The invention further comprises the above method wherein said IgG Fc-containing molecule is an antibody, a single chain antibody or a Fc fragment.

The invention further comprises the above method wherein said IgG Fc-containing molecule is an antibody or a single chain antibody, and said constrained ligand is tethered to the antigen binding site of said antibody.

The invention further relates to the above method wherein said IgG Fc-containing molecule is an Fc fragment lacking IgG variable regions and said constrained ligand is tethered to the carboxy-terminus of said Fc fragment.

The present invention also relates to a method of treating a particular autoimmune disease or disorder in a patient in need of treatment thereof comprising the steps of:
(a) screening a ligand library against a particular autoantibody associated with a particular autoimmune disease or condition to find a high affinity ligand;
(b) identifying a high affinity ligand to said particular autoantibody associated with said particular autoimmune disease or disorder;
(c) isolating said high affinity ligand from said library; and
(d) treating said patient with the isolated high affinity ligand.

The preferred particular autoimmune disease or disorder is Pemphigus vulgaris.

The present invention also relates to a pharmaceutical composition comprising a high affinity ligand identified according to the above method in the preceding paragraph.

In a preferred embodiment, the composition comprises a high affinity ligand selected from a constrained oligomer.

In a preferred embodiment, the composition comprises a constrained oligomer selected from a peptoid, peptoid-like moiety or a cyclic peptoid.

The present invention also relates to a method of identifying high affinity ligands to autoantibodies associated with a particular autoimmune disease or disorder comprising the steps of (1) selecting an autoantibody associated with a particular autoimmune disease or disorder and (2) screening a library of ligands against said autoantibody and (3) identifying a high affinity ligand that selectively binds to said autoantibody. The invention also relates to use of said high affinity ligand in the treatment of said autoimmune disease or disorder or in the diagnosis of such disease or disorder.

The present invention also relates to combination therapy comprising treating a patient having a particular autoimmune disease or disorder in need of treatment thereof with a combination comprising (a) a high affinity ligand having specificity for an autoantibody associated with said particular autoimmune disease or disorder and (b) a ligand having specify for a T cell associated with said particular autoimmune disease or disorder.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed in this specification can be implemented with respect to any method or composition of the invention, and vice versa. Furthermore, compositions and kits of the invention can be used to achieve methods of the invention.

Throughout this application, the term "about" is used to indicate that a value includes the inherent variation of error for the device, the method being employed to determine the value, or the variation that exists among the study subjects.

DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 3A) General structure of the cyclic and linear molecules made on each bead before cleavage and deprotection of the thiol side chain. Below: Sequences of the variable regions of five peptoids picked for the spotting experiment. (FIG. 3B) Fluorescent image of microarrays in which each of the five peptoids have been spotted onto the activated surface. A DMSO solution of each peptoid (≈2 mM) was spotted two times, the solution was diluted three-fold, spotted again, etc. After washing and drying, the arrays were hybridized with Cy3-conjugated streptavidin, washed and the slide was scanned with a fluorescence scanner (see ref. 30 for details). The spots are false-colored green. (FIG. 3C) The Cys is essential for retention of the peptoid on the microarray. Two peptoids were synthesized. Each had the sequence Fluorescein-Nlys-Nser-Nleu-Nser-Nall-Npip-Nlys-Nlys. One peptoid also contained a C-terminal cysteine, while the other did not. The two peptoids were spotted onto a maleimide-activated glass slide. After washing, the slide was scanned using a fluorescence scanner. The fluorescence intensity is false-colored blue.

DESCRIPTION OF ILLUSTRATIVE EMBODIMENTS

Figure 1:
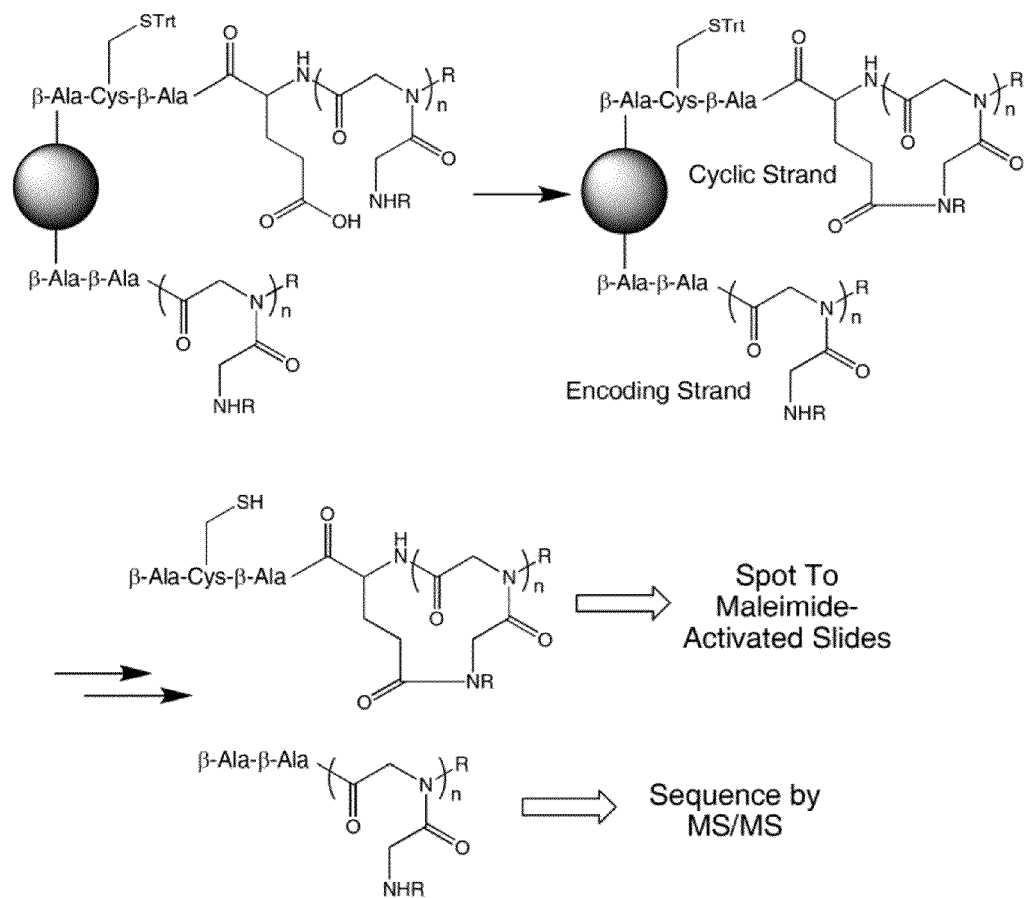
FIG. 1—Schematic view of the general strategy employed to create a library in which each bead carries a cyclic peptoid and an analogous linear encoding strand. Only the cyclic molecule contains a thiol and thus will couple to a maleimide-activated glass slide FIG. 2—Synthesis of the encoded cyclic peptoid library via the one bead two compound strategy. The amines employed in the sub-monomer peptoid synthesis are shown at the bottom of the figure (one of the amines in 1,4-diaminobutane and a hydroxyl group in ethanolamine were protected).

The inventors here describe methods of identifying synthetic molecules that bind with high specificity to autoantibodies and to combinations of ligands which bind to autoantibodies and autoreactive CD4+ T cells or B cells. For purposes of such a combination invention, a protocol is described here in the context of experimental autoimmune encephalomyelitis (EAE), an animal model for human multiple sclerosis (MS), and which does not require prior knowledge of the nature of the native antigen(s). Instead, it employs a comparative binding strategy in which the ability of each compound in the library to bind autoreactive T cells and normal T cells in a native population is assessed simultaneously. Only compounds that exhibit high selectivity for autoreactive T cells are selected as "hits" that can be used in combination with "hits" from screens for ligands that bind to autoantibodies associated with autoimmune diseases or disorders. Alternatively or additionally, constrained oligomers may be directly screened against T-cells according to the processes described herein. Such constrained oligomers found to selectively bind to T-cells are also within the scope of the present invention. Combination therapy can include successive treatments with a ligand that has an affinity for a disease causing autoantibody and treatment with a ligand that has an affinity for a T-cell associated with the autoimmune disease or condition. The skilled physician will determine the appropriate regimin on a patient by patient basis.

Detailed characterization of one hit from the EAE screen suggests that it binds to the T cell receptor (TCR). Furthermore, this compound is shown to be an antagonist of antigen-driven T cell proliferation in vitro. Finally, when this compound is conjugated to a ruthenium complex capable of mediating oxidative damage to nearby proteins when photolyzed (Lee et al., 2008), the conjugate inhibits the ability of autoreactive T cells to mediate disease in an adoptive transfer experiment. Taken together, these data prove the capability of this technology to identify synthetic compounds that are capable of binding and inhibiting antigen-specific autoreactive T cells. Once these T cells are identified, they may be used in the combination therapy described herein.

I. AUTOIMMUNE DISEASES

The present invention, as discussed above, provides for the identification of molecules that can bind autoantibodies or autobodies used in combination with molecules that bind autoimmune T-cells from a variety of disease states. In certain aspects, disease states include, but are not limited to diseases such as acute disseminated encephalomyelitis (ADEM), acute necrotizing hemorrhagic leukoencephalitis, Addison's disease, agammaglobulinemia, allergic asthma, allergic rhinitis, alopecia areata, amyloidosis, ankylosing spondylitis, anti-GBM/anti-TBM nephritis, antiphospholipid syndrome (APS), autoimmune aplastic anemia, autoimmune dysautonomia, autoimmune hepatitius, autoimmune hyperlipidemia, autoimmune immunodeficiency, autoimmune inner ear disease (AIED), autoimmune myocarditis, autoimmune pancreatitis, autoimmune retinopathy, autoimmune thrombocytopenic purpura (ATP), autoimmune thyroid disease, axonal & neuronal neuropathies, Balo disease, Behcet's disease, bullous pemphigoid, cardiomyopathy, Castlemen disease, celiac sprue (non-tropical), Chagas disease, chronic fatigue syndrome, chronic inflammatory demyelinating polyneuropathy (CIDP), chronic recurrent multifocal ostomyelitis (CRMO), Churg-Strauss syndrome, cicatricial pemphigoid/henign mucosal pemphigoid, Crohn's disease, Cogan's syndrome, cold agglutinin disease, congenital heart block, coxsackie myocarditis, CREST disease, essential mixed cryoglobulinemia, demyelinating neuropathies, dermatomyositis, Devic's disease (neuromyelitis optica), discoid lupus, Dressler's syndrome, endometriosis, eosinophillic fasciitis, erythema nodosum, experimental allergic encephalomyelitis, Evan's syndrome, fibromyalgia, fibrosing alveolitis, giant cell arteritis (temporal arteritis), glomerulonephritis, Goodpasture's syndrome, Grave's disease, Guillain-Barre syndrome, Hashimoto's encephalitis, Hashimoto's thyroiditis, hemolytic anemia, Henock-Schoniein purpura, herpes gestationis, hypogammaglobulinemia, idiopathic thrombocytopenic purpura (ITP), IgA nephropathy, immunoregulatory lipoproteins, inclusion body myositis, insulin-dependent diabetes (type 1), interstitial cystitis, juvenile arthritis, juvenile diabetes, Kawasaki syndrome, Lambert-Eaton syndrome, leukocytoclastic vasculitis, lichen planus, lichen sclerosus, ligneous conjunctivitis, linear IgA disease (LAD), Lupus (SLE), Lyme disease, Meniere's disease, microscopic polyangitis, mixed connective tissue disease (MCTD), Mooren's ulcer, Mucha-Habermann disease, multiple sclerosis, myasthenia gravis, myositis, narcolepsy, neuromyelitis optica (Devic's), neutropenia, ocular cicatricial pemphigoid, optic neuritis, palindromic rheumatism, PANDAS (Pediatric Autoimmune Neuropsychiatric Disorders Associated with *Streptococcus*), paraneoplastic cerebellar degeneration, paroxysmal nocturnal hemoglobinuria (PNH), Parry Romberg syndrome, Parsonnage-Turner syndrome, pars plantis (peripheral uveitis), pemphigus, peripheral neuropathy, perivenous encephalomyelitis, pernicious anemia, POEMS syndrome, polyarteritis nodosa, type I, II & III autoimmune polyglandular syndromes, polymyalgia rheumatic, polymyositis, postmyocardial infarction syndrome, postpericardiotomy syndrome, progesterone dermatitis, primary biliary cirrhosis, primary sclerosing cholangitis, psoriasis, psoriatic arthritis, idiopathic pulmonary fibrosis, pyoderma gangrenosum, pure red cell aplasia, Raynaud's phenomena, reflex sympathetic dystrophy, Reiter's syndrome, relapsing polychondritis, restless legs syndrome, retroperitoneal fibrosis, rheumatic fever, rheumatoid arthritis, sarcoidosis, Schmidt syndrome, scleritis, scleroderma, Slogren's syndrome, sperm and testicular autoimmunity, stiff person syndrome, subacute bacterial endocarditis (SBE), sympathetic ophthalmia, Takayasu's arteritis, temporal arteritis/giant cell arteries, thrombocytopenic purpura (TPP), Tolosa-Hunt syndrome, transverse myelitis, ulcerative colitis, undifferentiated connective tissue disease (UCTD), uveitis, vasculitis, vesiculobullous dermatosis, vitiligo or Wegener's granulomatosis or, chronic active hepatitis, primary biliary cirrhosis, cadilated cardiomyopathy, myocarditis, autoimmune polyendocrine syndrome type I (APS-I), cystic fibrosis vasculitides, acquired hypoparathyroidism, coronary artery disease, pemphigus foliaceus, pemphigus vulgaris, Rasmussen encephalitis, autoimmune gastritis, insulin hypoglycemic syndrome (Hirata disease), Type B insulin resistance, acanthosis, systemic lupus erythematosus (SLE), pernicious anemia, treatment-resistant Lyme arthritis, polyneuropathy, demyelinating diseases, atopic dermatitis, autoimmune hypothyroidism, vitiligo, thyroid associated ophthalmopathy, autoimmune coeliac disease, ACTH deficiency, dermatomyositis, Sjögren syndrome, systemic sclerosis, progressive systemic sclerosis, morphea, primary antiphospholipid syndrome, chronic idiopathic urticaria, connective tissue syndromes, necrotizing and crescentic glomerulonephritis (NCGN), systemic vasculitis, Raynaud syndrome, chronic liver disease, visceral leishmaniasis, autoimmune C1 deficiency, membrane proliferative glomerulonephritis (MPGN), prolonged coagulation time, immunodeficiency, atherosclerosis, neuronopathy, paraneoplastic pemphigus, paraneoplastic stiff man syndrome, paraneoplastic encephalomyelitis, subacute autonomic neuropathy, cancer-associated retinopathy, paraneoplastic opsoclonus myoclonus ataxia, lower motor neuron syndrome and Lambert-Eaton myasthenic syndrome.

A. Ankylosing Spondylitis

AS is a disease subset within a broader disease classification of spondyloarthropathy. Patients affected with the various subsets of spondyloarthropathy have disease etiologies that are often very different, ranging from bacterial infections to inheritance. Yet, in all subgroups, the end result of the disease process is axial arthritis. Despite the early clinically differences seen in the various patient populations, many of them end up nearly identical after a disease course of ten-to-twenty years. Recent studies suggest the mean time to clinical diagnosis of ankylosing spondylitis from disease onset of disease is 7.5 years (Khan, 1998). These same studies suggest that the spondyloarthropathies may have prevalence close to that of rheumatoid arthritis (Feldtkeller et al., 2003; Doran et al., 2003).

AS is a chronic systemic inflammatory rheumatic disorder of the axial skeleton with or without extraskeletal manifestations. Sacroiliac joints and the spine are primarily affected, but hip and shoulder joints, and less commonly peripheral joints or certain extra-articular structures such as the eye, vasculature, nervous system, and gastrointestinal system may also be involved. Its etiology is not yet fully understood (Wordsworth, 1995; Calin and Taurog, 1998). It is strongly associated with the major histocompatibility class I (MHC I) HLA-B27 allele (Calin and Taurog, 1998). AS affects individuals in the prime of their life and is feared because of its potential to cause chronic pain and irreversible damage of tendons, ligaments, joints, and bones (Brewerton et al., 1973; Brewerton et al., 1973; Schlosstein et al., 1973). AS may occur alone or in association with another form of spondyloarthropathy such as reactive arthritis, psoriasis, psoriatic arthritis, enthesitis, ulcerative colitis, irritable bowel disease, or Crohn's disease, in which case it is classified as secondary AS.

Typically, the affected sites include the discovertebral, apophyseal, costovertebral, and costotransverse joints of the spine, and the paravertebral ligamentous structures. Inflammation of the entheses, which are sites of musculotendinous and ligamentous attachment to bones, is also prominent in this disease (Calin and Taurog, 1998). The site of enthesitis is known to be infiltrated by plasma cells, lymphocytes, and polymorphonuclear cells. The inflammatory process frequently results in gradual fibrous and bony ankylosis, (Ball, 1971; Khan, 1990).

Delayed diagnosis is common because symptoms are often attributed to more common back problems. A dramatic loss of flexibility in the lumbar spine is an early sign of AS. Other common symptoms include chronic pain and stiffness in the lower back which usually starts where the lower spine is joined to the pelvis, or hip.

Although most symptoms begin in the lumbar and sacroiliac areas, they may involve the neck and upper back as well. Arthritis may also occur in the shoulder, hips and feet. Some patients have eye inflammation, and more severe cases must be observed for heart valve involvement.

The most frequent presentation is back pain, but disease can begin atypically in peripheral joints, especially in children and women, and rarely with acute iritis (anterior uveitis). Additional early symptoms and signs are diminished chest expansion from diffuse costovertebral involvement, low-grade fever, fatigue, anorexia, weight loss, and anemia. Recurrent back pain—often nocturnal and of varying intensity—is an eventual complaint, as is morning stiffness typically relieved by activity. A flexed or bent-over posture eases back pain and paraspinal muscle spasm; thus, some degree of kyphosis is common in untreated patients.

Systemic manifestations occur in ⅓ of patients. Recurrent, usually self-limited, acute iritis (anterior uveitis) rarely is protracted and severe enough to impair vision. Neurologic signs can occasionally result from compression radiculitis or sciatica, vertebral fracture or subluxation, and cauda equina syndrome (which consists of impotence, nocturnal urinary incontinence, diminished bladder and rectal sensation, and absence of ankle jerks). Cardiovascular manifestations can include aortic insufficiency, angina, pericarditis, and ECG conduction abnormalities. A rare pulmonary finding is upper lobe fibrosis, occasionally with cavitation that may be mistaken for TB and can be complicated by infection with *Aspergillus*.

AS is characterized by mild or moderate flares of active spondylitis alternating with periods of almost or totally inactive inflammation. Proper treatment in most patients results in minimal or no disability and in full, productive lives despite back stiffness. Occasionally, the course is severe and progressive, resulting in pronounced incapacitating deformities. The prognosis is bleak for patients with refractory iritis and for the rare patient with secondary amyloidosis.

The ESR and other acute-phase reactants (e.g., C-reactive protein and serum Ig levels) are mildly elevated in most patients with active AS. Tests for IgM rheumatoid factor and antinuclear antibodies are negative. A positive test for HLA-B27 is usual but not invariable and not specific (a negative test is more useful in helping to exclude AS than a positive test is in diagnosing it). This test is not necessary in patients with typical disease.

Diagnosis must be confirmed by x-ray. The earliest abnormalities (pseudo-widening from subchondral erosions, sclerosis or later narrowing) occur in the sacroiliac joints. Early changes in the spine are upper lumbar vertebral squaring and demineralization, spotty ligamentous calcification, and one or two evolving syndesmophytes. The classic bamboo spine with prominent syndesmophytes and diffuse paraspinal ligamentous calcification is not useful for early diagnosis; these changes develop in a minority of patients over an average period of 10 years.

The severity of joint involvement and the degree of systemic symptoms vary greatly from one individual to another. Early, accurate diagnosis and therapy may minimize years of pain and disability.

Joint discomfort may be relieved with drugs. Treatment plans usually address prevention, delay, or correction of the deformity and psychosocial and rehabilitation needs. For proper posture and joint motion, daily exercise and other supportive measures (e.g., postural training, therapeutic exercise) are vital to strengthen muscle groups that oppose the direction of potential deformities (i.e., strengthen the extensor rather than flexor muscle groups). Reading while lying prone and thus extending the neck may help keep the back flexible.

NSAIDs facilitate exercise and other supportive measures by suppressing articular inflammation, pain, and muscle spasm. Most NSAIDs are of proven value in AS, but tolerance and toxicity, rather than marginal differences in efficacy, dictate drug choice. Patients should be monitored and warned of potential adverse reactions. The daily dose of NSAIDs should be as low as possible, but maximum doses of a drug such as indomethacin may be needed with active disease. Drug withdrawal should be attempted only slowly, after systemic and articular signs of active disease have been suppressed for several months. Several new NSAIDs, referred to as COX-2 drugs because they inhibit cyclooxygenase-2, provide equal effectiveness to drugs that inhibit COX-1 with less chance of adverse effects on the gastric mucosa, and platelet aggregation.

Corticosteroids have limited therapeutic value; long-term use is associated with many serious adverse effects, including osteoporosis of the stiff spine. For acute iritis, topical corticosteroids (and mydriatics) usually are adequate; oral corticosteroids are rarely indicated. Intra-articular corticosteroids may be beneficial, particularly when one or two peripheral joints are more severely inflamed than others, thereby compromising exercise and rehabilitation.

Most slow-acting (remitting) drugs for RA (e.g., gold given IM) either have not been studied or are not effective for AS. Sulfasalazine may be helpful, particularly when the peripheral joints are involved. Dosage should be started at 500 mg/day and increased by 500 mg/day at 1-wk intervals to 1 g bid maintenance (see also Rheumatoid Arthritis in Ch. 50). The most common side effect is nausea, which is mainly central, but enteric-coated tablets are better tolerated. Dose reduction may help.

Narcotics, other strong analgesics, and muscle relaxants lack anti-inflammatory properties and should be prescribed only short-term as adjuncts to help control severe back pain and spasm. Radiotherapy to the spine, although effective, is recommended as a last resort because it increases the risk of acute myelogenous leukemia ten-fold.

Rehabilitation therapies are essential. Proper sleep and walking positions, coupled with abdominal and back exercises, help maintain posture. Exercises help maintain joint flexibility. Breathing exercises enhance lung capacity, and swimming provides aerobic exercise. Even with optimal treatment, some people will develop a stiff or "ankylosed" spine, but they will remain functional if this fusion occurs in an upright position. Continuing care is critical. AS is a lifelong problem, and people often fail to continue treatment, in which case permanent posture and mobility losses occur.

B. Psoratic Arthritis

Psoriasis is an inflammatory and proliferative skin disorder with a prevalence of 1.5-3%. Approximately 20% of patients with psoriasis develop a characteristic form of arthritis that has several patterns (Gladman, 1992; Jones et al., 1994; Gladman et al., 1995). Some individuals present with joint symptoms first but in the majority, skin psoriasis presents first. About one-third of patients have simultaneous exacerbations of their skin and joint disease (Gladman et al., 1987) and there is a topographic relationship between nail and distal interphalangeal joint disease (Jones et 1994; Wright, 1956). Although the inflammatory processes which link skin, nail and joint disease remain elusive, an immune-mediated pathology is implicated.

Psoriatic arthritis (PsA) is a chronic inflammatory arthropathy characterized by the association of arthritis and psoriasis and was recognized as a clinical entity distinct from rheumatoid arthritis (RA) in 1964 (Blumberg et al., 1964). Subsequent studies have revealed that PsA shares a number of genetic, pathogenic and clinical features with other spondyloarthropathies (SpAs), a group of diseases that comprise ankylosing spondylitis, reactive arthritis and enteropathic arthritis (Wright, 1979). The notion that PsA belongs to the SpA group has recently gained further support from imaging studies demonstrating widespread enthesitis in the, including PsA but not RA (McGonagle et al., 1999; McGonagle al., 1998). More specifically, enthesitis has been postulated to be one of the earliest events occurring in the SpAs, leading to bone remodeling and ankylosis in the spine, as well as to articular synovitis when the inflamed entheses are close to peripheral joints. However, the link between enthesitis and the clinical manifestations in PsA remains largely unclear, as PsA can present with fairly heterogeneous patterns of joint involvement with variable degrees of severity (Marsal et al., 1999; Salvarani et al., 1998). Thus, other factors must be posited to account for the multifarious features of PsA, only a few of which (such as the expression of the HLA-B27 molecule, which is strongly associated with axial disease) have been identified. As a consequence, it remains difficult to map the disease manifestations to specific pathogenic mechanisms, which means that the treatment of this condition remains largely empirical.

Family studies have suggested a genetic contribution to the development of PsA (Moll & Wright, 1973). Other chronic inflammatory forms of arthritis, such as ankylosing spondylitis and rheumatoid arthritis, are thought to have a complex genetic basis. However, the genetic component of PsA has been difficult to assess for several reasons. There is strong evidence for a genetic predisposition to psoriasis alone that may mask the genetic factors that are important for the development of PsA. Although most would accept PsA as a distinct disease entity, at times there is a phenotypic overlap with rheumatoid arthritis and ankylosing spondylitis. Also, PsA itself is not a homogeneous condition and various subgroups have been proposed. Although not all these confounding factors were overcome in the present study, we concentrated on investigating candidate genes in three broad categories of patients with PsA that cover the disease spectrum.

Polymorphisms in the promoter region of the TNFA region are of considerable interest as they may influence levels of TNF-α secretion (Jacob et al., 1990; Bendzen et al., 1988). Increased amounts of TNF-α have been reported in both psoriatic skin (Ettehadi et al., 1994) and synovial fluid (Partsch et al., 1997).

Recent trials have shown a positive benefit of anti-TNF treatment in both PsA (Mease et al., 2000) and ankylosing spondylitis (Brandt et al., 2000). Furthermore, the locus for TNF-α resides within the class III region of the MHC and thus may provide tighter associations with PsA than those provided by flanking class I and class II regions. There were relatively weak associations with the TNFA alleles in our total PsA group. The uncommon TNFA-238A allele was increased in frequency in the group with peripheral polyarthritis and absent in those patients with spondylitis, although this finding may be explained by linkage disequilibrium with HLA-Cw*0602. Whether there are functional consequences associated with polymorphisms at the TNFA-238 allele is unclear (Pociot et al., 1995). Nonetheless, it is possible that the pattern of arthritis that develops in patients with psoriasis may be linked directly or indirectly to this particular allele.

Hohler et al. (1997) found an increase in the frequency of the TNFA-238A allele in patients with PsA as well as in juvenile onset psoriasis. The association of TWA-238A with both juvenile onset psoriasis and PsA was stronger than that with HLA-Cw6. Similarly, in our study, there were strong associations between juvenile onset psoriasis and both HLA-Cw*0602 and TiVFA-238A, although neither allele had any relationship to the age of onset of arthritis. In our study, all patients with PsA who had at least one TNFA-238A allele were HLA-Cw6-positive, emphasizing the close linkage between these alleles in PsA. However, in contrast to the study by Hohler et al. (1997), and explainable by close linkage to HLA-Cw*0602, the TNFA-238A allele was only increased in patients with peripheral arthritis. It is also of interest that, in a separate study of ankylosing spondylitis, the same group found the uncommon TWA-308A and -238A alleles to have a protective effect on the development of spondylitis (Hohler et al., 1998).

C. Reactive Arthritis

In reactive arthritis (ReA) the mechanism of joint damage is unclear, but it is likely that cytokines play critical roles. A more prevalent Th1 profile high levels of interferon gamma (IFN-γ) and low levels of interleukin 4 (IL-4) has been reported (Lahesmaa et al., 1992; Schlaak et al., 1992; Simon et al., 1993; Schlaak et al., 1996; Kotake et al., 1999; Ribbens et al., 2000), but several studies have shown relative predominance of IL-4 and IL-10 and relative lack of IFN-γ and tumor necrosis factor alpha (TNF-α) in the synovial membrane (Simon et al., 1994; Yin et al., 1999) and fluid (SF) (Yin et al., 1999; Yin et al., 1997) of reactive arthritis patients compared with rheumatoid arthritis (RA) patients. A lower level of TNF-α secretion in reactive arthritis than in RA patients has also been reported after ex vivo stimulation of peripheral blood mononuclear cells (PBMC) (Braun et al., 1999).

It has been argued that clearance of reactive arthritis-associated bacteria requires the production of appropriate levels of IFN-γ and TNF-α, while IL-10 acts by suppressing these responses (Autenrieth et al., 1994; Sieper & Braun, 1995). IL-10 is a regulatory cytokine that inhibits the synthesis of IL-12 and TNF-γ by activated macrophages (de Waal et al., 1991; Hart et al., 1995; Chomarat et al., 1995) and of IFN-γ by T cells (Macatonia et al., 1993).

D. Enteropathic Arthritis

Enteropathic arthritis (EA) occurs in combination with inflammatory bowel diseases (IBD) such as Crohn's disease or ulcerative colitis. It also can affect the spine and sacroiliac joints. Enteropathic arthritis involves the peripheral joints, usually in the lower extremities such as the knees or ankles. It commonly involves only a few or a limited number of joints and may closely follow the bowel condition. This occurs in approximately 11% of patients with ulcerative colitis and 21% of those with Crohn's disease. The synovitis is generally self-limited and non-deforming.

Enteropathic arthropathies comprise a collection of rheumatologic conditions that share a link to GI pathology. These conditions include reactive (i.e., infection-related) arthritis due to bacteria (e.g., *Shigella, Salmonella, campylobacter, Yersinia* species, *Clostridium difficile*), parasites (e.g., *Strongyloides stercoralis, Taenia saginata, Giardia lamblia, Ascaris lumbricoides, Cryptosporidium* species), and spondyloarthropathies associated with inflammatory bowel disease (IBD). Other conditions and disorders include intestinal bypass (jejunoileal), arthritis, celiac disease, Whipple disease, and collagenous colitis.

The precise causes of enteropathic arthropathies are unknown. Inflammation of the GI tract may increase permeability, resulting in absorption of antigenic material, including bacterial antigens. These arthrogenic antigens may then localize in musculoskeletal tissues (including entheses and synovium), thus eliciting an inflammatory response. Alternatively, an autoimmune response may be induced through molecular mimicry, in which the host's immune response to these antigens cross-reacts with self-antigens in synovium.

Of particular interest is the strong association between reactive arthritis and HLA-B27, an HLA class 1 molecule. A potentially arthrogenic, bacterially derived antigen peptide could fit in the antigen-presenting groove of the B27 molecule, resulting in a CD8+ T-cell response. HLA-B27 transgenic rats develop features of enteropathic arthropathy with arthritis and gut inflammation.

E. Ulcerative Colitis

Ulcerative colitis is a disease that causes inflammation and sores, called ulcers, in the lining of the large intestine. The inflammation usually occurs in the rectum and lower part of the colon, but it may affect the entire colon. Ulcerative colitis rarely affects the small intestine except for the end section, called the terminal ileum. Ulcerative colitis may also be called colitis or proctitis. The inflammation makes the colon empty frequently, causing diarrhea. Ulcers form in places where the inflammation has killed the cells lining the colon; the ulcers bleed and produce pus.

Ulcerative colitis is an inflammatory bowel disease (IBD), the general name for diseases that cause inflammation in the small intestine and colon. Ulcerative colitis can be difficult to diagnose because its symptoms are similar to other intestinal disorders and to another type of IBD, Crohn's disease. Crohn's disease differs from ulcerative colitis because it causes inflammation deeper within the intestinal wall. Also, Crohn's disease usually occurs in the small intestine, although it can also occur in the mouth, esophagus, stomach, duodenum, large intestine, appendix, and anus.

Ulcerative colitis may occur in people of any age, but most often it starts between ages 15 and 30, or less frequently between ages 50 and 70. Children and adolescents sometimes develop the disease. Ulcerative colitis affects men and women equally and appears to run in some families. Theories about what causes ulcerative colitis abound, but none have been proven. The most popular theory is that the body's immune system reacts to a virus or a bacterium by causing ongoing inflammation in the intestinal wall. People with ulcerative colitis have abnormalities of the immune system, but doctors do not know whether these abnormalities are a cause or a result of the disease. Ulcerative colitis is not caused by emotional distress or sensitivity to certain foods or food products, but these factors may trigger symptoms in some people.

The most common symptoms of ulcerative colitis are abdominal pain and bloody diarrhea. Patients also may experience fatigue, weight loss, loss of appetite, rectal bleeding, and loss of body fluids and nutrients. About half of patients have mild symptoms. Others suffer frequent fever, bloody diarrhea, nausea, and severe abdominal cramps. Ulcerative colitis may also cause problems such as arthritis, inflammation of the eye, liver disease (hepatitis, cirrhosis, and primary sclerosing cholangitis), osteoporosis, skin rashes, and anemia. No one knows for sure why problems occur outside the colon. Scientists think these complications may occur when the immune system triggers inflammation in other parts of the body. Some of these problems go away when the colitis is treated.

A thorough physical exam and a series of tests may be required to diagnose ulcerative colitis. Blood tests may be done to check for anemia, which could indicate bleeding in the colon or rectum. Blood tests may also uncover a high white blood cell count, which is a sign of inflammation somewhere in the body. By testing a stool sample, the doctor can detect bleeding or infection in the colon or rectum. The doctor may do a colonoscopy or sigmoidoscopy. For either test, the doctor inserts an endoscope—a long, flexible, lighted tube connected to a computer and TV monitor—into the anus to see the inside of the colon and rectum. The doctor will be able to see any inflammation, bleeding, or ulcers on the colon wall. During the exam, the doctor may do a biopsy, which involves taking a sample of tissue from the lining of the colon to view with a microscope. A barium enema x ray of the colon may also be required. This procedure involves filling the colon with barium, a chalky white solution. The barium shows up white on x-ray film, allowing the doctor a clear view of the colon, including any ulcers or other abnormalities that might be there.

Treatment for ulcerative colitis depends on the seriousness of the disease. Most people are treated with medication. In severe cases, a patient may need surgery to remove the diseased colon. Surgery is the only cure for ulcerative colitis. Some people whose symptoms are triggered by certain foods are able to control the symptoms by avoiding foods that upset their intestines, like highly seasoned foods, raw fruits and vegetables, or milk sugar (lactose). Each person may experience ulcerative colitis differently, so treatment is adjusted for each individual. Emotional and psychological support is important. Some people have remissions—periods when the symptoms go away—that last for months or even years. However, most patients' symptoms eventually return. This changing pattern of the disease means one cannot always tell when a treatment has helped. Some people with ulcerative colitis may need medical care for some time, with regular doctor visits to monitor the condition.

The goal of therapy is to induce and maintain remission, and to improve the quality of life for people with ulcerative colitis. Several types of drugs are available:

Aminosalicylates—drugs that contain 5-aminosalicyclic acid (5-ASA), help control inflammation. Sulfasalazine is a combination of sulfapyridine and 5-ASA and is used to induce and maintain remission. The sulfapyridine component carries the anti-inflammatory 5-ASA to the intestine. However, sulfapyridine may lead to side effects such as include nausea, vomiting, heartburn, diarrhea, and headache. Other 5-ASA agents such as olsalazine, mesalamine, and balsalazide, have a different carrier, offer fewer side effects, and may be used by people who cannot take sulfasalazine. 5-ASAs are given orally, through an enema, or in a suppository, depending on the location of the inflammation in the colon. Most people with mild or moderate ulcerative colitis are treated with this group of drugs first.

Corticosteroids—such as prednisone and hydrocortisone also reduce inflammation. They may be used by people who have moderate to severe ulcerative colitis or who do not respond to 5-ASA drugs. Corticosteroids, also known as steroids, can be given orally, intravenously, through an enema, or in a suppository, depending on the location of the inflammation. These drugs can cause side effects such as weight gain, acne, facial hair, hypertension, mood swings, and an increased risk of infection. For this reason, they are not recommended for long-term use.

Immunomodulators—such as azathioprine and 6-mercapto-purine (6-MP) reduce inflammation by affecting the immune system. They are used for patients who have not responded to 5-ASAs or corticosteroids or who are dependent on corticosteroids. However, immunomodulators are slow-acting and may take up to 6 months before the full benefit is seen. Patients taking these drugs are monitored for complications including pancreatitis and hepatitis, a reduced white blood cell count, and an increased risk of infection. Cyclosporine A may be used with 6-MP or azathioprine to treat active, severe ulcerative colitis in people who do not respond to intravenous corticosteroids.

Other drugs may be given to relax the patient or to relieve pain, diarrhea, or infection.

Occasionally, symptoms are severe enough that the person must be hospitalized. For example, a person may have severe bleeding or severe diarrhea that causes dehydration. In such cases the doctor will try to stop diarrhea and loss of blood, fluids, and mineral salts. The patient may need a special diet, feeding through a vein, medications, or sometimes surgery.

About 25-40% of ulcerative colitis patients must eventually have their colons removed because of massive bleeding, severe illness, rupture of the colon, or risk of cancer. Sometimes the doctor will recommend removing the colon if medical treatment fails or if the side effects of corticosteroids or other drugs threaten the patient's health. Surgery to remove the colon and rectum, known as proctocolectomy, is followed by one of the following:

Ileostomy, in which the surgeon creates a small opening in the abdomen, called a stoma, and attaches the end of the small intestine, called the ileum, to it. Waste will travel through the small intestine and exit the body through the stoma. The stoma is about the size of a quarter and is usually located in the lower right part of the abdomen near the beltline. A pouch is worn over the opening to collect waste, and the patient empties the pouch as needed.

Ileoanal anastomosis, or pull-through operation, which allows the patient to have normal bowel movements because it preserves part of the anus. In this operation, the surgeon removes the diseased part of the colon and the inside of the rectum, leaving the outer muscles of the rectum. The surgeon then attaches the ileum to the inside of the rectum and the anus, creating a pouch. Waste is stored in the pouch and passed through the anus in the usual manner. Bowel movements may be more frequent and watery than before the procedure. Inflammation of the pouch (pouchitis) is a possible complication.

Not every operation is appropriate for every person. Which surgery to have depends on the severity of the disease and the patient's needs, expectations, and lifestyle. People faced with this decision should get as much information as possible by talking to their doctors, to nurses who work with colon surgery patients (enterostomal therapists), and to other colon surgery patients. Patient advocacy organizations can direct people to support groups and other information resources.

Most people with ulcerative colitis will never need to have surgery. If surgery does become necessary, however, some people find comfort in knowing that after the surgery, the colitis is cured and most people go on to live normal, active lives.

F. Crohn's Disease

Another disorder for which immunosuppression has been tried is Crohn's disease. Crohn's disease symptoms include intestinal inflammation and the development of intestinal stenosis and fistulas; neuropathy often accompanies these symptoms. Anti-inflammatory drugs, such as 5-aminosalicylates (e.g., mesalamine) or corticosteroids, are typically prescribed, but are not always effective (reviewed in Botoman et al., 1998). Immunosuppression with cyclosporine is sometimes beneficial for patients resistant to or intolerant of corticosteroids (Brynskov et al., 1989).

Nevertheless, surgical correction is eventually required in 90% of patients; 50% undergo colonic resection (Leiper et al., 1998; Makowiec et al., 1998). The recurrence rate after surgery is high, with 50% requiring further surgery within 5 years (Leiper et al., 1998; Besnard et al., 1998).

One hypothesis for the etiology of Crohn's disease is that a failure of the intestinal mucosal barrier, possibly resulting from genetic susceptibilities and environmental factors (e.g., smoking), exposes the immune system to antigens from the intestinal lumen including bacterial and food antigens (e.g., Soderholm et al., 1999; Hollander et al., 1986; Hollander, 1992). Another hypothesis is that persistent intestinal infection by pathogens such as *Mycobacterium paratuberculosis, Listeria monocytogenes*, abnormal *Escherichia coli*, or paramyxovirus, stimulates the immune response; or alternatively, symptoms result from a dysregulated immune response to ubiquitous antigens, such as normal intestinal microflora and the metabolites and toxins they produce (Sailor, 1997). The presence of IgA and IgG anti-*Saccharomyces* cerevisiae antibodies (ASCA) in the serum was found to be highly diagnostic of pediatric Crohn's disease (Ruemmele et al., 1998; Hoffenberg et al., 1999).

In Crohn's disease, a dysregulated immune response is skewed toward cell-mediated immunopathology (Murch, 1998). But immunosuppressive drugs, such as cyclosporine, tacrolimus, and mesalamine have been used to treat corticosteroid-resistant cases of Crohn's disease with mixed success (Brynskov et al., 1989; Fellerman et al., 1998).

Recent efforts to develop diagnostic and treatment tools against Crohn's disease have focused on the central role of cytokines (Schreiber, 1998; van Hogezand & Verspaget, 1998). Cytokines are small secreted proteins or factors (5 to 20 kD) that have specific effects on cell-to-cell interactions, intercellular communication, or the behavior of other cells. Cytokines are produced by lymphocytes, especially $T_H 1$ and $T_H 2$ lymphocytes, monocytes, intestinal macrophages, granulocytes, epithelial cells, and fibroblasts (reviewed in Rogler &. Andus, 1998; Galley & Webster, 1996). Some cytokines are pro-inflammatory (e.g., TNF-$\alpha$, IL-1($\alpha$ and $\beta$), IL-6, IL-8, IL-12, or leukemia inhibitory factor, or LIF); others are anti-inflammatory (e.g., IL-1 receptor antagonist, IL-4, IL-10, IL-11, and TGF-$\beta$). However, there may be overlap and functional redundancy in their effects under certain inflammatory conditions.

In active cases of Crohn's disease, elevated concentrations of TNF-$\alpha$ and IL-6 are secreted into the blood circulation, and TNF-$\alpha$, IL-1, IL-6, and IL-8 are produced in excess locally by mucosal cells (id.; Funakoshi et al., 1998). These cytokines can have far-ranging effects on physiological systems including bone development, hematopoiesis, and liver, thyroid, and neuropsychiatric function. Also, an imbalance of the IL-1$\beta$/IL-1ra ratio, in favor of pro-inflammatory IL-1$\beta$, has been observed in patients with Crohn's disease (Rogler & Andus, 1998; Saiki et al., 1998; Dionne et al., 1998; but see Kuboyama, 1998). One study suggested that cytokine profiles in stool samples could be a useful diagnostic tool for Crohn's disease (Saiki et al., 1998).

Treatments that have been proposed for Crohn's disease include the use of various cytokine antagonists (e.g., IL-1 ra), inhibitors (e.g., of IL-1$\beta$ converting enzyme and antioxidants) and anti-cytokine antibodies (Rogler and Andus, 1998; van Hogezand & Verspaget, 1998; Reimund et al., 1998; Lugering et al., 1998; McAlindon et al., 1998). In particular, monoclonal antibodies against TNF-$\alpha$ have been tried with some success in the treatment of Crohn's disease (Targan et al., 1997; Stack et al., 1997; van Dullemen et al., 1995).

Another approach to the treatment of Crohn's disease has focused on at least partially eradicating the bacterial community that may be triggering the inflammatory response and replacing it with a non-pathogenic community. For example, U.S. Pat. No. 5,599,795 discloses a method for the prevention and treatment of Crohn's disease in human patients. Their method was directed to sterilizing the intestinal tract with at least one antibiotic and at least one anti-fungal agent to kill off the existing flora and replacing them with different, select, well-characterized bacteria taken from normal humans. Borody taught a method of treating Crohn's disease by at least partial removal of the existing intestinal microflora by lavage and replacement with a new bacterial community introduced by fecal inoculum from a disease-screened human donor or by a composition comprising *Bacteroides* and *Escherichia coli* species. (U.S. Pat. No. 5,443,826). However, there has been no known cause of Crohn's disease to which diagnosis and/or treatment could be directed.

G. Rheumatoid Arthritis

The exact etiology of RA remains unknown, but the first signs of joint disease appear in the synovial lining layer, with proliferation of synovial fibroblasts and their attachment to the articular surface at the joint margin (Lipsky, 1998). Subsequently, macrophages, T cells and other inflammatory cells are recruited into the joint, where they produce a number of mediators, including the cytokines interleukin-1 (IL-1), which contributes to the chronic sequelae leading to bone and cartilage destruction, and tumour necrosis factor (TNF-α), which plays a role in inflammation (Dinarello, 1998; Arend & Dayer, 1995; van den Berg, 2001). The concentration of IL-1 in plasma is significantly higher in patients with RA than in healthy individuals and, notably, plasma IL-1 levels correlate with RA disease activity (Eastgate et al., 1988). Moreover, synovial fluid levels of IL-1 are correlated with various radiographic and histologic features of RA (Kahle et al., 1992; Rooney et al, 1990).

In normal joints, the effects of these and other proinflammatory cytokines are balanced by a variety of anti-inflammatory cytokines and regulatory factors (Burger & Dayer, 1995). The significance of this cytokine balance is illustrated in juvenile RA patients, who have cyclical increases in fever throughout the day (Prieur et al., 1987). After each peak in fever, a factor that blocks the effects of IL-1 is found in serum and urine. This factor has been isolated, cloned and identified as IL-1 receptor antagonist (IL-1ra), a member of the IL-1 gene family (Hannum et al., 1990). IL-1ra, as its name indicates, is a natural receptor antagonist that competes with IL-1 for binding to type I IL-1 receptors and, as a result, blocks the effects of IL-1 (Arend et al., 1998). A 10- to 100-fold excess of IL-1ra may be needed to block IL-1 effectively; however, synovial cells isolated from patients with RA do not appear to produce enough IL-1ra to counteract the effects of IL-1 (Firestein et al., 1994; Fujikawa et al., 1995).

H. Systemic Lupus Erythematosus

There has also been no known cause for autoimmune diseases such as systemic lupus erythematosus. Systemic lupus erythematosus (SLE) is an autoimmune rheumatic disease characterized by deposition in tissues of autoantibodies and immune complexes leading to tissue injury (Kotzin, 1996). In contrast to autoimmune diseases such as MS and type 1 diabetes mellitus, SLE potentially involves multiple organ systems directly, and its clinical manifestations are diverse and variable (reviewed by Kotzin & O'Dell, 1995). For example, some patients may demonstrate primarily skin rash and joint pain, show spontaneous remissions, and require little medication. At the other end of the spectrum are patients who demonstrate severe and progressive kidney involvement that requires therapy with high doses of steroids and cytotoxic drugs such as cyclophosphamide (Kotzin, 1996).

The serological hallmark of SLE, and the primary diagnostic test available, is elevated serum levels of IgG antibodies to constituents of the cell nucleus, such as double-stranded DNA (dsDNA), single-stranded DNA (ss-DNA), and chromatin. Among these autoantibodies, IgG anti-dsDNA antibodies play a major role in the development of lupus glomerulonephritis (G N) (Hahn & Tsao, 1993; Ohnishi et al., 1994). Glomerulonephritis is a serious condition in which the capillary walls of the kidney's blood purifying glomeruli become thickened by accretions on the epithelial side of glomerular basement membranes. The disease is often chronic and progressive and may lead to eventual renal failure.

The mechanisms by which autoantibodies are induced in these autoimmune diseases remains unclear. As there has been no known cause of SLE, to which diagnosis and/or treatment could be directed, treatment has been directed to suppressing immune responses, for example with macrolide antibiotics, rather than to an underlying cause. (e.g., U.S. Pat. No. 4,843,092).

I. Irritable Bowel Syndrome

Irritable bowel syndrome (IBS) is a functional disorder characterized by abdominal pain and altered bowel habits. This syndrome may begin in young adulthood and can be associated with significant disability. This syndrome is not a homogeneous disorder. Rather, subtypes of IBS have been described on the basis of the predominant symptom—diarrhea, constipation, or pain. In the absence of "alarm" symptoms, such as fever, weight loss, and gastrointestinal bleeding, a limited workup is needed. Once a diagnosis of IBS is made, an integrated treatment approach can effectively reduce the severity of symptoms. IBS is a common disorder, although its prevalence rates have varied. In general, IBS affects about 15% of US adults and occurs about three times more often in women than in men (Jailwala et al., 2000).

IBS accounts for between 2.4 million and 3.5 million visits to physicians each year. It not only is the most common condition seen by gastroenterologists but also is one of the most common gastrointestinal conditions seen by primary care physicians (Everhart et al., 1991; Sandler, 1990).

IBS is also a costly disorder. Compared with persons who do not have bowel symptoms, persons with IBS miss three times as many workdays and are more likely to report being too sick to work (Drossman et al., 1993; Drossman et al., 1997). Moreover, those with IBS incur hundreds of dollars more in medical charges than persons without bowel disorders (Talley et al., 1995).

No specific abnormality accounts for the exacerbations and remissions of abdominal pain and altered bowel habits experienced by patients with IBS. The evolving theory of IBS suggests dysregulation at multiple levels of the brain-gut axis. Dysmotility, visceral hypersensitivity, abnormal modulation of the central nervous system (CNS), and infection have all been implicated. In addition, psychosocial factors play an important modifying role. Abnormal intestinal motility has long been considered a factor in the pathogenesis of IBS. Transit time through the small intestine after a meal has been shown to be shorter in patients with diarrhea-predominant IBS than in patients who have the constipation-predominant or pain-predominant subtype (Cann et al., 1983).

In studies of the small intestine during fasting, the presence of both discrete, clustered contractions and prolonged, propagated contractions has been reported in patients with IBS (Kellow & Phillips, 1987). They also experience pain with irregular contractions more often than healthy persons (Kellow & Phillips, 1987; Horwitz & Fisher, 2001)

These motility findings do not account for the entire symptom complex in patients with IBS; in fact, most of these patients do not have demonstrable abnormalities (Rothstein, 2000). Patients with IBS have increased sensitivity to visceral pain. Studies involving balloon distention of the rectosigmoid colon have shown that patients with IBS experience pain and bloating at pressures and volumes much lower than control subjects (Whitehead et al., 1990). These patients maintain normal perception of somatic stimuli.

Multiple theories have been proposed to explain this phenomenon. For example, receptors in the viscera may have increased sensitivity in response to distention or intraluminal contents. Neurons in the dorsal horn of the spinal cord may have increased excitability. In addition, alteration in CNS processing of sensations may be involved (Drossman et al., 1997). Functional magnetic resonance imaging studies have recently shown that compared with control subjects, patients with IBS have increased activation of the anterior cingulate cortex, an important pain center, in response to a painful rectal stimulus (Mertz et al., 2000).

Increasingly, evidence suggests a relationship between infectious enteritis and subsequent development of IBS. Inflammatory cytokines may play a role. In a survey of patients with a history of confirmed bacterial gastroenteritis (Neal et al., 1997), 25% reported persistent alteration of bowel habits. Persistence of symptoms may be due to psychologic stress at the time of acute infection (Gwee et al., 1999).

Recent data suggest that bacterial overgrowth in the small intestine may have a role in IBS symptoms. In one study (Pimentel et al., 2000), 157 (78%) of 202 IBS patients referred for hydrogen breath testing had test findings that were positive for bacterial overgrowth. Of the 47 subjects who had follow-up testing, 25 (53%) reported improvement in symptoms (i.e., abdominal pain and diarrhea) with antibiotic treatment.

IBS may present with a range of symptoms. However, abdominal pain and altered bowel habits remain the primary features. Abdominal discomfort is often described as crampy in nature and located in the left lower quadrant, although the severity and location can differ greatly. Patients may report diarrhea, constipation, or alternating episodes of diarrhea and constipation. Diarrheal symptoms are typically described as small-volume, loose stools, and stool is sometimes accompanied by mucus discharge. Patients also may report bloating, fecal urgency, incomplete evacuation, and abdominal distention. Upper gastrointestinal symptoms, such as gastroesophageal reflux, dyspepsia, or nausea, may also be present (Lynn & Friedman, 1993).

Persistence of symptoms is not an indication for further testing; it is a characteristic of IBS and is itself an expected symptom of the syndrome. More extensive diagnostic evaluation is indicated in patients whose symptoms are worsening or changing. Indications for further testing also include presence of alarm symptoms, onset of symptoms after age 50, and a family history of colon cancer. Tests may include colonoscopy, computed tomography of the abdomen and pelvis, and barium studies of the small or large intestine.

J. Juvenile Rheumatoid Arthritis

Juvenile rheumatoid arthritis (JRA), a term for the most prevalent form of arthritis in children, is applied to a family of illnesses characterized by chronic inflammation and hypertrophy of the synovial membranes. The term overlaps, but is not completely synonymous, with the family of illnesses referred to as juvenile chronic arthritis and/or juvenile idiopathic arthritis in Europe.

Jarvis (1998) and others (Arend, 2001) have proposed that the pathogenesis of rheumatoid disease in adults and children involves complex interactions between innate and adaptive immunity. This complexity lies at the core of the difficulty of unraveling disease pathogenesis.

Both innate and adaptive immune systems use multiple cell types, a vast array of cell surface and secreted proteins, and interconnected networks of positive and negative feedback (Lo et al., 1999). Furthermore, while separable in thought, the innate and adaptive wings of the immune system are functionally intersected (Fearon & Locksley, 1996), and pathologic events occurring at these intersecting points are likely to be highly relevant to our understanding of pathogenesis of adult and childhood forms of chronic arthritis (Warrington, et al., 2001).

Polyarticular JRA is a distinct clinical subtype characterized by inflammation and synovial proliferation in multiple joints (four or more), including the small joints of the hands (Jarvis, 2002). This subtype of JRA may be severe, because of both its multiple joint involvement and its capacity to progress rapidly over time. Although clinically distinct, polyarticular JRA is not homogeneous, and patients vary in disease manifestations, age of onset, prognosis, and therapeutic response. These differences very likely reflect a spectrum of variation in the nature of the immune and inflammatory attack that can occur in this disease (Jarvis, 1998).

K. Sjogren's Syndrome

Primary Sjögren's syndrome (SS) is a chronic, slowly progressive, systemic autoimmune disease, which affects predominantly middle-aged women (female-to-male ratio 9:1), although it can be seen in all ages including childhood (Jonsson et al., 2002). It is characterized by lymphocytic infiltration and destruction of the exocrine glands, which are infiltrated by mononuclear cells including CD4+, CD8+ lymphocytes and B-cells (Jonsson et al., 2002). In addition, extraglandular (systemic) manifestations are seen in one-third of patients (Jonsson oat, 2001).

The glandular lymphocytic infiltration is a progressive feature (Jonsson et al., 1993), which, when extensive, may replace large portions of the organs. Interestingly, the glandular infiltrates in some patients closely resemble ectopic lymphoid microstructures in the salivary glands (denoted as ectopic germinal centers) (Salomonsson et al., 2002; Xanthou & Polihronis, 2001). In SS, ectopic GCs are defined as T and B cell aggregates of proliferating cells with a network of follicular dendritic cells and activated endothelial cells. These GC-like structures formed within the target tissue also portray functional properties with production of autoantibodies (anti-Ro/SSA and anti-La/SSB) (Salomonsson &, Jonsson, 2003).

In other systemic autoimmune diseases, such as RA, factors critical for ectopic GCs have been identified. Rheumatoid synovial tissues with GCs were shown to produce chemokines CXCL13, CCL21 and lymphotoxin (LT)-β (detected on follicular center and mantle zone B cells). Multivariate regression analysis of these analytes identified CXCL13 and LT-β as the solitary cytokines predicting GCs in rheumatoid synovitis (Weyand & Goronzy, 2003). Recently CXCL13 and CXCR5 in salivary glands has been shown to play an essential role in the inflammatory process by recruiting B and T cells, therefore contributing to lymphoid neogenesis and ectopic GC formation in SS (Salomonsson & Larsson, 2002).

L. Early Arthritis

The clinical presentation of different inflammatory arthropathies is similar early in the course of disease. As a result, it is often difficult to distinguish patients who are at risk of developing the severe and persistent synovitis that leads to erosive joint damage from those whose arthritis is more self-limited. Such distinction is critical in order to target therapy appropriately, treating aggressively those with erosive disease and avoiding unnecessary toxicity in patients with more self-limited disease. Current clinical criteria for diagnosing erosive arthropathies such as rheumatoid arthritis (RA) are less effective in early disease and traditional markers of disease activity such as joint counts and acute phase response do not adequately identify patients likely to have poor outcomes (Harrison & Symmons et al., 1998). Parameters reflective of the pathologic events occurring in the synovium are most likely to be of significant prognostic value.

Recent efforts to identify predictors of poor outcome in early inflammatory arthritis have identified the presence of RA specific autoantibodies, in particular antibodies towards citrullinated peptides, to be associated with erosive and persistent disease in early inflammatory arthritis cohorts. On the basis of this, a cyclical citrullinated peptide (CCP) has been developed to assist in the identification of anti-CCP antibodies in patient sera. Using this approach, the presence of anti-CCP antibodies has been shown to be specific and sensitive for RA, can distinguish RA from other arthropathies, and can potentially predict persistent, erosive synovitis before these outcomes become clinically manifest (Schellekens et al., 2000). Importantly, anti-CCP antibodies are often detectable in sera many years prior to clinical symptoms suggesting that they may be reflective of subclinical immune events (Nielen et al., 2004; Rantapaa-Dahlqvist et al., 2003).

The clinical presentation of different inflammatory arthropathies is similar early in the course of disease. As a result, it is often difficult to distinguish patients who are at risk of developing the severe and persistent synovitis that leads to erosive joint damage from those whose arthritis is more self-limited. Such distinction is critical in order to target therapy appropriately, treating aggressively those with erosive disease and avoiding unnecessary toxicity in patients with more self-limited disease. Current clinical criteria for diagnosing erosive arthropathies such as rheumatoid arthritis (RA) are less effective in early disease and traditional markers of disease activity such as joint counts and acute phase response do not adequately identify patients likely to have poor outcomes (Harrison et al., 1998). Parameters reflective of the pathologic events occurring in the synovium are most likely to be of significant prognostic value.

Recent efforts to identify predictors of poor outcome in early inflammatory arthritis have identified the presence of RA specific autoantibodies, in particular antibodies towards citrullinated peptides, to be associated with erosive and persistent disease in early inflammatory arthritis cohorts. On the basis of this, a cyclical citrullinated peptide (CCP) has been developed to assist in the identification of anti-CCP antibodies in patient sera. Using this approach, the presence of anti-CCP antibodies has been shown to be specific and sensitive for RA, can distinguish RA from other arthropathies, and can potentially predict persistent, erosive synovitis before these outcomes become clinically manifest. Importantly, anti-CCP antibodies are often detectable in sera many years prior to clinical symptoms suggesting that they may be reflective of subclinical immune events (Nielen et al., 2004; Rantapaa-Dahlqvist et al., 2003).

M. Psoriasis

Psoriasis is a chronic skin disease of scaling and inflammation that affects 2 to 2.6 percent of the United States population, or between 5.8 and 7.5 million people. Although the disease occurs in all age groups, it primarily affects adults. It appears about equally in males and females. Psoriasis occurs when skin cells quickly rise from their origin below the surface of the skin and pile up on the surface before they have a chance to mature. Usually this movement (also called turnover) takes about a month, but in psoriasis it may occur in only a few days. In its typical form, psoriasis results in patches of thick, red (inflamed) skin covered with silvery scales. These patches, which are sometimes referred to as plaques, usually itch or feel sore. They most often occur on the elbows, knees, other parts of the legs, scalp, lower back, face, palms, and soles of the feet, but they can occur on skin anywhere on the body. The disease may also affect the fingernails, the toenails, and the soft tissues of the genitals and inside the mouth. While it is not unusual for the skin around affected joints to crack, approximately 1 million people with psoriasis experience joint inflammation that produces symptoms of arthritis. This condition is called psoriatic arthritis.

Psoriasis is a skin disorder driven by the immune system, especially involving a type of white blood cell called a T cell. Normally, T cells help protect the body against infection and disease. In the case of psoriasis, T cells are put into action by mistake and become so active that they trigger other immune responses, which lead to inflammation and to rapid turnover of skin cells. In about one-third of the cases, there is a family history of psoriasis. Researchers have studied a large number of families affected by psoriasis and identified genes linked to the disease. People with psoriasis may notice that there are times when their skin worsens, then improves. Conditions that may cause flareups include infections, stress, and changes in climate that dry the skin. Also, certain medicines, including lithium and betablockers, which are prescribed for high blood pressure, may trigger an outbreak or worsen the disease.

N. Multiple Sclerosis

Multiple sclerosis (abbreviated MS, also known as disseminated sclerosis or encephalomyelitis disseminata) is an autoimmune condition in which the immune system attacks the central nervous system, leading to demyelination. Disease onset usually occurs in young adults, and it is more common in females. It has a prevalence that ranges between 2 and 150 per 100,000. MS was first described in 1868 by Jean-Martin Charcot.

MS affects the ability of nerve cells in the brain and spinal cord to communicate with each other. Nerve cells communicate by sending electrical signals called action potentials down long fibers called axons, which are wrapped in an insulating substance called myelin. In MS, the body's own immune system attacks and damages the myelin. When myelin is lost, the axons can no longer effectively conduct signals. The name multiple sclerosis refers to scars (scleroses—better known as plaques or lesions) in the white matter of the brain and spinal cord, which is mainly composed of myelin. Although much is known about the mechanisms involved in the disease process, the cause remains unknown. Theories include genetics or infections. Different environmental risk factors have also been found.

Almost any neurological symptom can appear with the disease, and often progresses to physical and cognitive disability. MS takes several forms, with new symptoms occurring either in discrete attacks (relapsing forms) or slowly accumulating over time (progressive forms). Between attacks, symptoms may go away completely, but permanent neurological problems often occur, especially as the disease advances.

There is no known cure for MS. Treatments attempt to return function after an attack, prevent new attacks, and prevent disability (see detailed discussion below). MS medications can have adverse effects or be poorly tolerated, and many patients pursue alternative treatments, despite the lack of supporting scientific study. The prognosis is difficult to predict; it depends on the subtype of the disease, the individual patient's disease characteristics, the initial symptoms and the degree of disability the person experiences as time advances. Life expectancy of patients is nearly the same as that of the unaffected population.

Symptoms of MS usually appear in episodic acute periods of worsening (relapses, exacerbations, bouts or attacks), in a gradually-progressive deterioration of neurologic function, or in a combination of both.

The most common presentation of MS is the clinically isolated syndrome (CIS). In CIS, a patient has an attack suggestive of demyelination, but does not fulfill the criteria for multiple sclerosis. Only 30 to 70% of persons experiencing CIS later develop MS. The disease usually presents with sensorial (46% of cases), visual (33%), cerebellar (30%) and motor (26%) symptoms. Many rare initial symptoms have also been reported, including aphasia, psychosis and epilepsy. Patients first seeking medical attention commonly present with multiple symptoms. The initial signs and symptoms of MS are often transient, mild, and self-limited. These signs and symptoms often do not prompt a person to seek medical attention and are sometimes identified only retrospectively once the diagnosis of MS has been made. Cases of MS are sometimes incidentally identified during neurological examinations performed for other causes. Such cases are referred to as subclinical MS.

The person with MS can suffer almost any neurological symptom or sign, including changes in sensation (hypoesthesia and paraesthesia), muscle weakness, muscle spasms, or difficulty in moving; difficulties with coordination and balance (ataxia); problems in speech (dysarthria) or swallowing (dysphagia), visual problems (nystagmus, optic neuritis, or diplopia), fatigue, acute or chronic pain, and bladder and bowel difficulties. Cognitive impairment of varying degrees and emotional symptoms of depression or unstable mood are also common. The main clinical measure of disability progression and symptom severity is the Expanded Disability Status Scale or EDSS.

Multiple sclerosis relapses are often unpredictable, occurring without warning and without obvious inciting factors. Some attacks, however, are preceded by common triggers. Relapses occur more frequently during spring and summer. Infections such as the common cold, influenza, or gastroenteritis increase the risk of relapse. Stress may also trigger an attack. Pregnancy may affect susceptibility to relapse, offering protection during the last trimester, for instance. During the first few months after delivery, however, the risk of relapse is increased. Overall, pregnancy does not seem to influence long-term disability. Many potential triggers have been examined and found not to influence MS relapse rates. There is no evidence that vaccination for influenza, hepatitis B, varicella, tetanus, or tuberculosis increases risk of relapse. Physical trauma does not trigger relapses. Exposure to higher than usual ambient temperatures can exacerbate extant symptoms, an effect known as Uhthoff's phenomenon. Uhthoff's phenomenon is not, however, an established relapse trigger.

Several subtypes, or patterns of progression, have been described. Subtypes use the past course of the disease in an attempt to predict the future course. They are important not only for prognosis but also for therapeutic decisions. In 1996 the United States National Multiple Sclerosis Society standardized four subtype definitions: relapsing remitting, secondary progressive, primary progressive and progressive relapsing.

The relapsing-remitting subtype is characterized by unpredictable relapses followed by periods of months to years of relative quiet (remission) with no new signs of disease activity. Deficits suffered during attacks may either resolve or leave sequelae. This describes the initial course of 85-90% of individuals with MS. When deficits always resolve between attacks, this is sometimes referred to as benign MS.

Secondary progressive MS describes those with initial relapsing-remitting MS, who then begin to have progressive neurologic decline between acute attacks without any definite periods of remission. Occasional relapses and minor remissions may appear. The median time between disease onset and conversion from relapsing-remitting to secondary progressive MS is 19 years.

The primary progressive subtype describes the approximately 10-15% of individuals who never have remission after their initial MS symptoms. It is characterized by progression of disability from onset, with no, or only occasional and minor, remissions and improvements. The age of onset for the primary progressive subtype is later than other subtypes.

Progressive relapsing MS describes those individuals who, from onset, have a steady neurologic decline but also suffer clear superimposed attacks. This is the least common of all subtypes.

Cases with non-standard behavior have also been described. Sometimes referred to as borderline forms of multiple sclerosis, these include Devic's disease, Balo concentric sclerosis, Schilder's diffuse sclerosis and Marburg multiple sclerosis. Multiple sclerosis also behaves differently in children. There is debate whether these are atypical variants of MS or different diseases.

Multiple sclerosis can be difficult to diagnose since its signs and symptoms may be similar to many other medical problems. Medical organizations have created diagnostic criteria to ease and standardize the diagnostic process for practicing physicians. Historically, the Schumacher and Poser criteria were both popular. Currently, the McDonald criteria focus on a demonstration with clinical, laboratory and radiologic data of the dissemination of MS lesions in time and space. A diagnosis cannot be made until other possible conditions have been ruled out and there is evidence of demyelinating events separated anatomically and in time.

Clinical data alone may be sufficient for a diagnosis of MS if an individual has suffered separate episodes of neurologic symptoms characteristic of MS. Since some people seek medical attention after only one attack, other testing may hasten and ease the diagnosis. The most commonly used diagnostic tools are neuroimaging, analysis of cerebrospinal fluid and evoked potentials. Magnetic resonance imaging of the brain and spine shows areas of demyelination (lesions or plaques). Gadolinium can be administered intravenously as a contrast to highlight active plaques and, by elimination, demonstrate the existence of historical lesions not associated with symptoms at the moment of the evaluation. Testing of cerebrospinal fluid obtained from a lumbar puncture can provide evidence of chronic inflammation of the central nervous system. The cerebrospinal fluid is tested for oligoclonal bands, which are an inflammation marker found in 75-85% of people with MS. The nervous system of a person with MS often responds less actively to stimulation of the optic nerve and sensory nerves due to demyelination of such pathways. These brain responses can be examined using visual and sensory evoked potentials.

MS is currently believed to be an immune-mediated disorder with an initial trigger, which may have a viral etiology, although this concept has been debated for years and some still oppose it. Damage is believed to be caused by the patient's own immune system. The immune system attacks the nervous system, possibly as a result of exposure to a molecule with a similar structure to one of its own.

MS lesions most commonly involve white matter areas close to the ventricles of the cerebellum, brain stem, basal ganglia and spinal cord; and the optic nerve. The function of white matter cells is to carry signals between grey matter areas, where the processing is done, and the rest of the body. The peripheral nervous system is rarely involved.

More specifically, MS destroys oligodendrocytes, the cells responsible for creating and maintaining a fatty layer—known as the myelin sheath—which helps the neurons carry electrical signals. MS results in a thinning or complete loss of myelin and, as the disease advances, the cutting (transection) of the neuron's extensions or axons. When the myelin is lost, a neuron can no longer effectively conduct electrical signals. A repair process, called remyelination, takes place in early phases of the disease, but the oligodendrocytes cannot completely rebuild the cell's myelin sheath. Repeated attacks lead to successively fewer effective remyelinations, until a scar-like plaque is built up around the damaged axons. Four different lesion patterns have been described.

Apart from demyelination, the other pathologic hallmark of the disease is inflammation. According to a strictly immunological explanation of MS, the inflammatory process is caused by T cells, a kind of lymphocyte. Lymphocytes are cells that play an important role in the body's defenses. In MS, T cells gain entry into the brain via the blood-brain barrier, a capillary system that should prevent entrance of T cells into the nervous system. The blood-brain barrier is normally not permeable to these types of cells, unless triggered by infection or a virus, which decreases the integrity of the tight junctions forming the barrier. When the blood-brain barrier regains its integrity, usually after infection or virus has cleared, the T cells are trapped inside the brain. The T cells recognize myelin as foreign and attack it as if it were an invading virus. This triggers inflammatory processes, stimulating other immune cells and soluble factors like cytokines and antibodies. Leaks form in the blood-brain barrier, which in turn cause a number of other damaging effects such as swelling, activation of macrophages, and more activation of cytokines and other destructive proteins.

Although there is no known cure for multiple sclerosis, several therapies have proven helpful. The primary aims of therapy are returning function after an attack, preventing new attacks, and preventing disability. As with any medical treatment, medications used in the management of MS have several adverse effects. Alternative treatments are pursued by some patients, despite the shortage of supporting, comparable, replicated scientific study.

During symptomatic attacks, administration of high doses of intravenous corticosteroids, such as methylprednisolone, is the routine therapy for acute relapses. The aim of this kind of treatment is to end the attack sooner and leave fewer lasting deficits in the patient. Although generally effective in the short term for relieving symptoms, corticosteroid treatments do not appear to have a significant impact on long-term recovery. Potential side effects include osteoporosis and impaired memory, the latter being reversible.

Disease-modifying treatments are expensive and most of these require frequent (up-to-daily) injections. Others require IV infusions at 1-3 month intervals. The earliest clinical presentation of relapsing-remitting MS (RRMS) is the clinically isolated syndrome (CIS). Several studies have shown that treatment with interferons during an initial attack can decrease the chance that a patient will develop clinical MS.

As of 2007, six disease-modifying treatments have been approved by regulatory agencies of different countries for RRMS. Three are interferons: two formulations of interferon β1a (tradenames Avonex, CinnoVex, ReciGen and Rebif) and one of interferon β1b (U.S. tradename Betaseron, in Europe and Japan Betaferon). A fourth medication is glatiramer acetate (Copaxone). The fifth medication, mitoxantrone, is an immunosuppressant also used in cancer chemotherapy, approved only in the USA and largely for secondary progressive MS. The sixth is natalizumab (marketed as Tysabri). All six medications are modestly effective at decreasing the number of attacks and slowing progression to disability, although their efficacy rates differ, and studies of their long-term effects are still lacking. Comparisons between immunomodulators (all but mitoxantrone) show that the most effective is natalizumab, both in terms of relapse rate reduction and halting disability progression; it has also been shown to reduce the severity of MS. Mitoxantrone may be the most effective of them all; however, it is generally not considered as a long-term therapy, as its use is limited by severe cardiotoxicity.

The interferons and glatiramer acetate are delivered by frequent injections, varying from once-per-day for glatiramer acetate to once-per-week (but intra-muscular) for Avonex. Natalizumab and mitoxantrone are given by IV infusion at monthly intervals.

Treatment of progressive MS is more difficult than relapsing-remitting MS. Mitoxantrone has shown positive effects in patients with secondary progressive and progressive relapsing courses. It is moderately effective in reducing the progression of the disease and the frequency of relapses in patients in short-term follow-up. No treatment has been proven to modify the course of primary progressive MS.

As with any medical treatment, these treatments have several adverse effects. One of the most common is irritation at the injection site for glatiramer acetate and the interferon treatments. Over time, a visible dent at the injection site, due to the local destruction of fat tissue, known as lipoatrophy, may develop. Interferons produce symptoms similar to influenza; some patients taking glatiramer experience a post-injection reaction manifested by flushing, chest tightness, heart palpitations, breathlessness, and anxiety, which usually lasts less than thirty minutes. More dangerous are liver damage from interferons and mitoxantrone, the immunosuppressive effects and cardiac toxicity of the latter; and the putative link between natalizumab and some cases of progressive multifocal leukoencephalopathy.

Disease-modifying treatments reduce the progression rate of the disease, but do not stop it. As multiple sclerosis progresses, the symptomatology tends to increase. The disease is associated with a variety of symptoms and functional deficits that result in a range of progressive impairments and disability. Management of these deficits is therefore very important. Both drug therapy and neurorehabilitation have shown to ease the burden of some symptoms, though neither influences disease progression. As for any patient with neurologic deficits, a multidisciplinary approach is key to limiting and overcoming disability; however, there are particular difficulties in specifying a 'core team' because people with MS may need help from almost any health profession or service at some point. Similarly, for each symptom there are different treatment options. Treatments should therefore be individualized depending both on the patient and the physician.

As with most chronic diseases, alternative treatments are pursued by some patients, despite the shortage of supporting, comparable, replicated scientific study. Examples are dietary regimens, herbal medicine, including the use of medical *cannabis* to help alleviate symptoms, and hyperbaric oxygenation. The therapeutic practice of martial arts such as tai chi, relaxation disciplines such as yoga, or general exercise seems to mitigate fatigue, but has no effect on cognitive function.

O. Pemphigus Vulgaris

As described in the Merck Manual, Pemphigus vulgaris is an uncommon, potentially fatal, autoimmune disease characterized by intraepidermal blisters and extensive erosions on apparently healthy skin and mucous membranes. Diagnosis is by skin biopsy with direct immunofluorescence testing. Treatment is with corticosteroids and sometimes immunosuppressants.

Pemphigus vulgaris usually occurs in middle-aged or elderly patients and is rare in children. One variant, paraneoplastic pemphigus, occurs in older patients with malignancy (primarily lymphoreticular); outcome is poor.

The disease is characterized by the presence of autoantibodies directed against intercellular adhesion molecules desmoglein-1 and desmoglein-3 in the epidermis. They are Ca-dependent cadherins, involved in adhesion and cell signaling between epidermal cells. Acantholysis result from either direct inhibition of function of the desmogleins by autoantibody binding or from autoantibody-induced cell signaling that results in down-regulation of cell-cell adhesion and formation of blisters. These autoantibodies are present in both serum and skin during active disease. Any area of stratified squamous epithelium may be affected, including mucosal surfaces. Currently known treatment regimines involve use of drugs such as corticosteroids, immunosuppresants along with or including plasmpheresis and IV immunoglobulin. There is thus a need, therefore, for drugs which can act as desmoglein surrogates and which bind to the offending autoantibodies and prevent said antibodies from attacking desmoglein and causing the symptoms associated with said condition. There is also a need for combinations of antigen surrogates in the treatment of PV that involves treatment with a panel of ligands that have an affinity for each distinct autoantibody present in the sera of an affected patient. The present invention thus includes combination treatment comprising use of antigen surrogate A to antigen A in combination with antigen surrogate B to antigen B in combination with antigen surrogate C to antigen C etc. The ligands or antigen surrogates may be found using screening methodologies described in, for example, US 2007/0003954. Any number of autoantigens may be found and thus any number of high affinity ligands to the autoantibodies responsive to such antoantigens present in PV may be used to treat the condition or disease. High affinity ligands responsive or reactive with unknown autoautobodies that are correlated or present with a disease state or condition may also be used in combination with the ligands identified herein to known autoantibodies such as anti-desmoglein 3.

The present invention also includes screens and/or methods of detecting ligands including peptoids and peptoid like moieties such as cyclic peptoids and/or other oligomers that bind to mitochondrial autoantibodies and other keratinocyte autoantibodies associated with pemphigus vulgaris and other pemphigus related diseases or conditions. The screening methods employed herein may be directed against known autoautobodies as well as unknown autoantibodies in the biological fluid (serum etc.) of a patient having or suspected of having pemphigus vulgaris or a pemphigus related disease or condition. The screening methods can employ methods that screen a known autoantibody in solution against a library of ligands on a support. Once a ligand is identified as a selective ligand, this ligand may be assessed/validated against the autoantibody on a support or in solution to determine the Kd or binding affinity of the ligand antibody complex. Similarly, particular ligands or peptoids may be screened against a panel of known autoantibodies associated with an autoimmune disorder such as pemphigus vulgaris.

There is also a need for the combination treatment of removing the offending T-cells or any immunological source or catalyst of autoantibodies along with a treatment comprising a high affinity ligand (antigen surrogates) for the associated antibodies. There is also a need to have a combination of both diagnostic and therapeutic approaches to the treatment of autoimmune diseases and conditions which involves a method of finding T-cells or B cells associated with an autoimmune disorder pursuant to the methods described in pending application U.S. patent application Ser. No. 12/789, 711 in combination with a method to remove such T-cells (or B-cells) using ligands found in said initial screen and further in combination with a method to prevent the autoantiboides from attacking the natural antigen by treating the patient with a high affinity antigen surrogate found pursuant to the methods disclosed herein.

II. DIAGNOSTIC DETERMINATIONS IN AUTOIMMUNE DISEASES

The present invention, in one aspect, can provide a diagnosis for autoimmune diseases such as those discussed above. This will permit doctors to more readily discern between various diseases with overlapping sets of symptoms, and thus having correctly identified the underlying physiologic basis for a patient's symptoms, open up early intervention and disease management. Indeed, because treatments for many autoimmune disease slow progression and address symptoms, but do not prevent or cure disease, the ability to provide an early diagnosis for these diseases is critical to delaying the onset of more severe symptoms. In addition, being able to provide patients with the correct drugs to address their symptoms without "trial and error" that sometimes results from incorrect diagnosis, will significantly reduce the cost of care, and avoid patient discomfort and possible harm.

In the case of diagnostic assays using the antigen surrogates of the invention, the assays will employ blood or serum samples to test for the presence of the relevant autoantibody. In the assays which employ dual strategies to detect autoantibodies and T-cells, hese assays will employ a T cell-containing patient sample. The most commonly utilized biological sample will be blood or serum due to the prevalence of T cells therein. However, other samples such as tear, saliva, sputum, cerebrospinal fluid, semen or urine may prove useful as well.

In assessing the presence of autoreactive T cells or autoantibodies in the subject, the observed reactivity patterns can be compared to a standard. The standard may rely on known patterns of peptoid binding established for both diseased and normal subjects, and may therefore obviate the need for a the user to provide anything but a reaction control, i.e., a control showing that the reagents and conditions necessary for a positive reaction are present. Alternatively, one may choose to run an actual control which comprises a similar sample from an actual person of known healthy or diseased status. In addition, one may run a series of samples from the same subject over time looking for a trend of increasing autoantibodies or autoreactive T cells as an indication of disease progression.

There are a number of different ways to detect autoantibodies or autoreactive T cells according to the present invention. One type of assay will involve, or be modeled upon, antibody-based assays, including formats such as enzyme linked immunosorbent assays (ELISAs), radioimmunoassays (RIAs), immunoradiometric assays, fluoroimmunoassays, chemiluminescent assays, bioluminescent assays, FACS, FRET and Western blot to mention a few. The steps of various immunodetection methods have been described in the scientific literature, such as, e.g., Doolittle and Ben-Zeev (1999), Gulbis and Galand (1993), De Jager et al. (1993), and Nakamura et al. (1987). In general, such assays will involve the use of a peptoid disposed on a support. The peptoid may previously have been identified as a relevant ligand for an autoreactive T cell population, or instead, it may be part of an array of uncharacterized peptoids, the overall T cell binding pattern for which is predictive of disease or health.

The solid support may be in the form of a column matrix, bead, filter, membrane, stick, plate, or well and the sample will be applied to the immobilized peptoid. After contacting with the sample, unwanted (non-specifically bound) components will be washed from the support, leaving autoantibodies or T cells complexed with the peptoid, which are then detected using various means, such as subsequent addition of antibodies that recognize surface markers on T cells (e.g., CD4, CD8) bound to the support or recognize autoantibodies, or a labeled peptoid or peptoids.

Contacting the chosen biological sample with the peptoid under effective conditions and for a period of time sufficient to allow the formation of peptoid-T cell or peptoid-autoantibody complexes is generally a matter of simply contacting the sample with the peptoid and incubating the mixture for a period of time long enough for the T cells or autoantibodies to bind peptoids. After this time, the sample-peptoid composition, such as a plate, filter or blot, will generally be washed to remove any non-specifically bound cell species or debris, allowing only those cells or autoantibodies specifically bound to the immobilized peptoid to be detected.

In general, the detection of biological complex formation is well known in the art and may be achieved through the application of numerous approaches. These methods are generally based upon the detection of a label or marker, such as any of those radioactive, fluorescent, biological and enzymatic tags. Patents concerning the use of such labels include U.S. Pat. Nos. 3,817,837, 3,850,752, 3,939,350, 3,996,345, 4,277,437, 4,275,149 and 4,366,241. Of course, one may find additional advantages through the use of a secondary binding ligand such as a second antibody and/or a biotin/avidin ligand binding arrangement, as is known in the art.

Various other formats are contemplated and are well known to those of skill in the art. Discussed below are three particular assays envisioned to have ready applicability to the present invention.

A. ELISAs

Immunoassays, in their most simple and direct sense, are binding assays. Certain immunoassays finding particular use in the present invention are various types of enzyme linked immunosorbent assays (ELISAs) and radioimmunoassays (RIA) known in the art.

In one exemplary ELISA, the peptoids of the invention are immobilized onto a selected surface, such as a well in a polystyrene microtiter plate. Then, a test composition suspected of containing the autoantibodies or T cells is added to the wells. After binding and washing to remove non-specifically bound complexes, the bound T cells or bound autoantibodies may be detected. Detection may be achieved by the addition of another peptoid linked to a detectable label. This type of assay is analogous to a simple "sandwich ELISA" except that binding of the labeled agent is direct at antigen-binding portion of the T cell receptor or binding site(s) of the autoantibody. Detection may also be achieved by the addition of a labeled antibody that binds any T cell-specific surface antigen, e.g., that recognizes a structure that is unique to T cells in general, or specific class of T cells or that binds to any antibody. Optionally, the antibody is not labeled, and is followed by the addition of a second antibody that has binding affinity for the first antibody (Fc), with the second antibody being linked to a detectable label.

In another exemplary ELISA, the samples suspected of containing the T cells are immobilized onto a well surface and then contacted with labeled peptoids of the present invention. After binding and washing to remove non-specifically bound immune complexes, the bound labeled peptoids are detected.

Irrespective of the format employed, ELISAs have certain features in common, such as coating, incubating and binding, washing to remove non-specifically bound species, and detecting the bound immune complexes. Because of the simple and predictable chemistry of the peptoids, they can be attached to the support by means of a specific chemical reaction.

"Under conditions effective to allow immune complex formation" means that the conditions preferably include diluting the T cells or autoantibodies with solutions such as BSA, bovine γ globulin (BGG) or phosphate buffered saline (PBS)/Tween. These added agents also tend to assist in the reduction of non-specific background. The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

Detection may utilize an enzyme that will generate color development upon incubating with an appropriate chromogenic substrate. Thus, for example, one will desire to contact or incubate the immune complex with a urease, glucose oxidase, alkaline phosphatase or hydrogen peroxidase-conjugated antibody or peptoid for a period of time and under conditions that favor the development of that immune complex (e.g., incubation for 2 hours at room temperature in a PBS-containing solution such as PBS-Tween).

After incubation with the labeled antibody or peptoid, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H2O2$, in the case of peroxidase as the enzyme label. Quantification is then achieved by measuring the degree of color generated, e.g., using a visible spectra spectrophotometer.

B. Quantum Dots

In connection with the combination of using an antigen surrogate to treat an autoimmune disease and using a method of removing T-cells or B-cells associated with an autoimmune disease, the present invention advantageously uses quantum dots to label cell populations in certain aspects of the present invention. A quantum dot is a semiconductor whose excitons are confined in all three spatial dimensions. As a result, they have properties that are between those of bulk semiconductors and those of discrete molecules. They were discovered by Louis E. Brus, who was then at Bell Labs. Researchers have studied quantum dots in transistors, solar cells, LEDs, and diode lasers. They have also investigated quantum dots as agents for medical imaging and hope to use them as qubits.

There are several ways produce quantum dots. In general, quantum wires, wells and dots are grown by advanced epitaxial techniques in nanocrystals produced by chemical methods or by ion implantation, or in nanodevices made by state-of-the-art lithographic techniques.

Colloidal semiconductor nanocrystals are synthesized from precursor compounds dissolved in solutions, much like traditional chemical processes. The synthesis of colloidal quantum dots is based on a three-component system composed of: precursors, organic surfactants, and solvents. When heating a reaction medium to a sufficiently high temperature, the precursors chemically transform into monomers. Once the monomers reach a high enough supersaturation level, the nanocrystal growth starts with a nucleation process. The temperature during the growth process is one of the critical factors in determining optimal conditions for the nanocrystal growth. It must be high enough to allow for rearrangement and annealing of atoms during the synthesis process while being low enough to promote crystal growth. Another critical factor that has to be stringently controlled during nanocrystal growth is the monomer concentration. The growth process of nanocrystals can occur in two different regimes, "focusing"

and "defocusing". At high monomer concentrations, the critical size (the size where nanocrystals neither grow nor shrink) is relatively small, resulting in growth of nearly all particles. In this regime, smaller particles grow faster than large ones (since larger crystals need more atoms to grow than small crystals) resulting in "focusing" of the size distribution to yield nearly monodisperse particles. The size focusing is optimal when the monomer concentration is kept such that the average nanocrystal size present is always slightly larger than the critical size. When the monomer concentration is depleted during growth, the critical size becomes larger than the average size present, and the distribution "defocuses" as a result of Ostwald ripening.

There are colloidal methods to produce many different semiconductors, including cadmium selenide, cadmium sulfide, indium arsenide, and indium phosphide. These quantum dots can contain as few as 100 to 100,000 atoms within the quantum dot volume, with a diameter of 10 to 50 atoms. This corresponds to about 2 to 10 nanometers, and at 10 nm in diameter, nearly 3 million quantum dots could be lined up end to end and fit within the width of a human thumb.

Large quantities of quantum dots may be synthesized via colloidal synthesis. Colloidal synthesis is by far the cheapest and has the advantage of being able to occur at benchtop conditions. It is acknowledged to be the least toxic of all the different forms of synthesis.

Self-assembled quantum dots are typically between 10 and 50 nm in size. Quantum dots defined by lithographically patterned gate electrodes, or by etching on two-dimensional electron gases in semiconductor heterostructures can have lateral dimensions exceeding 100 nm.

Some quantum dots are small regions of one material buried in another with a larger band gap. These can be so-called core-shell structures, e.g., with CdSe in the core and ZnS in the shell or from special forms of silica called ormosil.

Quantum dots sometimes occur spontaneously in quantum well structures due to monolayer fluctuations in the well's thickness.

Self-assembled quantum dots nucleate spontaneously under certain conditions during molecular beam epitaxy (MBE) and metallorganic vapor phase epitaxy (MOVPE), when a material is grown on a substrate to which it is not lattice matched. The resulting strain produces coherently strained islands on top of a two-dimensional "wetting-layer." This growth mode is known as Stranski-Krastanov growth. The islands can be subsequently buried to form the quantum dot. This fabrication method has potential for applications in quantum cryptography (i.e., single photon sources) and quantum computation. The main limitations of this method are the cost of fabrication and the lack of control over positioning of individual dots.

Individual quantum dots can be created from two-dimensional electron or hole gases present in remotely doped quantum wells or semiconductor heterostructures called lateral quantum dots. The sample surface is coated with a thin layer of resist. A lateral pattern is then defined in the resist by electron beam lithography. This pattern can then be transferred to the electron or hole gas by etching, or by depositing metal electrodes (lift-off process) that allow the application of external voltages between the electron gas and the electrodes. Such quantum dots are mainly of interest for experiments and applications involving electron or hole transport, i.e., an electrical current.

The energy spectrum of a quantum dot can be engineered by controlling the geometrical size, shape, and the strength of the confinement potential. Also, in contrast to atoms, it is relatively easy to connect quantum dots by tunnel barriers to conducting leads, which allows the application of the techniques of tunneling spectroscopy for their investigation. Confinement in quantum dots can also arise from electrostatic potentials (generated by external electrodes, doping, strain, or impurities).

Highly ordered arrays of quantum dots may also be self-assembled by electrochemical techniques. A template is created by causing an ionic reaction at an electrolyte-metal interface which results in the spontaneous assembly of nanostructures, including quantum dots, onto the metal which is then used as a mask for mesa-etching these nanostructures on a chosen substrate.

Conventional, small-scale quantum dot manufacturing relies on a process called "high temperature dual injection" which is impractical for most commercial applications that require large quantities of quantum dots. A reproducible method for creating larger quantities of consistent, high-quality quantum dots involves producing nanoparticles from chemical precursors in the presence of a molecular cluster compound under conditions whereby the integrity of the molecular cluster is maintained and acts as a prefabricated seed template. Individual molecules of a cluster compound act as a seed or nucleation point upon which nanoparticle growth can be initiated. In this way, a high temperature nucleation step is not necessary to initiate nanoparticle growth because suitable nucleation sites are already provided in the system by the molecular clusters. A significant advantage of this method is that it is highly scaleable.

In modern biological analysis, various kinds of organic dyes are used. However, with each passing year, more flexibility is being required of these dyes, and the traditional dyes are often unable to meet the expectations. To this end, quantum dots have quickly filled in the role, being found to be superior to traditional organic dyes on several counts, one of the most immediately obvious being brightness (owing to the high quantum yield) as well as their stability (allowing much less photobleaching). It has been estimated that quantum dots are 20 times brighter and 100 times more stable than traditional fluorescent reporters. For single-particle tracking, the irregular blinking of quantum dots is a minor drawback.

The usage of quantum dots for highly sensitive cellular imaging has seen major advances over the past decade. The improved photostability of quantum dots, for example, allows the acquisition of many consecutive focal-plane images that can be reconstructed into a high-resolution three-dimensional image. Another application that takes advantage of the extraordinary photostability of quantum dot probes is the real-time tracking of molecules and cells over extended periods of time. Researchers were able to observe quantum dots in lymph nodes of mice for more than 4 months.

Semiconductor quantum dots have also been employed for in vitro imaging of pre-labeled cells. The ability to image single-cell migration in real time is expected to be important to several research areas such as embryogenesis, cancer metastasis, stem-cell therapeutics, and lymphocyte immunology.

C. Detection Kits

In still further embodiments, the present invention concerns detection kits for use with the combination methods described above. Peptoids or cyclic peptoids or other ligands according to the present invention will be included in the kit. The kits will thus comprise, in suitable container means, one or more ligands (peptoids) that bind autoantibodies or bind autoantibodies and autoreactive T cells, optionally linked to a detection reagent and/or a support. The kits preferably comprise ligands which bind to the autoantibodies associated with such antoimmune disease. The present invention is thus directed to kits that employ two distinct ligands found through two distinct screening methods-one which employs quantum dots or other similar means to find high affinity ligands to T-cells or other cells associated with the production of autoantibodies; the other which uses a high affinity ligand which acts as an antigen surrogate to the autoantibody or autoantibodies associated with such autoimmune disorder. In this instance, the drug is also used as a diagnostic agent.

In certain embodiments where the peptoid or other ligand is pre-bound to a solid support, the support is provided and includes a column matrix, bead, stick or well of a microtiter plate. The immunodetection reagents of the kit may take any one of a variety of forms, including those detectable labels that are associated with or linked to the given peptoid or antibody. Exemplary antibodies in this instance are those having binding affinity for the surface antigens on T cell receptors.

The container means of the kits will generally include at least one vial, test tube, flask, bottle, syringe or other container means, into which the peptoid may be placed, or preferably, suitably aliquoted. The kits of the present invention will also typically include a means for containing the peptoid, antibody, and any other reagent containers in close confinement for commercial sale. Such containers may include injection or blow-molded plastic containers into which the desired vials are retained.

Cyclic Peptoids:

The inventors have developed a strategy that can be used to synthesize the cyclic molecule/linear molecule pair simultaneously on an external surface of a substrate. Moreover, the methods described are suited for creation of cyclic peptoid libraries for display on microarrays. These arrays are useful for the discovery of peptoids that bind to disease-specific antibodies, as well as other purposes. The methods generally involve treating peptoid-primed Rink amide bead with a solution comprising an attachment residue (e.g., Fmoc-protected Cys) and an initiator peptoid residue (e.g., an ivDde-protected beta-alanine residue). The protective groups protect the amines of the residues and can be removed allowing co-synthesis of a cyclic and a linear molecule. The attachment residue provides a reactive group that can be coupled with a functionalized or activated array substrate (e.g., a thiol group of a cysteine) that is used in later steps to affix or immobilize the molecule to an array substrate (e.g., a maleimide-activated microscope slide). Therefore, to create an array of purely cyclic molecules, with little or no linear compound—only cyclized peptoids contain an attachment residue.

In order to cyclize the peptoid a cyclizing residue will comprise a side chain that can be coupled with a terminal peptoid residue forming a cyclic peptoid (e.g., a glutamic acid or an aspartic acid). The corresponding linear peptoid chain does not have a cyclizing residue. Following removal of protective groups both chains serve as sites for synthesis or polymerization of peptoid chains. These methods eliminate the need to carry out two synthetic operations at each step of library construction, as is necessary in the Pei procedure. Once the linear peptoids are synthesized the bead(s) are exposed to conditions that promote coupling of the side chain group of the cyclizing residue with the N-terminal nitrogen of the peptoid library. Since the linear peptoid chain lacks the cyclizing residue it does not cyclize.

One aspect of the invention is the ability to determine the sequence of hits after screening a one-bead-one-compound library. Since cyclic peptides or peptoids lack a free N-terminus, Edman sequencing cannot be employed. Moreover, while peptoids, like peptides, can be sequenced by tandem mass spectrometry (Paulick et al., 2006), cyclic molecules will fragment at multiple positions, complicating interpretation of the MS/MS spectrum severely. This issue has limited the development of synthetic cyclic peptide libraries. Pei and co-workers addressed this problem recently by developing a "two-compound-one-bead" approach in which each bead contains both a linear and cyclic molecule containing the same peptide sequence (Joo et al., 2006). In other words, the linear molecule encodes the cyclic molecule. This was accomplished using the strategy of Lam (Liu et al., 2002) in which different solvents were employed to segregate beads into two different domains (internal and surface-exposed) to which were attached glutamic acid residues with differentially protected carboxylate side chains. The same peptide chain was then extended from both the internal and external Glu residues. Finally, only the surface-exposed Glu side chains were deprotected, allowing them to be cyclized with the terminal amino group of the peptide. The peptides in the internal layer remained linear and thus served as the encoding strand.

Embodiments of the current invention are directed to a distinct one-bead-two-compound strategy that is tailored to the creation of microarrays, a useful platform for protein fingerprinting and library screening (MacBeath et al., 1999; Uttamchandani et al., 2005). The methods employ differential deprotection to create two chains, both of which contain the peptoid of interest, but only one of which contains both a cyclizing residue to support cyclization as well as an attachment residue to allow specific conjugation of only the cyclic peptoid molecule to an activated or functionalized substrate (Reddy and Kodadek, 2005) (FIG. 1). The linear molecule would not couple to the substrate, but would be present to support tandem MS-based sequencing.

Cyclic Peptoid Libraries and Arrays

In one example, a 7:1 ratio of Fmoc-Cys(Trt)-OH and ivDde-β-Ala-OH was added to β-Ala-primed Rink amide resin. This ratio was optimized empirically to provide enough linear peptoid for tandem MS sequencing from a single bead, but also produce as much cyclic peptoid as possible. After selective deprotection of Fmoc, Fmoc-β-Ala-OH was again attached to Cys followed, after removal of this Fmoc, by addition of Fmoc-Glu(O-2-PhiPr)-OH. At this point, both the Fmoc and ivDde protecting groups were removed and peptoid synthesis was carried out on both strands. Peptoid residues such as methylamine (Nala), allylamine (Nall), isobutylamine (Nleu), 2-methoxyethylamine (Nmea), ethanolamine (Nhse), piperonylamine (Npip), fufurylamine (Nffa), benzylamine (Nphe), and 1,4-diaminobutane (Nlys) were incorporated using conventional sub-monomer chemistry. Peptoids can be synthesized using a microwave (1000 W) assisted synthesis protocol. Beads can be distributed equally into peptoid synthesis reaction vessels, swelled in dimethylformamide (DMF) and each reaction vessel treated with 2M Bromoacetic acid and 3.2 M Di-isopropylcarbodiimide (DIC). Coupling can be performed in a microwave oven. After washing the beads with DMF, each vessel can be treated with a distinct primary amine that can be coupled in a microwave. Beads can be washed, pooled, randomized and redistributed equally into peptide synthesis vessels, and the procedure can be repeated until the desired length is achieved.

The 2-PhiPr protecting group on the Glu side chain is then removed selectively with 1% TFA. Finally, macrocyclization is carried out using the method of Kirshenbaum and colleagues (PyBOP (3 eq.), HOBt (3 eq.) and DIPEA (10 eq.) (Shin et al., 2007). Note that the linear molecule lacks two residues present in the cyclic molecule and thus the mass peaks derived from each can be distinguished easily, facilitating analysis and sequence determination.

To determine the efficacy of this procedure, individual beads were separated and treated with acid to cleave the molecules from the beads, followed by HPLC, MS and MS/MS analysis. The inventors found that in almost every case the sequence of the peptoid on a particular bead could be determined easily by tandem MS analysis of the linear molecule. For some of the molecules, mass spectrometry and HPLC analysis showed that cyclization of the Cys-Glu-containing molecule was clearly incomplete, as linear starting material was clearly detectable. This was not surprising, since a general problem in the creation of cyclic libraries is that not all sequences cyclize with equivalent efficiencies (Marthandan et al., 2005). One would presume that the nature of the N-terminal residue would have the largest effect on cyclization. Indeed, an analysis of more than 50 peptoids by MS/MS revealed that if the N-terminal residue was Nmea, the cyclization yield was almost quantitative. Therefore, one of the preferred terminal residues is Nmea.

Numerous cyclic peptoids can be made in which modest alterations in the side chains of the residues can be introduced in an effort to improve the "fit" of this region of the cyclic peptoid with the binding target. Variants of cyclic peptoids can be assessed for activity in an in vivo assay or in vitro assay against a disease or a condition.

It is contemplated in the present invention that variants or analogs of cyclic peptoids also can be used. Sequence variants can be generated by making conservative substitutions in an identified cyclic peptoid. Substitutional variants typically contain the exchange of one peptoid residue for another at one or more sites within the molecule, and may be designed to modulate one or more properties of the molecule, in particular the affinity of the molecule for the target, without the loss of other functions or properties.

Peptoids may employ modified, non-natural and/or unusual amino acids. Chemical synthesis may be employed to incorporate such residues into compounds of interest. Non-natural residues include, but are not limited to Aad (2-Aminoadipic acid), EtAsn (N-Ethylasparagine), Baad (3-Aminoadipic acid), Hyl (Hydroxylysine), Bala (beta-alanine), Ahyl (allo-Hydroxylysine propionic acid), Abu (2-Aminobutyric acid), 3Hyp (3-Hydroxyproline), 4Abu (4-Aminobutyric acid), 4Hyp (4-Hydroxyproline piperidinic acid), Acp (6-Aminocaproic acid), Ide (Isodesmosine), Ahe (2-Aminoheptanoic acid), Aile (allo-isoleucine), Aib (2-Aminoisobutyric acid), MeGly (N-Methylglycine), Baib (3-Aminoisobutyric acid), MeIle (N-Methylisoleucine), Apm (2-Aminopimelic acid), MeLys (6-N-Methyllysine), Dbu (2,4-Diaminobutyric acid), MeVal (N-Methylvaline), Des (Desmosine), Nva (Norvaline), Dpm (2,2'-Diaminopimelic acid), Nle (Norleucine), Dpr (2,3-Diaminopropionic acid), Orn (Ornithine), and EtGly (N-Ethylglycine).

In addition to the variants discussed above, the present inventors also contemplate that structurally similar compounds may be formulated to mimic the key portions of peptoids of the present invention. Such peptoid compounds may be used in the same manner as peptides and can be functional equivalents thereof. Certain mimetics that mimic elements of protein secondary and tertiary structure are described in Johnson et al. (1993). The underlying rationale behind the use of peptide mimetics is that the peptide backbone of proteins exists chiefly to orient amino acid side chains in such a way as to facilitate molecular interactions. In one aspect a peptoid is thus designed to permit molecular interactions similar to a natural molecule.

It is contemplated that the R groups on the amine nitrogen in the peptoid or cyclic peptoid may be any R group as generally or specifically described herein. The peptoids or cyclic peptoids may have substituents along the peptoid chain as provided in, for example, U.S. application Ser. No. 10/190, 308 which is hereby incorporated by reference.

The term "attach" or "attached" as used herein, refers to connecting or uniting by a bond, link, force or tie in order to keep two or more components together, which encompasses either direct or indirect attachment such that for example where a first molecule is directly bound to a second molecule or material, and the embodiments wherein one or more intermediate molecules are disposed between the first molecule and the second molecule or material.

A "protecting group" is a moiety which is bound to a molecule and designed to block one reactive site in a molecule, but may be spatially removed upon selective exposure to an activator or a deprotecting reagent. Several examples of protecting groups are known in the literature. The proper selection of protecting group (also known as protective group) for a particular synthesis would be governed by the overall methods employed in the synthesis. Activators include, for example, electromagnetic radiation, ion beams, electric fields, magnetic fields, electron beams, x-ray, and the like. A deprotecting reagent could include, for example, an acid, a base or a free radical. Protective groups are materials that bind to a monomer, a linker molecule or a pre-formed molecule to protect a reactive functionality on the monomer, linker molecule or pre-formed molecule, which may be removed upon selective exposure to an activator, such as an electrochemically generated reagent. Protective groups that may be used in accordance with an embodiment of the invention preferably include all acid and base labile protecting groups. For example, amine groups can be protected by t-butyloxycarbonyl (BOC) or benzyloxycarbonyl (CBZ), both of which are acid labile, or by 9-fluorenylmethoxycarbonyl (FMOC), which is base labile. Additionally, hydroxyl groups on phosphoramidites may be protected by dimethoxytrityl (DMT), which is acid labile.

Any unreacted deprotected chemical functional groups may be capped at any point during a synthesis reaction to avoid or to prevent further bonding at such molecule. Capping groups "cap" deprotected functional groups by, for example, binding with the unreacted amino functions to form amides. Capping agents suitable for use in an embodiment of the invention include: acetic anhydride, n-acetylimidizole, isopropenyl formate, fluorescamine, 3-nitrophthalic anhydride and 3-sulfoproponic anhydride.

Additional protecting groups that may be used in accordance with an embodiment of the invention include acid labile groups for protecting amino moieties: tertbutyloxycarbonyl,-tert-amyloxycarbonyl, adamantyloxycarbonyl, 1-methylcyclobutyloxycarbonyl, 2-(p-biphenyl)propyl(2)oxycarbonyl, 2-(p-phenylazophenylyl)propyl(2)oxycarbonyl, alpha, alpha-dimethyl-3,5-dimethyloxybenzyloxy-carbonyl, 2-phenylpropyl(2)oxycarbonyl, 4-methyloxybenzyloxycarbonyl, benzyloxycarbonyl, furfuryloxycarbonyl, triphenylmethyl (trityl), p-toluenesulfenylaminocarbonyl, dimethylphosphinothioyl, diphenylphosphinothioyl, 2-benzoyl-1-methylvinyl, o-nitrophenylsulfenyl, and 1-naphthylidene; as base labile groups for protecting amino moieties: 9-fluorenylmethyloxycarbonyl, methylsulfonylethyloxycarbonyl, and 5-benzisoazolylmethyleneoxycarbonyl; as groups for protecting amino moieties that are labile when reduced: dithiasuccinoyl, p-toluene sulfonyl, and piperidino-oxycarbonyl; as groups for protecting amino moieties that are labile when oxidized: (ethylthio)carbonyl; as groups for protecting amino moieties that are labile to miscellaneous reagents, the appropriate agent is listed in parenthesis after the group: phthaloyl (hydrazine), trifluoroacetyl (piperidine), and chloroacetyl (2-aminothiophenol); acid labile groups for protecting carboxylic acids: tert-butyl ester; acid labile groups for protecting hydroxyl groups: dimethyltrityl; and basic labile groups for protecting phosphotriester groups: cyanoethyl.

Purification of Peptoids

It may be desirable to purify peptoids. Purification techniques are well known to those of skill in the art. These techniques typically involve chromatographic and electrophoretic techniques to achieve partial or complete purification (or purification to homogeneity). Analytical methods particularly suited to the preparation of a pure peptoid are ion-exchange chromatography, exclusion chromatography; polyacrylamide gel electrophoresis; isoelectric focusing. A particularly efficient method of purifying peptoids is fast protein liquid chromatography or even HPLC.

Certain aspects of the present invention concern the purification, and in particular embodiments, the substantial purification, of a peptoid. The term "purified peptoid" as used herein, is intended to refer to a composition, isolatable from other components, wherein the peptoid is purified to any degree relative to its normally-obtainable state. A purified peptoid therefore also refers to a peptoid free from the environment in which it may normally occur.

Generally, "purified" will refer to a peptoid composition that has been subjected to fractionation to remove various other components, and which composition substantially retains its expressed biological activity. Where the term "substantially purified" is used, this designation will refer to a composition in which the peptoid forms the major component of the composition, such as constituting about 50%, about 60%, about 70%, about 80%, about 90%, about 95% or more of the composition by weight.

Various methods for quantifying the degree of purification of the peptoid will be known to those of skill in the art in light of the present disclosure. These include, for example, determining the specific activity of an active fraction, or assessing the amount of peptoid within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "—fold purification number." The actual units used to represent the amount of activity will, of course, be dependent upon the particular assay technique chosen to follow the purification and whether or not the peptoid exhibits a detectable activity.

Peptoid Array

The term "substrate," as used herein, indicates a base material on which processing can be conducted to modify or synthesize a molecule on the surface of the base material or a based material upon which an array of molecules are attached to be used in screening methods (array substrate). Exemplary chemical modifications of a substrate include functionalization and/or depositing a peptoid or an initial residue or base of a peptoid on the surface layer of a base material that is capable of chemically coupling to a peptoid of the invention or a initiator of such a peptoid.

Support materials useful in embodiments of the present invention include, for example, silicon, bio-compatible polymers such as, for example poly(methyl methacrylate) (PMMA) and polydimethylsiloxane (PDMS), glass, SiO2 (such as, for example, a thermal oxide silicon wafer such as that used by the semiconductor industry), quartz, silicon nitride, functionalized glass, gold, platinum, and aluminum. Functionalized surfaces include for example, amino-functionalized glass, carboxy functionalized glass, hydroxy functionalized glass, and amide functionalized beads. Additionally, a support may be coated with one or more layers to provide a surface for molecular attachment or functionalization, increased or decreased reactivity, binding detection, or other specialized application. Support materials and or layer(s) may be porous or non-porous. For example, a support may be comprised of porous silicon. Additionally, the support may be a silicon wafer or chip such as those used in the semiconductor device fabrication industry. A person skilled in the art would know how to select an appropriate support material.

The term "functionalization" as used herein relates to modification of a solid substrate to provide a plurality of functional groups on the substrate surface. By a "functionalized surface" as used herein is meant a substrate surface that has been modified so that a plurality of functional groups are present thereon. The term "functional group" as used herein indicates specific groups of atoms within a molecular structure that are responsible for the characteristic chemical reactions of that structure. Exemplary functional groups include, hydrocarbons, groups containing halogen, groups containing oxygen, groups containing nitrogen and groups containing phosphorus and sulfur all identifiable by a skilled person.

The peptoids present on the array may be linked covalently or non-covalently to the array, and can be attached to the array support (e.g., silicon or other relatively flat material) by cleavable linkers. A linker molecule can be a molecule inserted between the support and peptoid that is being synthesized, and a linker molecule may not necessarily convey functionality to the resulting peptide, such as molecular recognition functionality, but instead elongates the distance between the support surface and the peptoid functionality to enhance the exposure of the peptoid functionality on the surface of the support. Preferably a linker should be about 4 to about 40 atoms long. The linker molecules may be, for example, aryl acetylene, ethylene glycol oligomers containing 2-10 monomer units (PEGs), diamines, diacids, amino acids, among others, and combinations thereof. Examples of diamines include ethylene diamine and diamino propane. Alternatively, the linkers may be the same molecule type as that being synthesized, such as peptoids. A person skilled in the art would know how to design appropriate linkers.

The substrate is typically chemically modified to attach one or more functional groups. The term "attach" or "attached" as used herein, refers to connecting or uniting by a bond, link, force or tie in order to keep two or more components together, which encompasses either direct or indirect attachment such that for example where a first compound is directly bound to a second compound or material, and the embodiments wherein one or more intermediate compounds, and in particular molecules, are disposed between the first compound and the second compound or material.

In particular, in polymer arrays selected functional groups that are able to react with a polymer of choice that forms the polymer arrays are attached to the functionalized substrate surface so that they are presented on the surface. The term "present" as used herein with reference to a compound or functional group indicates attachment performed to maintain the chemical reactivity of the compound or functional group as attached. Accordingly, a functional group presented on a surface, is able to perform under the appropriate conditions the one or more chemical reactions that chemically characterize the functional group.

In those embodiments where an array includes two more features immobilized on the same surface of a solid support, the array may be referred to as addressable. An array is "addressable" when it has multiple regions of different moieties (e.g., different peptoids) such that a region (e.g., a "feature" or "spot" of the array) at a particular predetermined location (e.g., an "address") on the array will detect a particular target or class of targets (although a feature may incidentally detect non-targets of that feature). Array features are typically, but need not be, separated by intervening spaces. In the case of an array, the "target" will be referenced as a moiety in a mobile phase (typically fluid), to be detected by probes ("target probes") which are bound to the substrate at the various regions. However, either of the "target" or "probe" may be the one which is to be evaluated by the other (thus, either one could be an unknown mixture of analytes, e.g., antibodies, to be evaluated by binding with the other).

In one aspect, the present invention provides methods, referred to herein as "small molecule printing," for the generation of high density arrays and the resulting compositions, wherein the small molecules are attached to a solid support using chemical moieties that interact with chemical groups on an activated substrate.

Certain aspects of the invention include methods in which a collection of cyclic peptoids is "printed" onto a support to generate high density arrays. In general, this method comprises (1) providing a solid support, wherein the solid support is functionalized with a moiety capable of interacting with a desired chemical group of a compound or a collection of compounds, to form array attachment(s); (2) providing one or more solutions of the same or different cyclic peptoids to be attached to the solid support; (3) delivering the one or more solutions of the same or different cyclic peptoids to the solid support; and (4) capturing the cyclic peptoids on the support, whereby an array of compounds is generated.

As one of ordinary skill in the art will realize, although any desired chemical compound capable of forming an attachment with the solid support may be utilized, it is preferred that those peptoids generated from split-and-pool library or parallel syntheses are utilized. As will be appreciated by one of ordinary skill in the art, the use of split-and-pool libraries enables the more efficient generation and screening of compounds. However, peptoid molecules synthesized by parallel synthesis methods and by traditional methods can also be utilized in the compositions and methods of the present invention.

As mentioned above, the use of parallel synthesis methods are also applicable. Parallel synthesis techniques traditionally involve the separate assembly of products in their own reaction vessels. For example, a microtiter plate containing n rows and m columns of tiny wells which are capable of holding a small volume of solvent in which the reaction can occur, can be utilized. Thus, n variants of reactant type A can be reacted with m variants of reactant type B to obtain a library of n×m compounds.

Subsequently, once the desired compounds have been provided using an appropriate method, solutions of the desired compounds are prepared. In a certain aspects, compounds are synthesized on a solid support and the resulting synthesis beads are subsequently distributed into polypropylene microtiter plates at a density of one bead per well. Typically, the attached compounds are then released from their beads and dissolved in a small volume of suitable solvent. In a particular embodiments a high-precision transcription array robot (Schena et al., 1995; Shalon et al., 1996); each of which is incorporated herein by reference) can be used to pick up a small volume of dissolved compound from each well and repetitively deliver appropriate volumes of solution to defined locations on a series of functionalized glass substrates. This results in the formation of microscopic spots of compounds on the array substrate. In addition to a high precision array robot (e.g., OmniGrid® 100 Microarrayer (Genomic Solutions)), other means for delivering the compounds can be used, including, but not limited to, ink jet printers, piezoelectric printers, and small volume pipetting robots.

Each cyclic peptoid can contain a common functional group that mediates attachment to a support surface. It is preferred that the attachment formed is robust, for example covalent ester, thioester, or amide attachments. In addition to the robustness of the linkage, other considerations include the solid support to be utilized and the specific class of compounds to be attached to the support. Supports include, but are not limited to glass slides, polymer supports or other solid-material supports, and flexible membrane supports. Examples of supports suitable for use in embodiments of the invention are described in U.S. Pat. No. 5,617,060 and PCT Publication WO 98/59360, each of which are incorporated by reference.

In another embodiment the compounds are attached by nucleophilic addition of a functional group of the compounds being arrayed to an electrophile such as isocyanate or isothiocyanate. Functional groups found useful in adding to an isocyanate or isothiocyanate include primary alcohols, secondary alcohols, phenols, thiols, anilines, hydroxamic acid, aliphatic amines, primary amides, and sulfonamides. In certain embodiments, the nucleophilic addition reaction is catalyzed by a vapor such as pyridine. Other volatile nucleophilic reagents may also be used. In certain embodiments, the nucleophile includes an amine. In certain embodiments, a heteroaryl reagent is used.

The support can be optionally washed and dried, and may be stored at −20° C. for months prior to screening.

Arrays utilized in this invention may include between about 10, 100, 1,000, 2,000, 3,000, 4,000, 5,000, 6,000, 7,000, 8,000, 9,000, 10,000, 12,500 to 25,000, 50,000, 75,000, to about 100,000 distinct cyclic peptoids, including values and ranges there between.

Linkers

The present invention may comprise peptoids joined to various substrates and/or molecules via a linker. Any of a wide variety of linkers may be utilized to effect the joinder of peptoids. Certain linkers will generally be preferred over other linkers, based on differing pharmacologic characteristics and capabilities. In particular, the linkers will be attached at the free —OH group of a peptoid.

Cross-linking reagents are used to form molecular bridges that tie together functional groups of two molecules. Linking/coupling agents used to combine to peptoids or to couple the peptoids to various substrates include linkages such as avidin-biotin, amides, esters, thioesters, ethers, thioethers, phosphoesters, phosphoramides, anhydrides, disulfides, and ionic and hydrophobic interactions.

An exemplary hetero-bifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker may react with a surface or substrate and through a thiol reactive group reacts with a peptoid composition comprising an attachment residue having a thiol group. Numerous types of disulfide-bond containing linkers are known that can be successfully employed in the methods described herein.

Another cross-linking reagent is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent in vivo. The SMPT cross-linking reagent, as with many other known cross-linking reagents, lends the ability to cross-link functional groups such as the SH of cysteine or primary amines (e.g., the epsilon amino group of lysine). Another possible type of cross-linker includes the hetero-bifunctional photoreactive phenylazides containing a cleavable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

In addition to hindered cross-linkers, non-hindered linkers also can be employed in accordance herewith. Other useful cross-linkers, not considered to contain or generate a protected disulfide, include SATA, SPDP and 2-iminothiolane (Wawrzynczak & Thorpe, 1988). The use of such cross-linkers is well understood in the art. Another embodiment involves the use of flexible linkers. U.S. Pat. No. 4,680,338, describes bifunctional linkers useful for producing conjugates of ligands with amine-containing polymers and/or proteins, especially for forming antibody conjugates with chelators, drugs, enzymes, detectable labels and the like. U.S. Pat. Nos. 5,141,648 and 5,563,250 disclose cleavable conjugates containing a labile bond that is cleavable under a variety of mild conditions. This linker is particularly useful in that the agent of interest may be bonded directly to the linker, with cleavage resulting in release of the active agent.

Peptide linkers that include a cleavage site for an enzyme preferentially located or active within a tumor environment also are contemplated. Exemplary forms of such peptide linkers are those that are cleaved by urokinase, plasmin, thrombin, Factor IXa, Factor Xa, or a metallaproteinase, such as collagenase, gelatinase, or stromelysin.

Diagnostic Methods

Data generated by detection of component(s) in a test sample can be compared to control data to determine if the target(s) in the test sample is normal. Control data refers to data obtained from comparable samples from a normal cell, sample, or person, which or who is known to have defined profile with regard to a sample component or a sample condition. For each component being detected, a control amount of a component from a normal or standardized sample can be determined. Preferably, the control amount of a component is determined based upon a significant number of samples taken from samples such as normal cells or persons so that it reflects variations of the amount of these targets seen in the normal cell or population.

If the test amount of a particular component is significantly increased or decreased compared to the control amount of the component, then this is a positive indication that the test sample has an underlying defect or contains a particular test substance or organism, or is diagnostic of a particular condition or disease. For example, if the test amount of a biological pathway component is increased or decreased by at least 5-fold or greater than 10-fold compared to the control amount, then this is an indication that the test sample is distinct from a standard or control sample or has an alteration in a biological or non-biological system. At least 1, 5, 10% or more of the elements, including all values and ranges there between, on the array may meet the 10 fold threshold.

In certain embodiments, methods for detecting components of a biological pathway, e.g., a signal transduction pathway, can comprise: providing a support comprising a plurality of cyclic peptoids immobilized on a surface of the support, wherein the cyclic peptoids specifically bind to one or more target component(s) of a sample, contacting a sample with a support, and detecting the components of the biological pathway bound to their corresponding capture agents. In some embodiments, data generated from a test sample can be compared to a control to determine if there is any defect in the biological pathway in the test sample. The sample preparation methods is described in U.S. Patent Application 2002/0137106, incorporated herein by reference.

Detection Methods

Methods for detecting targets captured or bound on a solid support can generally be divided into photometric methods of detection and non-photometric methods of detection.

Photometric methods of detection include, without limitation, those methods that detect or measure absorbance, fluorescence, refractive index, polarization or light scattering. Methods involving absorbance include measuring light absorbance of an analyte directly (increased absorbance compared to background) or indirectly (measuring decreased absorbance compared to background). Measurement of ultraviolet, visible and infrared light all are known. Methods involving fluorescence also include direct and indirect fluorescent measurement. Methods involving fluorescence include, for example, fluorescent tagging in immunological methods such as ELISA or sandwich assay. Methods involving measuring refractive index include, for example, surface plasmon resonance ("SPR"), grating coupled methods (e.g., sensors uniform grating couplers, wavelength-interrogated optical sensors ("WIOS") and chirped grating couplers), resonant mirror and interferometric techniques. Methods involving measuring polarization include, for example, ellipsometry. Light scattering methods (nephelometry) may also be used.

Non-photometric methods of detection include, without limitation, magnetic resonance imaging, gas phase ion spectrometry, atomic force microscopy and multipolar coupled resonance spectroscopy. Magnetic resonance imaging (MRI) is based on the principles of nuclear magnetic resonance (NMR), a spectroscopic technique used by scientists to obtain microscopic chemical and physical information about molecules. Gas phase ion spectrometers include mass spectrometers, ion mobility spectrometers and total ion current measuring devices.

Mass spectrometers measure a parameter which can be translated into mass-to-charge ratios of ions. Generally ions of interest bear a single charge, and mass-to-charge ratios are often simply referred to as mass. Mass spectrometers include an inlet system, an ionization source, an ion optic assembly, a mass analyzer, and a detector. Several different ionization sources have been used for desorbing and ionizing analytes from the surface of a support or biochip in a mass spectrometer. Such methodologies include laser desorption/ionization (MALDI, SELDI), fast atom bombardment, plasma desorption, and secondary ion mass spectrometers. In such mass spectrometers the inlet system comprises a support interface capable of engaging the support and positioning it in interrogatable relationship with the ionization source and concurrently in communication with the mass spectrometer, e.g., the ion optic assembly, the mass analyzer and the detector. Solid supports for use in bioassays that have a generally planar surface for the capture of targets and adapted for facile use as supports with detection instruments are generally referred to as biochips.

Analysis of Data

Data generated by quantitation of the amount of a sample component of interest (target) bound to each peptoid on the array (e.g., signal transduction components, immunological components, plasma membrane enzyme mediators, cell cycle components, developmental cycle components, or pathogen components) can be analyzed using any suitable means. In one embodiment, data is analyzed with the use of a programmable digital computer. The computer program generally contains a readable medium that stores codes. Certain code can be devoted to memory that includes the location of each feature on a support, the identity of the binding elements at that feature and the elution conditions used to wash the support surface. The computer also may contain code that receives as input, data on the strength of the signal at various addressable locations on the support. This data can indicate the number of targets detected, including the strength of the signal generated by each target.

Data analysis can include the steps of determining signal strength (e.g., height of peaks) of a target(s) detected and removing "outliers" (data deviating from a predetermined statistical distribution). The observed peaks can be normalized, a process whereby the height of each peak relative to some reference is calculated. For example, a reference can be background noise generated by instrument and chemicals (e.g., energy absorbing molecule) which is set as zero in the scale. Then the signal strength detected for each target can be displayed in the form of relative intensities in the scale desired. Alternatively, a standard may be admitted with the sample so that a peak from the standard can be used as a reference to calculate relative intensities of the signals observed for each target detected.

Data generated by the detector, e.g., the mass spectrometer, can then be analyzed by computer software. The software can comprise code that converts signal from the detector into computer readable form. The software also can include code that applies an algorithm to the analysis of the signal to determine whether the signal represents a "peak" in the signal corresponding to a target. The software also can include code that executes an algorithm that compares signal from a test sample to a typical signal characteristic of "normal" or standard sample and determines the closeness of fit between the two signals. The software also can include code indicating whether the test sample has a normal profile of the target(s) or if it has an abnormal profile.

Conditions or Disease States

A binding profile of one or more sample components (biomarkers) can be used to predict, diagnose, or assess a condition or disease state in a subject from which the sample was obtained. A disease state or condition includes, but is not limited to cancer, autoimmune disease, inflammatory disease, infectious disease, neurodegenerative disease, cardiovascular disease, bacterial infection, viral infection, fungus infection, prion infection, physiologic state, contamination state, or health in general. The methods of the invention can use binding profiles and peptoid ligands to differentiate between different forms of a disease state, including pre-disease states or the severity of a disease state.

The present invention particularly contemplates the use of various animal models. For example, various animal models of cancer may be used to determine if the candidate peptoids inhibit cancer cell growth, metastasis or recurrence, or affects its ability to evade the effects of other drugs. Treatment of these animals with test compounds will involve the administration of the compound, in an appropriate form, to the animal. Administration will be by any route the could be utilized for clinical or non-clinical purposes, including but not limited to oral, nasal, buccal, or even topical. Alternatively, administration may be by oral, sublingual, intratracheal instillation, bronchial instillation, intradermal, subcutaneous, intramuscular, intraperitoneal or intravenous injection. The present invention also contemplates pharmaceutical compositions comprising high affinity ligands selected from cyclic peptoids identified through the screening methods claimed herein and a pharmaceutically acceptable excipient. These compositions may also be delivered through any of the means identified above for administering the test compounds to an animal.

Cell Based Screening Formats

Cell based screening assays can be used to identify target-specific ligands, such as cyclic peptoids. Cells having differential characteristics, such as the presence or absence of a cell surface receptor, but otherwise identical, are differentially labeled (e.g., two different colored quantum dots). The cells are then mixed in an approximately 1:1 ratio and then exposed to a library of molecules displayed on a substrate. After appropriate incubation and washing, the beads that bind only one color cell are picked. The beads are treated to remove the cells and other debris, and the bound molecule is identified by an appropriate analytical technique. This two-color assay demands extremely high specificity. If the bead-displayed molecule binds any other molecule on the cell surface other than the target, then both colored cells will be retained and the molecule will not be identified as a hit. See Udugamasooriya et al. (2008).

The assay can be modified to accommodate a variety of different formats. For example, a three cell types assay can be used to distinguish ligands that bind to highly related molecules. For example, where two receptors are almost identical, cells are provided that are null or have one or the other related receptor. Each cell type (null, receptor 1-containing and receptor 2-containing) is labeled with a different agent (e.g., colored quantum dot). The cells are mixed together in an approximately 1:1:1 ratio and exposed to a bead library. Beads that bind only one color cell are picked and the chemical that they display is characterized.

Examples of structures that can be differentiated include antibody or T-cell receptors of various immune cells, growth factor receptors, cell matrix proteins, lectins, carbohydrates, lipids, cell surface antigens from various pathogens. Additionally, the cells could differ not in the composition of the cell surface molecules, but in their arrangement. For example on one cell type, two given cell surface molecules might associate with one another and provide a unique binding site for a ligand that might be absent from a different cell type where these receptors do not associate. Labeling can utilize calorimetric, fluorimetric, bioluminescent or chemilluminescent labels.

The assay can also be modified to identify ligands that bind to cells present in only one of two or more distinct cell populations. For example, all CD4+ T cells from a healthy individual or group of individuals could be labeled with one colored dye and the CD4+ T cells from an individual or group of individuals with an autoimmune disease could be labeled with a different colored dye. The two populations of T cells could then be mixed with the bead library and beads retaining only cells from the autoimmune patients could be selected. These T cells would be candidates for the autoimmune T cells that display the T cell Receptor (TCR) that binds the autoantigen and contributes to disease, since these cells should only be abundant in the autoimmune samples and not in cells obtained from healthy individuals.

In another application, the two or more cell populations could differ solely in the presence or absence of a genetic mutation that might result in a change in the composition and/or organization of molecules on the cell surface.

Kits

Any of the compositions described herein may be comprised in a kit. In a non-limiting example, cyclic peptoids, cyclic peptoid arrays and related support(s), buffers, linkers, and reagents are provided in a kit. The kit may further comprise reagents for processing a sample and/or sample components. The kit may also comprise reagents that may be used to label various components of an array or sample, with for example, radio isotopes or fluorophors.

Kits for implementing methods of the invention described herein are specifically contemplated. In some embodiments, there are kits for synthesis, processing, and detection of cyclic peptoid arrays.

Regents for the detection of sample component binding can comprise one or more of the following: array substrate; cyclic peptoids; and/or detection reagents.

The components of the kits may be packaged either in aqueous media or in lyophilized form. The container means of the kits will generally include at least one vial, test tube, plate, flask, bottle, array substrate, syringe or other container means, into which a component may be placed, and preferably, suitably attached. Where there is more than one component in the kit (labeling reagent and label may be packaged together), the kit also will generally contain a second, third or other additional container into which the additional components may be separately placed. However, various combinations of components may be comprised in a vial. The kits of the present invention also will typically include a means for containing binding elements or reagents for synthesizing such, and any other reagent containers in close confinement for commercial sale. Such containers may include injection or blow molded plastic containers into which the desired vials are retained.

When components of the kit are provided in one and/or more liquid solutions, the liquid solution is typically an aqueous solution that is sterile and proteinase free. In some cases proteinatious compositions may be lyophilized to prevent degradation and/or the kit or components thereof may be stored at a low temperature (i.e., less than about 4☐C.). When reagents and/or components are provided as a dry powder and/or tablets, the powder can be reconstituted by the addition of a suitable solvent. It is envisioned that the solvent may also be provided in another container means.

IV. THERAPIES

The present invention also contemplates the use of peptoids having binding specificity to autoreactive T cells in the context of treatments in combination with treatment of the patient with the high affinity ligand which acts as an antigen surrogate. The present invention also relates to use of the antigen surrogate alone in the treatment of such autoimmune disease or such antigen surrogate may be used in combination with other known treatment regimins for the particular autoimmune disease or condition. In autoimmune disease, the body's own immune response turns upon itself. Most often, this process initiates with certain T cells becoming sensitized to the host's own antigen—a process that does not take place in healthy subjects. If these autoreactive T cells could be selectively reduced or eliminated, i.e., without affecting other T cells necessary for normal immune surveillance and activity, then autoimmune disease symptoms should at least be mitigated, if not eliminated completely. The combination therapy claimed and disclosed herein can certainly be used to mitigate or eliminate all symptoms of the disease by removing the T-cells or other antibody producing/catalyzing cells and by preventing the destruction of the natural antigen by the autoantibody via use of the antigen surrogate. In a preferred embodiment, the antigen surrogate is a cyclic peptoid. The present invention also relates to such combination therapy wherein an immunoconjugate may be formed from the peptoid or ligand which binds to the T-cell and directs an immunotoxin to the offending T-cell is used in combination with the high affinity antigen surrogate found pursuant to the methods disclosed herein to treat the autoimmune condition or disease. All of the methods disclosed herein may be used in combination depending upon the physicians prescribed method of treatment.

A. Adherence-Based Methods for Eliminating T Cells

In one embodiment, it is proposed that supports coated with peptoids having proven specificity for autoreactive T cells could be used to "pan" the blood of subjects suffering from autoimmune disease. This approach would follow the parameters and use the same equipment for leukapheresis as applied in other contexts, such as cancer therapy or in the collection of stem cells.

More generally, leukapheresis is a laboratory procedure in which white blood cells are separated from a sample of blood. This may be done to decrease a very high white blood cell count in individuals with cancer (leukemia) or to remove white blood cells for transfusion. Alternatively, only granulocytes, macrophages and monocytes can be removed, leaving the lymphocyte count largely unchanged. This is used as a treatment for autoimmune diseases such as ulcerative colitis and rheumatoid arthritis, where these cells play an active part in the inflammation process.

The peptoid would be bound to a support across which blood would be passed, allowing autoreactive T cells to bind to the support and be removed from the sample prior to return to the patient. In contrast, T cells not binding to the peptoid would not be bound and would be returned to the patient. Blood is obtained from the patient via an intravenous line and is returned in the same fashion, usually on opposite arms. The blood typically is driven across the support by means of a pump. A typical duration for the procedure is 3-4 hours.

It is contemplated herein that such method can be used in combination with treatment of the patient with an antigen surrogate discovered by screening a library of ligands against a known autoantibody. Such antibodies can be obtained commercially from antibody library commercial suppliers.

B. Toxin and Immunoconjugate Therapies

In another embodiment, antigen surrogate peptoids of the invention are used in combination with T-cell peptoids that are targeting agents that deliver a payload specifically to the T cells that they bind. In one embodiment, the payload may be a toxin, which can may be attached to peptoids using standard cross-linking chemistries. Toxins have a wide variety of forms and actions, as discussed further below. Another option is to link an immune effector to the peptoid for targeting to the T cells. One such immune effect is an IgG Fc-containing molecule. A discussion of Fc-containing molecules also is provided below.

Any of a wide variety of linkers may be utilized to effect the joinder of peptoids. Certain linkers will generally be preferred over other linkers, based on differing pharmacologic characteristics and capabilities, but generally, any linking/coupling agents known to those of skill in the art can be used to combine to peptoids of the present invention with toxins, such as, avidin-biotin linkages, amide linkages, ester linkages, thioester linkages, ether linkages, thioether linkages, phosphoester linkages, phosphoramide linkages, anhydride linkages, disulfide linkages, ionic and hydrophobic interactions.

TABLE 1

HETERO-BIFUNCTIONAL CROSS-LINKERS

| Linker | Reactive Toward | Advantages and Applications | Spacer Arm Length |
|---|---|---|---|
| SMPT | Primary amines Sulfhydryls | Greater stability | 11.2 A |
| SPDP | Primary amines Sulfhydryls | Thiolation Cleavable cross-linking | 6.8 A |
| LC-SPDP | Primary amines Sulfhydryls | Extended spacer arm | 15.6 A |
| Sulfo-LC-SPDP | Primary amines Sulfhydryls | Extended spacer arm Water-soluble | 15.6 A |
| SMCC | Primary amines Sulfhydryls | Stable maleimide reactive group Enzyme-antibody conjugation Hapten-carrier protein conjugation | 11.6 A |
| Sulfo-SMCC | Primary amines Sulfhydryls | Stable maleimide reactive group Water-soluble Enzyme-antibody conjugation | 11.6 A |
| MBS | Primary amines Sulfhydryls | Enzyme-antibody conjugation Hapten-carrier protein conjugation | 9.9 A |
| Sulfo-MBS | Primary amines Sulfhydryls | Water-soluble | 9.9 A |
| SIAB | Primary amines Sulfhydryls | Enzyme-antibody conjugation | 10.6 A |
| Sulfo-SIAB | Primary amines Sulfhydryls | Water-soluble | 10.6 A |
| SMPB | Primary amines Sulfhydryls | Extended spacer arm Enzyme-antibody conjugation | 14.5 A |
| Sulfo-SMPB | Primary amines Sulfhydryls | Extended spacer arm Water-soluble | 14.5 A |
| EDC/Sulfo-NHS | Primary amines Carboxyl groups | Hapten-Carrier conjugation | 0 |
| ABH | Carbohydrates Nonselective | Reacts with sugar groups | 11.9 A |

An exemplary hetero-bifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker may react with the lysine residue(s) of one protein (e.g., the selected antibody or fragment) and through the thiol reactive group, the cross-linker, already tied up to the first protein, reacts with the cysteine residue (free sulfhydryl group) of the other protein (e.g., the selective agent).

It is particular that a cross-linker having reasonable stability in blood will be employed. Numerous types of disulfide-bond containing linkers are known that can be successfully employed to conjugate targeting and therapeutic/preventative agents. Linkers that contain a disulfide bond that is sterically hindered may prove to give greater stability in vivo, preventing release of the targeting peptide prior to reaching the site of action. These linkers are thus one group of linking agents.

Another cross-linking reagent is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent to the target site.

The SMPT cross-linking reagent, as with many other known cross-linking reagents, lends the ability to cross-link functional groups such as the SH of cysteine or primary amines (e.g., the epsilon amino group of lysine). Another possible type of cross-linker includes the hetero-bifunctional photoreactive phenylazides containing a cleavable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

In addition to hindered cross-linkers, non-hindered linkers also can be employed in accordance herewith. Other useful cross-linkers, not considered to contain or generate a protected disulfide, include SATA, SPDP and 2-iminothiolane (Wawrzynczak & Thorpe, 1986). The use of such cross-linkers is well understood in the art. Another embodiment involves the use of flexible linkers.

U.S. Pat. No. 4,680,338, describes bifunctional linkers useful for producing conjugates of ligands with amine-containing polymers and/or proteins, especially for forming antibody conjugates with chelators, drugs, enzymes, detectable labels and the like. U.S. Pat. Nos. 5,141,648 and 5,563,250 disclose cleavable conjugates containing a labile bond that is cleavable under a variety of mild conditions. This linker is particularly useful in that the agent of interest may be bonded directly to the linker, with cleavage resulting in release of the active agent. Preferred uses include adding a free amino or free sulfhydryl group to a protein, such as an antibody, or a drug.

U.S. Pat. No. 5,856,456 provides peptide linkers for use in connecting polypeptide constituents to make fusion proteins, e.g., single-chain antibodies. The linker is up to about 50 amino acids in length, contains at least one occurrence of a charged amino acid (preferably arginine or lysine) followed by a proline, and is characterized by greater stability and reduced aggregation. U.S. Pat. No. 5,880,270 discloses aminooxy-containing linkers useful in a variety of immunodiagnostic and separative techniques.

Peptide linkers that include a cleavage site for an enzyme preferentially located or active within a cellular environment also are contemplated. Exemplary forms of such peptide linkers are those that are cleaved by urokinase, plasmin, thrombin, Factor IXa, Factor Xa, or a metallaproteinase, such as collagenase, gelatinase, or stromelysin.

However, peptoids also provide a unique opportunity, being synthetic, for incorporation of simpler and more effective attachment points as compared to peptides and proteins.

1. Toxins

A variety of biological toxins may be used in accordance with the present invention. The term "biotoxin" as used herein refers to a toxin of biological origin. Toxins produced by microorganisms are important virulence determinants responsible for microbial pathogenicity and/or evasion of the host immune response. Biotoxins vary greatly in purpose and mechanism, and can be highly complex (the venom of the cone snail contains dozens of small proteins, each targeting a specific nerve channel or receptor), or relatively small protein. Biotoxins in nature have two primary functions—predation (spider, snake, scorpion, jellyfish, wasp) and defense (bee, ant, termite, honeybee, wasp, poison dart frog). Some of the more well known types of biotoxins include cyanotoxins (produced by cyanobacteria), hemotoxins (target and destroy red blood cells; pit vipers such as rattlesnakes), necrotoxins (cause necrosis; brown recluse, "puff adder"—*Bitis arietans*), neurotoxins (black widow, scorpions, box jellyfish).

Of particular interest in accordance with the present invention are cytotoxins, such as ricin, from the castor bean plant. Also useful are bacterial toxins including those from *Clostridium: tetani* (tetanospasmin), *perfringens* (alpha toxin, enterotoxin), *difficile* (A, B), *botulinum* (botox), *Staphylococcus* (*S. aureus* alpha/beta/delta, exfoliatin, toxic shock syndrome toxin, SEB), as well as anthrax toxin, listeriolysin O, streptolysin, leukocidin (Panton-Valentine leukocidin), cord factor, diphtheria toxin, shiga toxin, verotoxin/shiga-like toxin (E. coli), E. coli heat-stable enterotoxin/enterotoxin, cholera toxin, pertussis toxin, Pseudomonas exotoxin, extracellular adenylate cyclase type I (Superantigen), type II (pore forming toxins), type III (AB toxin/AB5), lipopolysaccharide (Lipid A), Bacillus thuringiensis delta endotoxin, clumping factor A, and fibronectin binding protein A.

Chromophore assisted light inactivation (CALI) of proteins involves generating highly reactive species (often singlet oxygen) from a chromophore (the warhead) using light. The reactive species damages the target protein, inactivating its biological function. These molecules can be used to knock-out the function of a protein.

Experiments by the inventor have showed a ruthenium-based chromophore to be an effective warhead. They demonstrated that the ruthenium chromophore can enter cells and inactivate a target, thereby permitting CALI treatments of living cells in vivo and ex vivo.

2. Fc-Containing Molecules

Antibodies bivalent are made of up four polypeptide chains—two short segments having variable regions, and two longer segments, having both variable and constant regions. Long and short chains interact via disulfide bonds and make up half of a normal antibody, with the variable portion being responsible for antigen binding (Fv, or fragment variable). Two antibody halves interact via distinct disulfide bonds and in the Fc (fragment, crystallizable) portion.

The Fc portion plays an import role in modulating immune cell activity, such as binding to various cell receptors and immune molecules, such as complement proteins. By doing this, it mediates different physiological effects including opsonization, cell lysis, and degranulation of mast cells, basophils and eosinophils. In particular, it can mark cells for destruction by other immune components. The present invention seeks to utilize antibodies, or Fc-containing fragments thereof, to target T cells for destruction.

One particular technology that can be used is described by Popkov et al. (2009). The authors engineered antibodies to contain integrin α(v)β(3) and α(v)β(5) adapter ligands, which self-assembled mounted an instant, chemically-programmed, polyclonal response against the implanted tumors having these targets. Significant therapeutic responses were observed without recourse to adjuvant therapy. The chemically-programmed immune responses were driven by antibody-dependent cellular cytotoxicity and complement-directed cytotoxicity. This demonstrates the ability of small molecule ligands to "hi-jack" antibodies by redirecting their binding specificity. This method can be used in combination with treating the patient with an antigen surrogate.

C. Combination Therapies

The therapies discussed above may be administered in combination with another agent for the treatment of an autoimmune disease. By combining agents, an additive effect may be achieved while not increasing the toxicity (if any) associated with a monotherapy. In addition, it is possible that more than additive effects ("synergism") may be observed. Thus, combination therapies are a common way to exploit new therapeutic regimens.

The peptoid treatment may precede, be co-current with and/or follow the other agent(s) by intervals ranging from minutes to weeks. In embodiments where the peptoid treatment and other agent(s) are applied administered, one would generally ensure that a significant period of time did not expire between the time of each delivery, such that the peptoid treatment and other agent(s) would still be able to exert an advantageously combined effect on the subject. For example, in such instances, it is contemplated that one may provide two, three, four or more modalities substantially simultaneously (i.e., within less than about a minute) with the peptoid treatment. In other aspects, one or more agents may be administered within of from substantially simultaneously, about 1 minute, about 5 minutes, about 10 minutes, about 20 minutes about 30 minutes, about 45 minutes, about 60 minutes, about 2 hours, about 3 hours, about 4 hours, about 5 hours, about 6 hours, about 7 hours about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 22 hours, about 23 hours, about 24 hours, about 25 hours, about 26 hours, about 27 hours, about 28 hours, about 29 hours, about 30 hours, about 31 hours, about 32 hours, about 33 hours, about 34 hours, about 35 hours, about 36 hours, about 37 hours, about 38 hours, about 39 hours, about 40 hours, about 41 hours, about 42 hours, about 43 hours, about 44 hours, about 45 hours, about 46 hours, about 47 hours, about 48 hours, about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 1, about 2, about 3, about 4, about 5, about 6, about 7 or about 8 weeks or more, and any range derivable therein, prior to and/or after administering the peptoid.

Various combination regimens of the peptoid treatment and one or more agents may be employed. Non-limiting examples of such combinations are shown below, wherein a peptoid treatment is "A" and a second agent is "B":

| A/B/A | B/A/B | B/B/A | A/A/B | A/B/B | B/A/A | A/B/B/B | B/A/B/B |
|-------|-------|-------|-------|-------|-------|---------|---------|
| B/B/B/A | B/B/A/B | A/A/B/B | A/B/A/B | A/B/B/A | B/B/A/A | | |
| B/A/B/A | B/A/A/B | A/A/A/B | B/A/A/A | A/B/A/A | A/A/B/A | | |

Thus, peptoid therapies of the present invention can be used in conjunction with other therapies that are used for the treatment of disorders discussed above, but include various anti-inflammatory and immune suppressive treatments.

There is a need to develop new treatments of pemphigus vulgaris and similar disorders or conditions that can avoid the use or overuse of systemic corticosteroids. PV antibodies react with desmoglein 3(Dsg3) and other self-antigens. Downstream signaling events are elicited which cause cell shrinkage, detachment from adjacent cells and rounding up. Acantholysis in PV can be blocked by inhibitors of signaling kinases which include p38 MAPK, mammalian target of rapamycin (mTOR), Src and epidermal growth factor receptor (EGFR). It can also be blocked by other tyrosine kinases, calmodulin, phospholipase C and inhibitors of executioner caspases. Thus, the present invention also relates to combination treatment that includes the use of the T-cell ligands, autoantibody ligands and drugs that inhibit the downstream signaling events that lead to or are responsible and/or partially responsible for development and progression of PV including inhibitors of each of the targets/proteins referenced in this paragraph. Specific examples of possible drugs used in combination with the ligands of the invention are listed in Table 1 below.

TABLE 1

| Drug | Target |
|---|---|
| Afatinib | EGFR/Erb2 |
| Bevacizumab | VEGF |
| Cetuximab | Erb1 |
| Crizotinib | ALK/Met |
| Dasatinib | |
| Erlotinib | Erb1 |
| Fostamatinib | Syk |
| Gefitinib | EGFR |
| Imatinib | Bcr-Abl |
| Lapatinib | Erb1/Erb2 |
| Lenvatinib | VEGFR2/VEGFR2 |
| Mubritinib | |
| Nilotinib | Bcr-Abl |
| Panitumumab | EGFR |
| Pazopanib | VEGFR2/PDGFR/c-kit |
| Pegaptanib | VEGF |
| Ranibizumab | VEGF |
| Ruxolitinib | JAK |
| Sorafenib | |
| Sunitinib | |
| Trastuzumab | Erb2 |
| Vandetanib | RET/VEGFR/EGFR |
| Vemurafenib | BRAF |

V. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Methods

Peptoid Library Synthesis

Details regarding design of the peptoid library have been published previously (Udugamasooriya et al., 2008). Briefly, the library is synthesized on TentaGel macrobeads (140-170 μM diameter; substitution: 0.48 mmol/g resin; Rapp Polymere). Synthesis of the library is conducted using eight different amines resulting in a theoretical diversity of 262,144 compounds. A 9-mer library is synthesized using a microwave (1000 W)-assisted synthesis protocol and a split and pool method (Olivos et al., 2002). At the completion of library synthesis, beads are treated with a 95% TFA, 2.5% triisopropylsilane, and 2.5% water mixture for 2 hours to remove side chain protection groups and then neutralized with 10% diidoproplyethylamine in DMF. The beads are washed with dichloromethane, dried, and stored at 4° C. until use.

Resynthesis of Soluble Peptoids.

Resynthesis of peptoid ligands and scrambled control peptoids is conducted on Knorr amide MBHA resin (Novabiochem) using a standard microwave-assisted protocol (Olivos et al., 2002) (1000 W microwave oven, 10% power delivered for 2×15 seconds with brief mixing in between). For biotinylated and biotin-DOPA peptoids, Fmoc-Glu(biotinyl-PEG)-OH (Novabiochem) and Fmoc-DOPA (Novabiochem) are subsequently coupled on Knorr amide MBHA resin by a standard peptide synthesis protocol using Fmoc chemistry (Udugamasooriya et al., 2008). A standard microwave-assisted protocol is used to create the peptoid portion of the molecules as described above. Peptoids arecleaved from the resin with 95% TFA, 2.5% triisopropylsilane, and 2.5% water for 2 hours, and purified using a Waters Breeze HPLC system. Mass of peptoids was detected using a MALDI-Voyager DE Pro mass spectrometer.

Cyclic Peptoid Library Synthesis.

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Materials and Equipments.

All commercial reagents were used as obtained without further purification. O-tert-Butyl-2-amino ethanol was purchased from CSPS Pharmaceuticals. Methylamine was used as 2 M solution in THF. Polystyrene AM RAM macrobead (500-560 μm; 0.52 mmol/g) and Rink Amide AM LL (100-200 mesh, 0.35 mmol/g) resins were obtained from Rapp Polymere and Novabiochem, respectively. NMR spectra were recorded on a Varian 300 MHz spectrometer. Preparative HPLC was performed on a Waters binary HPLC system with a C18 reverse-phase column with the gradient elution of water/acetonitrile with 0.1% TFA. MS and tandem MS (MALDI-TOF) were performed on a Voyager-DE PRO biospectrometry workstation and 4700 Proteomics Analyzer (Applied Biosystems) with α-cyano-4-hydroxycinnamic acid as a matrix, respectively. The synthesis of peptides was performed in a New Brunswick Scientific Innova 4000 incubator shaker. The synthesis of peptoids under microwave conditions was performed in a 1000 W Whirlpool microwave oven (model MT1130SG) with 10% power. Standard glass peptide synthesis vessels (Chemglass) were used for the synthesis in the incubator shaker and in the microwave oven. Microarrays were prepared on maleimide-functionalized glass slides by using SpotArray 72 Microarray Printing System (PerkinElmer). Hybridized microarrays were scanned with a GenePix 4000B scanner.

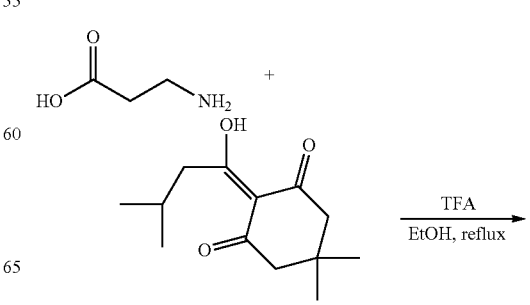

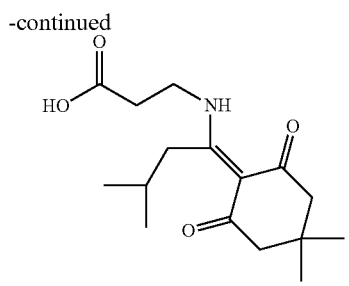

Synthesis of ivDde-β-Ala-OH.

To a stirred suspension of H-β-Ala-OH (1.02 g, 11.4 mmol) and ivDde-OH (5 ml, 22.9 mmol) in EtOH was added TFA (88 μL, 1 mmol) at room temperature.[1] The mixture was then refluxed for 24 hours. After the solvent was evaporated in vacuo, a crude product was purified by column chromatography with $CH_3OH/CH_2Cl_2$ (0.1% TFA) gradient to afford ivDde-β-Ala-OH (3.3 g, 97.6%). NMR ($CDCl_3$) δ 1.02 (m, 12H), 1.90-2.03 (m, 1H), 2.39 (s, 4H), 2.75 (t, J=6.0 Hz, 2H), 3.06 (br d, =6.0 Hz, 2H), 3.78 (q, J=6.0 Hz, 2H); $^{13}C$ NMR ($CDCl_3$) δ 22.8, 28.4, 29.4, 30.2, 34.1, 37.4, 39.6, 52.9, 107.4, 173.0, 177.2; MS (MALDI) m/z: calcd for $C_{16}H_{26}NO_4$ 296.2; found 296.5 $[M+H]^+$.

Cyclization Reactions of Peptoids on Bead.

Preliminary cyclization reactions of peptoids on bead were tested under various conditions. The typical procedure with PyBOP which gave the best results is as follows. The cyclization yields also depended on the length of the peptoid with high yields requiring at least six monomeric units. Fmoc-Cys(Trt)-OH and Fmoc-Glu(O-2-PhiPr)-OH were coupled to the Rink Amide AM resin sequentially by using Fmoc chemistry. The synthesis of peptoids was performed by employing a microwave-assisted submonomer protocol.[2] 2-PhiPr group was deprotected with 1% TFA and 2% triisopropylsilane in DCM for 2*30 min. After the resins were thoroughly washed with 5% DIPEA in DCM and DCM, cyclization was carried out under the conditions of PyBOP (3 eq.), HOBt (3 eq.) and DIPEA (10 eq.) in DMF for 2*10 h. Cyclic peptoids were confirmed by MALDI-MS and HPLC after cleavage from beads.

General Procedure for the Construction of Encoded Cyclic Peptoid Libraries.

Polystyrene AM RAM macrobeads in DMF were allowed to swell at room temperature for 1 h. After DMF was drained, the beads were incubated with 20% piperidine for 30 min. The beads were thoroughly washed with DMF (8×3 mL) and then treated with Fmoc-β-Ala-OH (5 eq.) by using HBTU (5 eq.), HOBt (5 eq.) and DIPEA (10 eq.) in DMF for 2 h. After The beads were thoroughly washed with DMF (8×3 mL) and incubated with 20% piperidine for 30 min, they were thoroughly washed with DMF (8×3 mL) and then treated with ivDde-β-Ala-OH (0.6 eq.) and Fmoc-Cys(Trt)-OH (4 eq.) by using HBTU (4.6 eq.) and NMM (10 eq.) in DMF. After 2 h, the beads were thoroughly washed with DMF (8×3 mL) and then treated with $Ac_2O$ (10 eq.) and DIPEA (10 eq.) in DMF for 1 h to block possible unreacted amines. After the beads were thoroughly washed with DMF (8×3 mL) and Fmoc group was selectively removed with the treatment of 20% piperidine for 30 min, they were again coupled with Fmoc-β-Ala-OH (5 eq.) by using HBTU (5 eq.), HOBt (5 eq.) and DIPEA (10 eq.) in DMF for 2 h. After the beads were thoroughly washed with DMF (8×3 mL) and incubated with 20% piperidine for 30 min, they were treated with Fmoc-Glu(O-2-PhiPr)-OH (3 eq.) by using HATO (3 eq.), HOBt (3 eq.) and DIPEA (10 eq.) in DMF. After 2 h, the beads were thoroughly washed with DMF (8×3 mL) and then treated with $Ac_2O$ (10 eq.) and DIPEA (10 eq.) in DMF for 1 h to block possible unreacted amines. ivDde and Fmoc groups were removed with the successive treatments of 2.5% hydrazine for 2*10 min and 20% piperidine for 30 min. After the beads were thoroughly washed with DMF (8×3 mL), split-and-mix linear peptoid libraries consisting of 7-mer peptoids were prepared by using bromoacetic acid and primary amines such as methylamine, allylamine, 2-methoxyethylamine, 0-tert-butyl-2-amino ethanol, piperonylamine, fufurylamine, benzylamine, 1-N-tert-butyloxycarbonyl-1,4-diaminobutane based on a microwave-assisted submonomer protocol.[2] 2-PhiPr group was selectively deprotected with 1% TFA and 2% triisopropylsilane (TIS) in DCM for 2*30 min. After the resins were thoroughly washed with 5% DIPEA in DCM and DCM, cyclization was carried out under the conditions of PyBOP (3 eq., ~30 mM), HOBt (3 eq. ~30 mM) and DIPEA (10 eq.) in DMF for 2*10 h. Cyclization yields depended on the residues at N-terminal. Cyclic peptoid libraries consisting of Nmea at the N-terminal afforded much better results with almost complete cyclization. Cyclic peptoids were confirmed by MS, tandem MS (MALDI) or HPLC after cleavage from the resin under the conditions of 95% TFA and 5% TIS for 1.5 h.

Hybridization of Biotin-Labeled Cyclic Peptoids Microarray and Streptavidin-Cy3.

Microarrays consisting of biotin-labeled cyclic peptoids with Nmea at the N-terminal were prepared. Biotin-labeled cyclic peptoids were spotted onto maleimide-functionalized glass slides with 3-fold serial dilution of about 2 mM solution. Microarrays were equilibrated with 1×TBST (50 mM Tris/150 mM NaCl/0.1% Tween 20, pH 8.0) for 30 min at 4° C. Microarray slides were incubated with Streptavidin-Cy3 (10 μL, Sigma) and BSA (50 μL of 2 mg/mL) in 1×TBST (total 1 mL solution) with gentle shaking for 45 min at 4° C. The slides were washed with 1×TBST (3×5 min) at 4° C., and then dried by centrifugation. Hybridized microarrays were scanned with a GenePix 4000B scanner.

Figure 2:
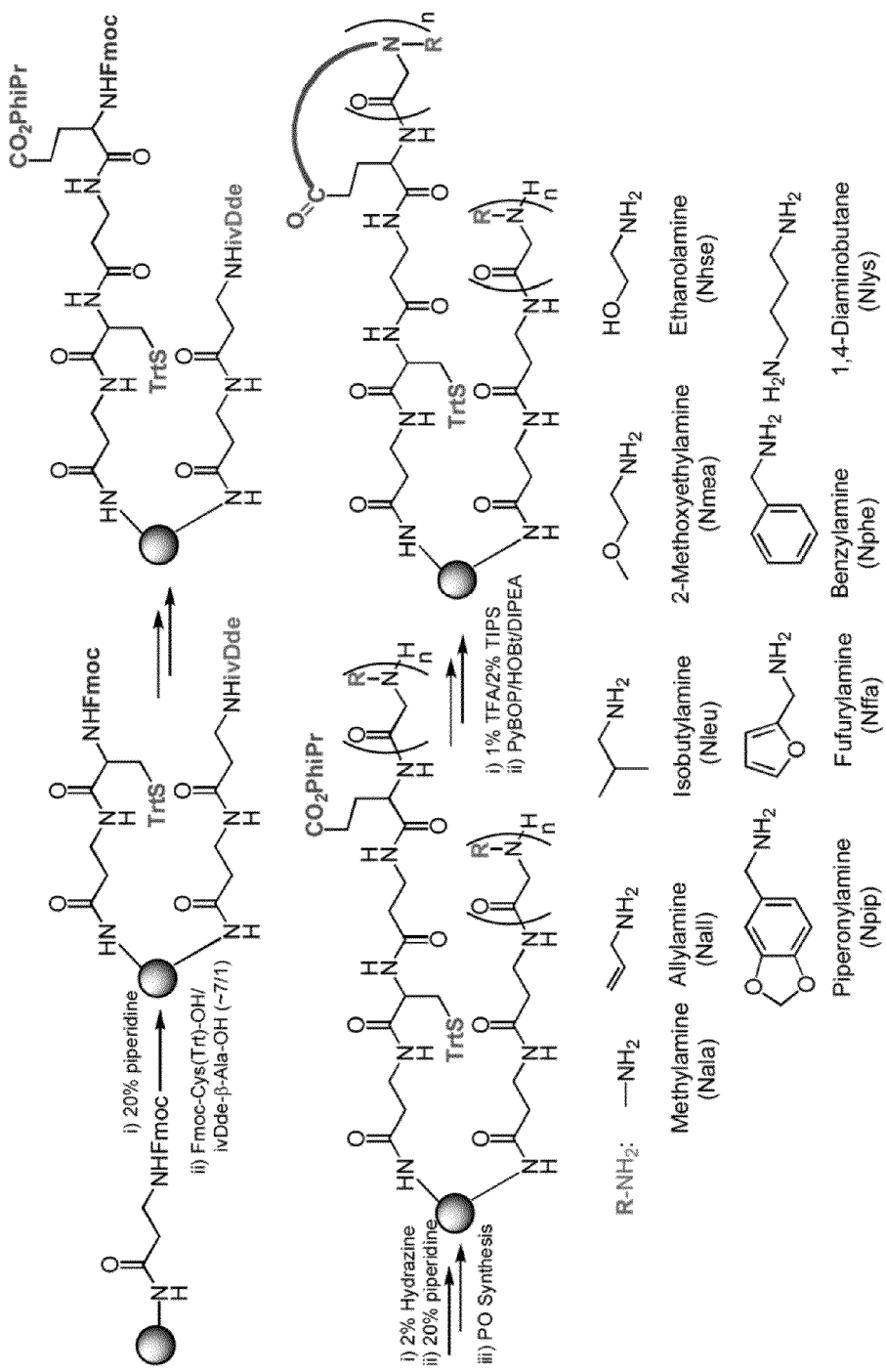

Ten peptoids of the form were prepared: β-Ala-Cys-Glu(Biotin)-cyclo(Glu-X-X-X-X-X-X-Nmea) (see FIGS. 3A-C), where biotin-Glu bears a side chain-conjugated biotin and X was derived from one of the amines shown in FIG. 2. The molecules were cleaved from the resin and analyzed by HPLC and tandem MS. In each case, the inventors were able to easily sequence the linear species by tandem mass spectrometry. Moreover, all of the detectable Cys-containing molecules were in the cyclic form. In addition, the peptoid of formula 1a was also prepared by analogous methods.

Figure 3A:
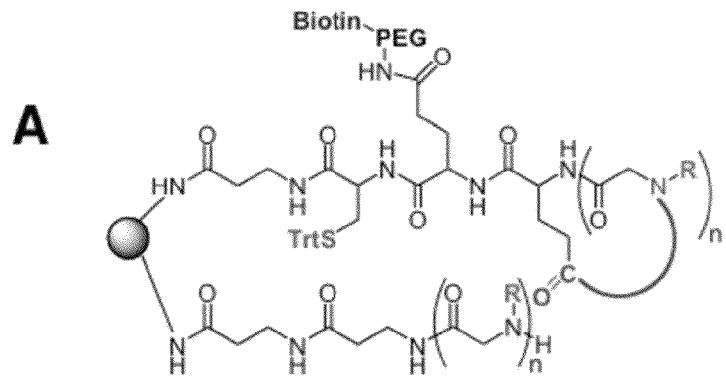
FIGS. 3A-3C—Attachment of Cys-containing cyclic peptoid to a maleimide-activated glass slide.
Figure 3B:
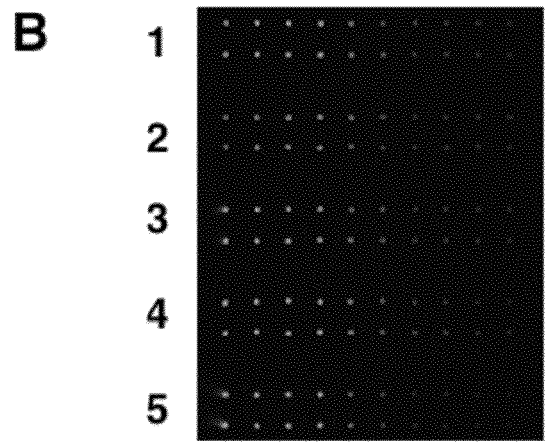
Figure 3C:
Figure 4:
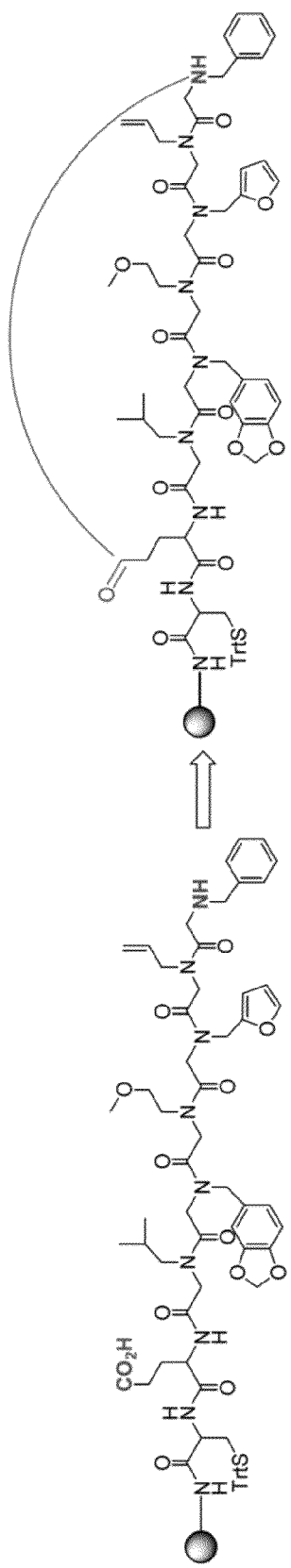
FIG. 4—Cyclization reaction of model peptoid on bead.

Serial dilutions of the five peptoids shown in FIGS. 3A-C were spotted robotically onto PEGylated, maleimide-activated glass microscope slides (Marthandan et al., 2005) and the slides were then washed rigorously. In order to demonstrate the immobilization of the cyclic peptoids, the slides were incubated with Cy3-labeled Streptavidin and scanned. As expected, the amount of protein captured decreased as the amount of peptoid spotted decreased, confirming that the fluorescence is indeed due to specific capture of the protein by the peptoid (FIG. 3B). To demonstrate that the Cys residue retains the cyclic peptoid to the maleimide-derivatized slide, the inventors synthesized two fluorescein-conjugated linear peptoids that were identical except for the presence and absence of Cys. These were spotted onto a slide, which was then scanned after washing. As shown in FIG. 3C, detectable fluorescence was seen only where the Cys-containing peptoid was spotted. This study confirms that the linear encoding molecule (see FIG. 1) will not be retained on the slide when the mixture of it and the Cys-containing cyclic molecule are spotted onto the slide and thus will not interfere with screening experiments.

Example 2

A Screen for Specific Autoreactive T Cell Ligands in EAE

For purposes of combination therapy using the antigen surrogates of formula I and using T-cell ligands, the following experimental is provided. The Multiple Sclerosis (MS) (Noseworthy et al., 2000)-like condition of EAE is induced in genetically susceptible strains of rodents by immunization with myelin proteins or peptides, or by passive transfer of myelin-specific CD4+ T cells (Zamvil and Steinman, 1990). Studies in EAE indicate that myelin-specific CD4+ T cells that have become activated in the periphery, and produce pro-inflammatory cytokines, play a major role in disease pathogenesis of MS (Zamvil and Steinman, 1990). Moreover, these T cells express T cell receptors that are believed to preferentially recognize myelin basic protein in the central nervous system of affected individuals leading to destruction of the myelin sheath and, ultimately, neurological deficit (Zamvil and Steinman, 1990). Therefore, a therapeutic strategy that specifically targets only autoreactive T cells would be interesting to investigate for MS as well as for other T cell-mediated diseases. As a first step, the inventors focused on the isolation of synthetic compounds capable of highly specific binding to autoreactive T cells in EAE.

To accomplish this, the inventors adapted a screening strategy developed previously in their laboratory for the isolation of peptoids (Simon et al., 1992) that bind to integral membrane receptors with high specificity (Udugamasooriya et al., 2008). In this protocol, cells that do or do not express the target receptor, but are presumed to be otherwise identical, are labeled with red and green quantum dots, respectively. The two cell types are then mixed and incubated with thousands of hydrophilic beads, each of which displays a unique peptide. Beads that bind only the red-labeled cells and not the green cells are then collected, the presumption being that this reflects highly specific binding to the target receptor since the peptoid must ignore all other molecules on the cell surface in order to exclude the green cells and be scored as a "hit"

To apply this two-color screening technology to the present problem, EAE was induced in B10.PL mice by immunization with the myelin basic protein peptide Ac1-11 (MBP Ac1-11). Immunization with this myelin peptide results in activation and expansion of CD4+ T cells expressing the MBP Ac1-11 specific Vα2.3/Vβ8.2 TCR (Ando et al., 1989). EAE and healthy control mice were sacrificed following the development of clinically definite EAE and the CD4+ T cells were isolated. CD4+ T cells from EAE mice were labeled with red-emitting quantum dots and the T cells from the control mice were labeled with green-emitting quantum dots. The cells were then mixed together in a 1:1 ratio and incubated with a bead-displayed peptoid library containing approximately 300,000 peptoids. The inventors' hypothesis was that the millions of different T cells in the overall population should all be present at low levels and that the two populations would be rather similar. The major exception would be an increased number of MBP Ac1-11-specific autoreactive T cells that expanded in response to immunization with the autoantigen in the EAE mice. This suggested that if a bead was found to bind only red cells, these were highly likely to be the autoreactive T cells.

Following incubation with the peptoid beads, the inventors identified two putative hit peptoids that were observed to bind specifically to CD4+ T cells from EAE mice and not to T cells from healthy control mice. An additional photograph is shown depicting a peptoid bead that bound non-specifically to CD4+ T cells from both EAE mice and healthy control mice. The peptoids on the two beads scored as hits were sequenced by Edman degradation (Alluri et al., 2003) and their structures determined (data not shown). The two "hits" were found to have some sequence similarity. The inventors elected to focus on one of the peptoids (AG12A) for more detailed characterization.

The AG12A Peptoid is a Ligand for EAE Autoreactive T Cells.

To determine whether AG12A was binding to the autoreactive TCR, the inventors took advantage of the existence of transgenic mice, in which the vast majority of CD4+ T cells express the MBP Ac1-11 specific TCR (Vα2.3/Vβ8.2 TCR) (Goverman et al., 1993). CD4+ T cells were isolated from these mice and tested for binding to AG12A. This was done in several ways. First, AG12A was resynthesized on beads, as was a control peptoid not selected as a T cell ligand. The beads were then incubated with red quantum dot-labeled T cells. CD4+ T cells from MBP Ac1-11 TCR transgenic mice bound to AG12A displayed on beads, where as wild-type CD4+ T cells did not.

To probe the binding of AG12A to the MBP Ac1-11 specific T cells further, the inventors performed a chemical cross-linking experiment that involves the oxidation of dihydroxyphenylalanine (DOPA) attached to the peptoid to an orthoquinone intermediate. This intermediate can then cross-link to nearby nucleophilic residues on the target receptor protein (Burdine et al., 2004; Liu et al., 2006; Lim et al., 2007). Cross-linking would be observed only if DOPA-AG12A and the receptor target are in close proximity, since extensive control experiments have shown that this chemistry does not couple molecules unless they are in a complex (Liu et al., 2006). CD4+ T cells from Vα2.3/Vβ8.2 TCR transgenic mice were incubated with increasing concentrations of biotin-labeled DOPA-AG12A or a control DOPA-peptoid labeled with biotin. After treatment with sodium periodate, the cells were then stained with fluorochrome-conjugated streptavidin and an anti-CD4+ antibody conjugated to a different fluorochrome. Peptoid binding to the T cells was assessed by calculating the mean fluorescence intensity of CD4+/streptavidin+ cells. AG12A was found to bind to MBP Ac1-11 specific T cells with a $K_D$ of approximately 40 μM. However, no interaction between biotinylated AG12A and T cells obtained from a wild-type mouse could be detected, nor did the biotinylated control peptoid bind to the Vα2.3/Vβ8.2 TCR transgenic T cells.

The peptoid-cell interaction was also analyzed by SOS-PAGE and Western blotting with NeutrAvidin horse radish peroxidase (NA-HRP). A biotin-containing product with an apparent mass of 45 kDa was detected when Biotin-DOPA-AG12A was incubated with TCR transgenic T cells, but not with CD4− cells or CD4+ T cells from a wild-type mouse. The molecular mass of the TCR α and β chains are approximately 45 and 40 kDa respectively (Zamvil and Steinman, 1990), suggesting cross-linking of AG12A to the TCR. Moreover, when the blot was probed with an α-Vα2 TCR antibody, a product was observed at approximately 45 kDa that overlapped with the band detected with NA-HRP, further suggesting that AG12A cross-links to the MBP Ac1-11 specific TCR.

AG12A is a Specific Antagonist of Antigen-Mediated Autoreactive T Cell Proliferation.

To test the possibility that peptoid-TCR binding might antagonize antigen-specific T cell proliferation, CD4+ T cells from MBP Acl-11 TCR transgenic mice were incubated with increasing concentrations of AG12A or a control peptoid, labeled with carboxyfluorescein diacetate succinimidyl ester (CFSE), and stimulated with MBP Ac-11 peptide and antigen presenting cells. CSFE is cell permeable in the ester form, but these groups are hydrolyzed once the compound enters the cell, rendering it cell impermeable. Thus, cell division results in dilution of the intracellular concentration of the fluorophore. After incubation for 5 days, cell division was measured using flow cytometry. AG12A was found to inhibit proliferation of the MBP Acl-11 autoreactive T cells in a dose-dependent fashion with an $IC_{50}$ of approximately 60-80 µM. This decrease in proliferation was not seen when the transgenic T cells were stimulated in the presence of a control peptoid, nor did AG12A inhibit proliferation of B cells. Most importantly, AG12A also did not inhibit the antigen-stimulated proliferation of Myelin Oligodendrocyte Glycoprotein (MOG) 35-55 specific TCR transgenic T cells. This experiment demonstrates clearly that the effect of AG12A is specific to T cells that recognize the MBP Acl-11 antigen and is not due to some general affinity for any activated T cell.

Ex Vivo Inactivation of Autoreactive T Cells Using a Ruthenium-Peptoid Conjugate.

An antagonist with a potency better than the 40 µM $IC_{50}$ exhibited by AG12A (typical of a primary screening hit (Kodadek et al., 2004)) would be desirable for practical applications. To achieve this, AG12A was conjugated to a ruthenium(II) tris-bipydridyl complex that is an efficient catalyst for the generation of singlet oxygen when irradiated with visible light (Lee et al., 2008). Singlet oxygen is a highly reactive species that will modify and inactivate most proteins, but which has a limited diffusion radius of only 40-80 Å. Thus, only proteins in the immediate vicinity of the ruthenium "warhead" are affected. When delivered to target proteins by the peptoid ligand, highly specific photo-triggered protein inactivation can be achieved (Lee et al., submitted for publication). MBP Acl-11 specific TCR transgenic T cells were incubated with increasing concentrations of the AG12A-ruthenium conjugate or a control peptoid-ruthenium conjugate and the cells were irradiated with visible light (<380 nm cut-off filter). Following the ten-minute irradiation, the T cells were activated with the autoantigen MBP Acl-11 in the presence of antigen presenting cells. Cell proliferation was assessed using a tritiated thymidine assay. The AG12A-ruthenium conjugate inhibited proliferation of MBP Acl-11 specific autoreactive T cells potently at a concentration of 100 nM. This represents an approximately 700-fold improvement over the activity of the peptoid alone. This inhibition was not seen when CD4+ T cells from MOG 35-55 TCR transgenic mice were used, demonstrating again the specificity of AG12A for MBP Acl-11 specific autoreactive T cells.

Photophoreresis therapies exist in which cells are removed, treated with a photoreactive drug, exposed to UV light, and re-infused back into the patient (Rostami et al., 1999; Besnier et al., 2002; Cavaletti et al., 2006). Thus, although the blue light required to trigger ruthenium tris-bipyridl-catalyzed singlet oxygen production cannot penetrate into a living organism, the ex vivo inactivation of autoimmune T cells by a peptoid-ruthenium conjugate seems feasible given this precedent. To test this theory and confirm that the autoreactive T cells have been rendered unresponsive following treatment with the peptoid-ruthenium conjugate and light, the inventors used an adoptive transfer model of EAE. CD4+ T cells were isolated from MBP Acl-11 TCR transgenic mice, treated with the AG12A-ruthenium conjugate or the control peptoid-ruthenium conjugate, irradiated, stimulated with MBP Acl-11 peptide in the presence of antigen presenting cells, and injected back into naïve recipients. These animals were then observed for clinical signs of EAE. As anticipated, animals injected with antigen-stimulated autoreactive T cells that had been exposed to the control peptoid-ruthenium conjugate or no peptoid developed EAE. When the T cells were neither stimulated with antigen nor exposed to a peptoid, adoptive transfer did not result in EAE, as expected. Strikingly, MBP Act-11 specific CD4+ T cells stimulated with antigen and treated with the AG12A-ruthenium conjugate did not induce EAE in the recipient animals. This experiment demonstrates the feasibility of using autoreactive T cell-targeted ruthenium peptoid conjugates as potent photo-triggered inhibitors of autoimmune T cell activation ex vivo.

Example 3

Pemphigus Vulgaris

A library of 10,000 cyclic peptoids on an array was generated pursuant to the general methods described herein. The library is screened against labeled (or unlabeled) pemphigus autoantibody and certain ligands were found bound to the autoantibodies on the support. The autoantibodies may be obtained from, for example, sera of patients having pemphigus vulgaris (PV) using soluble recombinant extracellular domains of desmoglein 3 to obtain affinity purified anti-desmoglein 3 autoantibodies as described in Ding et al., "The Anti-Desmoglein I Autoantibodies in Pemphigus Vlugaris Sera are Pathogenic", The Journal of Investigative Dermatology, vol 112, No. 5, pp 739-743 (1999). The bound autoantibodies associated with the particular ligands were detected and then the identity of the antigen surrogate was determined from its position on the array. The preferred cyclic peptoids which act as antigen surrogates comprise 5-mers substituted with R1-R5 wherein R1-R5 is independently selected from the group consisting of C1-C6 alkyl, C1-C6 alkyl substituted with at least one moiety selected from —OH, —OR (wherein R is C1-C6alkyl), —NR5R6; aryl or heteroaryl or aryl or heteroaryl substituted with at least one moiety selected from halogen, CF3, —OH or —OR.

The preferred antigen surrogate comprises a compound of formula I:

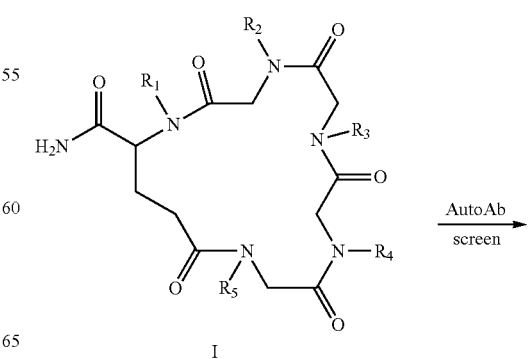

I

-continued

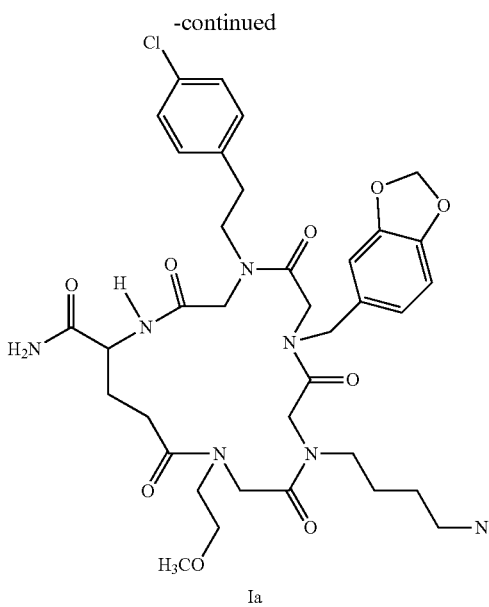

Ia

Wherein R1-R5 are generically as described above and are specifically as shown in the structure on the right (compound 1a). This compound is a ligand for the autoantibody for pemphigus vulgaris. The above compound had a binding affinity in solution of approximately $10^{-5}$ M to the pemphigus vulgaris autoantibody to the Dsg autoantigen. It is believed that additional oligomers found pursuant to the processes described herein will have binding affinities ($K_D$) in solution of between $10^{-5}$ to $10^{-9}$ M. In this example, 10,000 cyclic peptoids on a support were screened against the known pemphigus vulgaris autoantibody (Dsg3) to find the preferred hit which, in solution binding studies had the $10^{-5}$ binding affinity.

Example 4

Discussion

The inventors have demonstrated here a combinatorial library screening protocol that is capable of yielding synthetic molecules that bind to autoantibodies for autoimmune diseases or conditions such as pemphigus vulgaris and/or pemphigus foliaceus. Autoantigens for pemphigus vulgaris and penphigus foliaceus include desmoglein 3 and desmoglein 1 respectively. The autoantibodies to each of these autoantigens are called anti-desmoglein 1 (pathogenic in pemphigus foliaceus) and anti-desmoglein 3 (pathogenic in pemphigus vulgaris) and include multiple variants. Anti-desmoglein 1 antibodies are also found in pemphigus vulgaris. The present invention thus includes methods of identifying high affinity ligands to autoantibodies associated with an autoimmune disease or disorder using the screening protocols identified herein. These ligands can also be used in combination with ligands against antigen-specific autoimmune T cells having high specificity.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

VI. REFERENCES

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,275,149
U.S. Pat. No. 4,277,437
U.S. Pat. No. 4,366,241
U.S. Pat. No. 4,680,338
U.S. Pat. No. 4,843,092
U.S. Pat. No. 5,141,648
U.S. Pat. No. 5,443,826
U.S. Pat. No. 5,563,250
U.S. Pat. No. 5,599,795
U.S. Pat. No. 5,856,456
U.S. Pat. No. 5,880,270
Alluri et al., *J. Am. Chem. Soc.* 125:13995-4004, 2003.
Ando et al., *Cell Immunol.*, 124:132-43, 1989.
Arend & Dayer, *Arthritis Rheum.*, 38:151-60, 1995.
Arend et al., *Annu. Rev. Immunol*, 16:27-55, 1998.
Arend, *Arthritis Rheum.*, 44:2224-2234, 2001.
Autenrieth et al., *Infect. Immun.*, 62:2590-9, 1994.
Ball, *Ann. Rheum. Dis.*, 30:213-223, 1971.
Bendzen et al., *Scand. J. Rheumatol.*, 28:599-606, 1988.
Besnard et al., *Gut*, 43(5):634-38, 1998.
Besnier et al., *Photodermatol. Phowimmunol. Photomed.*, 18:36-41, 2002.
Bielekova et al., *Nat. Med.*, 6:1167-75, 2000.
Blumberg et al., *Arthritis Rheum.*, 7:93-7, 1964.
Botoman et al., *Am. Pam. Physician*, 57(1):57-68, 1998.
Brandt et al., *Arthritis Rheum.*, 43:1346-52, 2000.
Braun et al., *Arthritis Rheum.*, 42:2039-44, 1999.
Brewerton et al., *Lancet*, 1:904-907, 1973a.
Brewerton et al., *Lancet*, 1:956-957, 1973b.
Brynskov et al., *N. Engl. J. Med.*, 321(13):845-50, 1989.
Burdine et al., *J. Amer. Chem. Soc.*, 126:11442-11443, 2004.
Burger & Dayer, *Neurology*, 45(6 Suppl. 6):S39-43, 1995.
Cahn et al., In: *The Spondylarthritides*, Calin et al. (Eds.), Oxford, UK. Oxford University Press, 179, 1998.
Cann et al., *Gut*, 24(5):405-11, 1983.
Cavaletti et al., *Neural. Sci.*, 27:24-32, 2006.
Chomarat et al., *Arthritis Rheums.*, 38:1046-54, 1995.
Coles et al., *N. Engl. J. Med.*, 359:1786-801, 2008.
de Haan et al., *Mol. Immunol.*, 42:365-73, 2005.
De Jager et al., *Semin. Nucl. Med.*, 23(2):165-179, 1993.
de Waal et al., *J. Exp. Med.*, 174:1209-20, 1991.
Dinarello, *Int. Rev. Immunol.*, 16:457-99, 1998.
Dionne et al., *Clin. Exp. Imunol.*, 112(3):435-42, 1998.
Doolittle and Ben-Zeev, *Methods Mol Biol*, 109:215-237, 1999.
Doran et al., *J. Rheumatol.* 30(2):316-20, 2003.
Drossman et al., *Dig Dis Sci.*, 38(9):1569-80, 1999.
Drossman et al., *Gastroenterology*, 112(6):2120-37, 1997.

Drossman et al., *Gastroenterology*, 112(6):2120-37, 1997.
Eastgate et al., *Lancet*, 2:706-9, 1988.
Ettehadi et al., *Clin. Exp. Immunol.*, 96:146-51, 1994.
Everhart and Renault, *Gastroenterology*, 100(4):998-1005, 1991.
Fearon and Locksley, *Science*, 72:50-53, 1996.
Feldtkeller et al., *Rheumatol. Int.* 23(2):61-66, 2003.
Fellerman et al., *Am. J. Gastroenterol.*, 93(10):1860-66, 1998.
Firestein et al., *Arthritis Rheuin.*, 37:644-52, 1994.
Fujikawa et al., *Ann. Rheuin. Dis.*, 54:318-20, 1995.
Funakoshi et al., *Digestion*, 59(1):73-78, 1998.
Galley & Webster, *Br. Anaesth.*, 77:11-16, 1996.
Gladman et al., *J. Rheumatol.*, 22:675-9, 1995.
Gladman et al., *Q. J. Med.*, 62:127-141, 1987.
Gladman, *Rheum Dis Clin North Am*, 18:247-56, 1992.
Goverman et al., *Cell*, 72:551-60, 1993.
Gulbis and Galand, *Hum. Pathol.*, 24(12):1271-1285, 1993.
Gwee et al., *Gut*, 44(3):400-6, 1999.
Hahn & Tsao, In: *Dubois' Lupus Erythematosus*, 4$^{th}$ Ed., Wallace & Hahn (Eds.), Lea and Febiger, Philadelphia, 195-201, 1993.
Hannum et al., *Nature*, 343:336-40, 1990.
Harrison et al., *Rheumatol.*, 25(12):2324-2330, 1998.
Harrison et al., *J Rheumatol.*, 25(12):2324-2330, 1998.
Hart et al., *Clin. Exp. Immunol.*, 99(3):331-337, 1995.
Hart et al., *Immunology*, 84:536-42, 1995.
Hauser, *N. Eng. J. Med.*, 359:1838-1841, 2008.
Hemmer and Hartung, *Ann. Neural.*, 62:314-26, 2007.
Hoffenberg et al., *J. Pediatr.*, 134(4):447-52, 1999.
Hohler et al. *J. Invest. Dermatol.*, 109(4):562-5, 1997.
Hollander et al., *Ann. Intern. Med.*, 105:883-85, 1986.
Hollander, *Scand. J. Gastroenterol.* 27:721-26, 1992.
Horwitz and Fisher, *N. Engl. J. Med.*, 344(24):1846-50, 2001.
Howell et al., *Science*, 246:668-70, 1989.
Jacob et al., *Proc. Natl. Acad. Sci. USA*, 87:1233-7, 1990.
Jailwala et al., *Ann. Intern. Med.*, 133(2):136-47, 2000.
Jarvis, *Curr Opin Rheumatol.*, 10:459-467, 1998.
Jarvis, *Curr Opin Rheumatol.*, 10:459-467, 1998.
Jarvis, *Pediatr Ann.*, 31:437-446, 2002.
Jones et al., *Br. J. Rheumatol.*, 33:834-9, 1994.
Jonsson and Brokstad, In: *A Textbook of Rheumatology*, 6$^{th}$ Ed., Philadelphia: Lippincott Williams & Wilkins, 495-504, 2001.
Jonsson et al., *Br J Rheumatol.*, 32: 578-81, 1993.
Jonsson et al., *Oral Dis.*, 8:130-140, 2002.
Kahle et al., *Ann. Rheum. Dis.*, 51:731-4, 1992.
Kellow and Phillips, *Gastroenterology*, 92(6):1885-93, 1987.
Khan, *Clin. Exp. Rheumatol.* 20(6):6-10, 1998.
Khan, In: *Ankylosing spondylitis and related spondyloarthropathies*, Spine, State of the Art Reviews, 1990.
Kodadek et al., *Ace. Chem. Res.*, 37:711-718, 2004.
Kotake et al., *Infect. Immun.*, 67:2682-6, 1999.
Kotzin & O'Dell, In: *Samler's Immunologic Diseases*, 5$^{th}$ Ed., Frank et al. (Eds.), Little Brown & Co., Boston, 667-97, 1995.
Kotzin, *Cell*, 85:303-06, 1996.
Kuboyama, *Kurume Med. J.*, 45(1):33-37, 1998.
Lahesmaa et al., *J. Immunol.*, 148:3079-85, 1992.
Lee et al., *Mol. Biosyst.*, 4:59-65, 2008.
Lee et al., *Mol. Biosyst*, 4:59-65, 2008.
Leiper et al., *Baillieres Clin. Gastroenterol.*, 12(1):179-99, 1998.
Lim et al., *J. Amer. Chem. Soc.*, 129:12936-12937, 2007.
Lim et al., *J. Amer. Chem. Soc.*, 129:12936-12937, 2007.
Lipsky, In: *Harrison's principles of internal medicine*, Fauci et al. (Eds.), 14$^{th}$ Ed., NY, McGraw-Hill, 1880-1888, 1998.

Liu et al., *J. Amer. Chem. Soc.*, 128:15228-15235, 2006.
Lo et al., *Immunol Rev.*, 169:225-239, 1999.
Lugering et al., *Ital. J. Gastroenterol. Hepatol.*, 30(3):338-44, 1998.
Lynn and Friedman, *N. Engl. J. Med.*, 329(26):1940-5, 1993.
Macatonia et al., *J. Immunol.*, 150:3755-65, 1993.
Makowiec et al., *Z. Gastroenterol.*, 36(8):619-24, 1998.
Marsal et al., *Rheumatology*, 38:332-7, 1999.
McAlindon et al., *Gut*, 42(2):214-19, 1998.
McGonagle et al., *Arthritis Rheum.*, 41:694-700, 1998.
McGonagle et al., *Curr. Opin. Rheumatol.*, 11:244-50, 1999.
Mertz et al., *Gastroenterology*, 118(5):842-8, 2000.
Moll & Wright, *Ann. Rheum. Dis.*, 32:181-201, 1973.
Moll & Wright, *Semin. Arthritis Rheum.*, 3:55-78, 1973.
Murch, *Nutrition*, 14:780-83, 1998.
Nakamura et al., In: *Handbook of Experimental Immunology* (4$^{th}$ Ed.), Weir et al. (Eds), 1:27, Blackwell Scientific Publ., Oxford, 1987.
Neal et al., *BMJ*, 314(7083):779-82, 1997.
Nielen et al., *Arthritis Rheum.*, 50(2):380-386, 2004.
Noseworthy et al., *N. Engl. J. Med.*, 343:938-52, 2000.
Ohnishi et al., *Int. Immunol.*, 6:817-30, 1994.
Olivos et al., *Org. Lett.*, 4:4057-4059, 2002.
Partsch et al., *Br. J. Rheumatol.*, 24:518-23, 1997.
Pimentel et al., *Am. J. Gastroenterol.*, 95(12):3503-6, 2000.
Pociot et al., *Scand. Immunol.*, 42:501-4, 1995.
Popkov et al., *Nat. Proc. Acad. Sci. USA*, 106(10:4378-83, 2009.
Prieur et al., *Lancet*, 2:1240-2, 1987.
Racke, *Curr. Protoc. Neurosci.*, Chapter 9:Unit 97, 2001.
Rantapaa-Dahlqvist et al., *Arthritis Rheum.*, 48(10):2741-2749, 2003.
Reimund et al., *Eur. J. Clin. Invest.*, 28(2):145-50, 1998.
Ribbens et al., *Eur. Cytokine Netw.*, 11:669-76, 2000.
Rogler &. Andus, *World J. Surg.*, 22(4):382-89, 1998.
Rooney et al., *Rheumatol. Int.*, 10:217-9, 1990.
Rostami et al., *Mull. Scler.*, 5:198-203, 1999.
Rothstein, *Med. Clin. North Am.*, 84(5):1247-57, 2000.
Ruemmele et al., *Gastroenterol.*, 115(4):822-29, 1998.
Saiki et al., *Scared. J. Gastroenterol.*, 33(6):616-22, 1998.
Salomonsson et al., *Arthritis Rheum.*, 48:3187-201, 2003.
Salomonsson et al., *Scand. J. Immunol.*, 55:336-42, 2002.
Salvarani et al., *Curr. Opin. Rheumatol.*, 10:299-305, 1998.
Sandler, *Gastroenterology*, 99(2):409-15, 1990.
Sartor, *Am. J. Gastroenterol.*, 92(12):5S-11S, 1997.
Schellekens et al., *Arthritis Rheum.*, 43(1):155-163, 2000.
Schlaak et al., *Clin. Exp. Rheumatol.*, 14:155-62, 1996.
Schlaak et al., *Eur. J. Immunol.*, 22:2771-6, 1992.
Schlosstein et al., *NE J. Medicine*, 288:704-706, 1973.
Schneider, *Curr. Pharm. Biotechnol.*, 9:431-8, 2008.
Schreiber, *Neth. J. Med.*, 53(6):S24-31, 1998.
Sieper & Braun, *Arthritis Rheum.*, 38:1547-54, 1995.
Simon et al., *Clin. Exp. Immunol.*, 94:122-6, 1993.
Simon et al., *Proc. Natl. Acad. Sci. USA*, 89:9367-71, 1992.
Simon et al., *Proc. Natl. Acad. Sci. USA*, 91:8562-6, 1994.
Soderholm et al., *Gastroenterol.*, 117:65-72, 1999.
Stack et al., *Lancet*, 349(9051):521-24, 1997.
Stuve, *J. Neural. Sci.*, 274:39-41, 2008.
Talley et al., *Gastroenterology*, 109(6):1736-41, 1995.
Targan et al., *N. Engl. J. Med.*, 337(15):1029-35, 1997.
Udugamasooriya et al. *J. Amer. Chem. Soc.*, 130:5744-5752, 2008.
van den Berg, *Semin Arthritis Rheum.*, 30(5 Suppl. 2):7-16, 2001.
van Dullemen et al., *Gastroenterol.*, 109(1):129-35, 1995.
van Hogezand & Verspaget, *Drugs*, 56(3):299-305, 1998.
Vandenbark et al., *Nature*, 341:541-4, 1989.

Warrington et al., *Arthritis Rheum.*, 44:13-20, 2001.
Wawrzynczak and Thorpe, *FEBS Lett*, 207(2):213-216, 1986.
Weyand and Goronzy, *Ann. NY Acad. Sci.*, 987:140-9, 2003.
Whitehead et al., *Gastroenterology*, 98(5 Pt 1):1187-92, 2000.
Wordsworth, In: *Genes and Arthritis*, Brit. Medical Bulletin, 51:249-266, 1995.
Wraith et al., *Cell*, 57:709-15, 1989.
Wright, *Ann. Rheum. Dis.*, 15:348-56, 1956.
Wright, *Clin. Orthop. Related Res.*, 143:8-14, 1979.
Xanthou et al., *Arthritis Rheum.*, 44: 408-18, 2001.
Yin et al., *Arthritis. Rheum.*, 40:1788-97, 1997.
Yin et al., *Rheumatology*, 38:1058-67, 1999.
Zamvil and Steinman, *Annu. Rev. Immunol.*, 8:579-621, 1990.
U.S. Pat. No. 4,680,338
U.S. Pat. No. 5,141,648
U.S. Pat. No. 5,563,250
U.S. Pat. No. 5,617,060,
U.S. Publn. 2002/0137106
Alluri et al., *J. Amer. Chem. Soc.*, 125:13995-14004, 2003.
Alluri et al., *Mol. BioSystems*, 2:568-579, 2006.
Banerjee et al., *J. Natural Prod.*, 71:492-496, 2008.
Figliozzi et al., *Methods Enzymol.*, 267:437-447, 1996.
Fouladi, *Cancer Invest.*, 24:521-527, 2006.
Hamada and Shioiri, *Chem. Rev.*, 105:4441-4482, 2005.
Ho et al., *Cin. Immunol. Immunopathol.*, 80:S40-S45, 1996.
Horn et al., *Bioconj. Chem.*, 15:428-435, 2004.
Johnson et al., In: *Biotechnology And Pharmacy*, Pezzuto et al. (Eds.), Chapman and Hall, NY, 1993.
Joo et al., *J. Amer. Chem. Soc.*, 128:13000-13009, 2006.
Kwon and Kodadek, *J. Amer. Chem. Soc.*, 129:1508-1509, 2007.
Lech-Maranda et al., *Mini Rev. Med. Chem.*, 7:1062-1069, 2007.
Li et al., *Chem. Comm.*, 581-583, 2005.
Lim et al., *J. Amer. Chem. Soc.*, 129:7750-7751, 2007.
Liu et al., *J. Amer. Chem. Soc.*, 124:7678-7680, 2002.
MacBeath et al., *J. Amer. Chem. Soc.*, 121:7967-7968, 1999.
Martin, *Pure Appl. Chem.*, 79:193-200, 2007.
Paulick et al., *J. Comb. Chem.*, 8:417-426, 2006.
PCT Pubin. WO 98/59360
Reddy and Kodadek, *Proc. Natl. Acad. Sci. USA*, 102:12672-12677, 2005.
Reddy et al., *Chem. & Biol.*, 11:1127-1137, 2004.
Rezai et al., *J. Amer. Chem. Soc.*, 128:14073-14080, 2006a.
Rezai et al., *J. Amer. Chem. Soc.*, 128:2510-2511, 2006b.
Satoh et al., *Biochem. Biophys. Res. Commun.*, 224, 438-443, 1996.
Schena et al, *Science*, 270:467-470, 1995.
Scott et al., *Proc. Natl. Acad. Sci. USA*, 96:13638-13643, 1999.
Shalon et al., *Genome Res.*, 6:639-645, 1996.
Shin et al., *J. Am. Chem. Soc.*, 129:3218-3225, 2007.
Simon et al., *Proc. Natl. Acad. Sci. USA*, 89:9367-9371, 1992.
Udugamasooriya and Spaller, *Biopolymers*, 89:653-667, 2008.
Udugamasooriya et al., *J. Amer. Chem. Soc.*, 130:5744-5752, 2008.
Uttamchandani et al., *Curr. Op. Chem. Biol.*, 9:4-13, 2005.
Venkatesh et al., *Proc. Natl. Acad. Sci. USA*, 97:761-766, 2000.
Wawrzynczak & Thorpe, *Cancer Treat Res.*, 37:239-51, 1988.
Xiao et al., *J. Comb. Chem.*, 9:592-600, 2007.
Zuckermann et al., *Med. Chem.*, 37:2678-2685, 1994.

What is claimed is:

1. A method of identifying an antigen surrogate constrained peptoid ligand that is specifically recognized by autoantibodies comprising:
    (1) exposing an autoantibody associated with an autoimmune disease selected from pemphigus vulgaris to a peptoid ligand library comprising constrained peptoid ligands;
    (2) detecting at least one constrained peptoid ligand bound to the autoantibody and
    (3) identifying said bound constrained peptoid ligand;
    wherein said peptoid ligand is bound to a support and
    wherein said peptoid ligand has the formula:

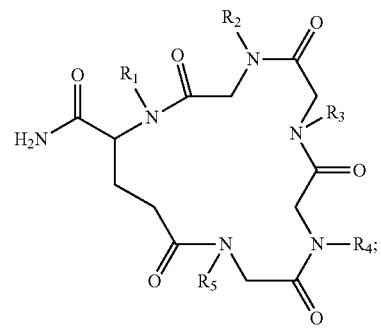

wherein $R_1$-$R_5$ are independently selected from the group consisting of hydrogen, alkyl, allyl, C2-C6 alkynyl, methyl, ethyl, n-propyl, isopropyl, n-butyl, isobutyl, sec-butyl, tert-butyl, pentyl, hexyl, isopentyl, aryl, heteroaryl, furanyl, indolyl, thiophenyl, thiazolyl, imidazolyl, isoxazoyl, oxazoyl, piperonyl, pyrazoyl, pyrrolyl, pyrazinyl, pyridyl, pyrimidyl, pyrimidinyl, purinyl, cinnolinyl, benzofuranyl, benzothienyl, benzotriazolyl, benzoxazolyl, quinolone, isoxazolyl, isoquinoline cycloalkyl, alkenyl, cycloalkenyl, phenyl, pyridyl, methoxyethyl, methylbenzyl and C1-C6 alkyl; wherein each of $R_1$-$R_5$ may optionally be substituted with a group selected from halogen (Cl, F, Br, I), —$NH_2$, —OH, —OC1-C6alkyl, —SH and pharmaceutically acceptable salts thereof.

2. The method of claim 1, wherein said support is a bead, a chip, a filter, a dipstick, a membrane, a polymer matrix or a well.

3. The method according to claim 1 wherein the peptoid ligand comprises the formula:

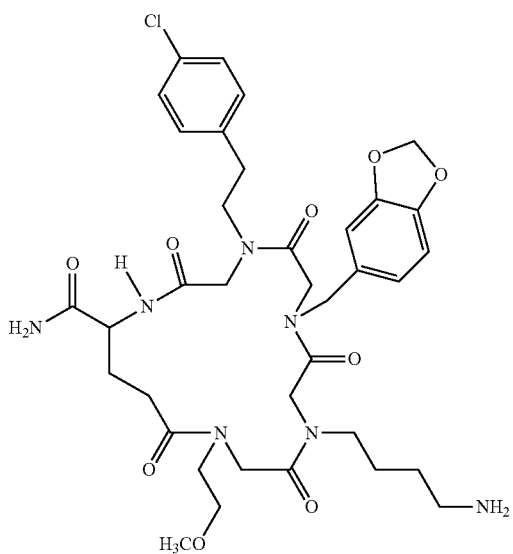 [SMILES: COCCN1CC(=O)N(CCCCN)CC(=O)N(Cc2ccc3c(c2)OCO3)CC(=O)N(CCc2ccc(Cl)cc2)CC(=O)NC(C(N)=O)CCC1=O]

or a pharmaceutically acceptable salt thereof.

4. The method according to claim 1 comprising a peptoid ligand of formula I and, optionally, a peptoid having the formula:

Formula II

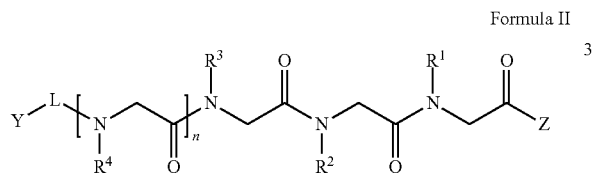

Formula III

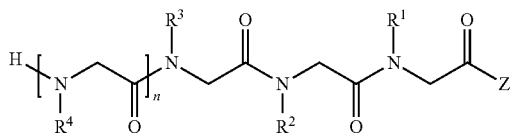

wherein n is 0-8; L is linker; Y is toxin or antibody fragments; Z is $NH_2$, $N(C1-C6\ alkyl)_2$, OH or $O(C1-C6\ alkyl)$; and each of $R_1$-$R_8$ (with each value of n above 4 adding a next R group in numerical order to Formula I or Formula II), are independently selected from the group consisting of hydrogen, alkyl, allyl, methyl, ethyl, n-propyl, isopropyl, n-butyl, isobutyl, sec-butyl, tert-butyl, pentyl, hexyl, isopentyl, aryl, heteroaryl, furanyl, indolyl, thiophenyl, thiazolyl, imidazolyl, isoxazoyl, oxazoyl, piperonyl, pyrazoyl, pyrrolyl, pyrazinyl, pyridyl, pyrimidyl, pyrimidinyl, purinyl, cinnolinyl, benzofuranyl, benzothienyl, benzotriazolyl, benzoxazolyl, quinolone, isoxazolyl, isoquinoline cycloalkyl, alkenyl, cycloalkenyl, phenyl, pyridyl, methoxyethyl, methylbenzyl, C1-C6 alkyl optionally substituted with $NH_2$, OH, or SH and C2-C6 alkynyl optionally substituted with $NH_2$; OH or SH.

* * * * *